(12) United States Patent  
McCollough et al.

(10) Patent No.: US 9,111,334 B2  
(45) Date of Patent: Aug. 18, 2015

(54) DIELECTRIC ENCODING OF MEDICAL IMAGES

(71) Applicant: ELLUMEN, INC., Arlington, VA (US)

(72) Inventors: Todd R. McCollough, Barrington, IL (US); William J. McCollough, Lorton, VA (US)

(73) Assignee: ELLUMEN, INC., Arlington, VA (US)

( * ) Notice: Subject to any disclaimer, the term of this patent is extended or adjusted under 35 U.S.C. 154(b) by 0 days.

(21) Appl. No.: 14/069,661

(22) Filed: Nov. 1, 2013

(65) Prior Publication Data

US 2015/0125054 A1    May 7, 2015

(51) Int. Cl.
| | |
|---|---|
| G06K 9/00 | (2006.01) |
| G06T 7/00 | (2006.01) |
| G06T 11/00 | (2006.01) |
| G01R 33/02 | (2006.01) |
| A61B 5/05 | (2006.01) |

(52) U.S. Cl.
CPC .............. *G06T 7/0014* (2013.01); *G06T 11/005* (2013.01); *G06T 2207/10072* (2013.01); *G06T 2207/30024* (2013.01)

(58) Field of Classification Search
CPC ................ A61B 5/00; A61N 5/00; G06T 7/00
USPC .......... 382/128–134; 324/329, 637, 638, 639, 324/640, 694; 600/430
See application file for complete search history.

(56) References Cited

U.S. PATENT DOCUMENTS

| | | | |
|---|---|---|---|
| 5,103,181 A | 4/1992 | Gaisford et al. | |
| 5,841,288 A * | 11/1998 | Meaney et al. | 324/639 |
| 5,995,863 A | 11/1999 | Farace et al. | |
| 6,433,720 B1 | 8/2002 | Libove et al. | |
| 6,448,788 B1 | 9/2002 | Meaney et al. | |
| 6,972,714 B1 | 12/2005 | Baharav et al. | |
| 7,040,168 B1 | 5/2006 | Merkel | |
| 7,132,836 B2 * | 11/2006 | Peters et al. | 324/637 |
| 7,280,227 B2 | 10/2007 | Merkel et al. | |
| 7,378,855 B2 | 5/2008 | Moshe | |
| 7,550,969 B2 | 6/2009 | Zhdanov | |

(Continued)

FOREIGN PATENT DOCUMENTS

KR    10201140520 A    4/2011

OTHER PUBLICATIONS

U.S. Appl. No. 13/798,428, Mar. 13, 2013, McCollough et al.

(Continued)

*Primary Examiner* — Abolfazl Tabatabai  
(74) *Attorney, Agent, or Firm* — Foley & Lardner LLP

(57) ABSTRACT

Microwave imaging apparatus and method for completely imaging the human body (or portions thereof) in sufficient detail to render a timely and accurate medical diagnosis by trained medical professionals. The data conversion processes presented will not require physicians and radiologists to learn to use image data in a format they are not familiar with. Hounsfield encoded and/or MRI intensity encoded medical images in the DICOM format are provided from reconstructed dielectric images obtained from raw scattering data. This allows for the exchange of information created from microwave imaging techniques to be implemented with existing diagnostic tools and analysis techniques. Furthermore, methods are presented for converting image data with Hounsfield encoded units to an image with dielectric encoded units.

33 Claims, 31 Drawing Sheets

(56) References Cited

U.S. PATENT DOCUMENTS

| | | | |
|---|---|---|---|
| 7,804,309 B2 | 9/2010 | Cummins | |
| 7,809,427 B2 | 10/2010 | Winters et al. | |
| 7,933,786 B2 | 4/2011 | Wargin et al. | |
| 8,095,204 B2 | 1/2012 | Smith et al. | |
| 8,400,168 B2 | 3/2013 | Troxler et al. | |
| 2004/0077943 A1* | 4/2004 | Meaney et al. | 600/430 |
| 2008/0319285 A1 | 12/2008 | Hancock | |
| 2009/0273509 A1 | 11/2009 | Fullerton | |
| 2010/0113921 A1 | 5/2010 | Fear et al. | |
| 2011/0006785 A1* | 1/2011 | Gradinarsky | 324/640 |
| 2011/0028825 A1 | 2/2011 | Douglas et al. | |
| 2011/0119212 A1 | 5/2011 | De Bruin et al. | |
| 2011/0130656 A1 | 6/2011 | Son et al. | |
| 2011/0169933 A1 | 7/2011 | Touboul | |
| 2012/0019406 A1 | 1/2012 | Sarkis | |
| 2012/0158739 A1 | 6/2012 | Ah-Pine et al. | |
| 2012/0328076 A1 | 12/2012 | Ikhlef | |
| 2013/0018591 A1 | 1/2013 | Grzegorczyk | |
| 2014/0003699 A1* | 1/2014 | Moulik | 382/131 |

OTHER PUBLICATIONS

Andreas Christ et al., The Virtual Family—Development of Surface-Based Anatomical Models of Two Adults and Two Children for Dosimetric Simulations, Physics in Medicine and Biology 55, 2010, pp. N23-N38.

Ann Franchois et al., Mircrowave Imaging-Complex Permittivity Reconstruction with a Levenberg-Marquardt Method, IEEE Transactions on Antennas and Propagation, Feb. 1997, pp. 203-215, vol. 45, No. 2.

C. Gabriel et al., The Dielectric Properties of Biological Tissues: I. Literature Survey, Phys. Med. Bio. 41, 1996, pp. 2231-2249.

Chou et al., Development of a Rat Head Exposure Systems for Simulating Human Exposure to RF Fields from Handheld Wireless Telephones, Bioelectromagnetics 20, 1999, pp. 75-92.

Christian Weber, Development of Patient-Specific Electromagnetic Model (PSEM) Based on MR Breast Images, Sep. 27, 2010, pp. 1-36.

D.C. Zhu et al., Brain Water Content Measurement and Visualization With Applications Hydrocephalus, Proc. Intl. Soc. Mag. Reson. Med. 13, 2005, pp. 1099.

Daniel R. Messroghli et al., An Open-Source Software Tool for the Generation of Relaxation Time Maps in Magnetic Resonance Imaging, BMC Medical Imaging, 2010, 10:16, pp. 1-8.

David C. Zhu et al., Full-Brain $T_1$ Mapping Through Inversion Recovery Fast Spin Echo Imaging With Time-Efficient Slice Ordering, Magnetic Resonance in Medicine, 54, 2005, pp. 725-731.

Elise C. Fear et al., Confocal Imaging for Breast Cancer Detection: Localization of Tumors in Three Dimensions, IEEE Transactions on Biomedical Engineering, Aug. 2002, pp. 812-822, vol. 49. No. 8.

Elise C. Fear et al., Enhancing Breast Tumor Detection with Near-Field Imaging, IEEE Microwave Magazine, Mar. 2002, pp. 49-56.

Elise Fear et al., Microwave for Breast Cancer Detection?, IEEE Potentials, 2003, pp. 12-18.

Gary A. Ybarra et al., Microwave Breast Imaging, Emerging Technology in Breast Imaging and Mammography, 2007, Chapter 16, pp. 1-12.

H. Neeb et al., A New Method for Fast Quantitative Mapping of Absolute Water Content in Vivo, NeuroImage 31, 2006, pp. 1156-1168.

Hoi-Shun Lui et al., Development of Patient-Specific Breast Electromagnetic Model Based on Clinical Magnetic Resonance Images, IEEE, 2010, 4 pages.

J. Clegg et al., A Genetic Algorithm for Optimizing Multi-Pole Debye Models of Tissue of Dielectric Properties, Phys. Med. Biol. 57, 2012, pp. 6227-6243.

J. M. Sill et al., Realistic Breast Models for Second Generation Tissue Sensing Adaptive Radar System, The Second European Conference on Antennas and Propagation, 2007, 4 pages.

James et al., Direct Use of CT Scans for Hyperthermia Treatment Planning, IEEE Transactions on Biomedical Engineering, 1992, pp. 845-851, vol. 39, Issue 8.

M. Cavagnaro et al., Water Content Evaluation of a Human Tissue Using Magnetic Resonance Imaging: A Quantitative Benchmarking Approach, 2012 International Symposium on Electromagnetic Compatibility, IEEE, 2012, 6 pages.

M. Mazzurana et al., A Semi-Automatic Method for Developing an Anthropomorphic Numerical Model of Dielectric Anatomy by MRI, Physics in Medicine and Biology 48, 2003, pp. 3157-3170.

M. R. Sentinella et al., Enhanced Continuous Tabu Search in a Hybrid Evolutionary Algorithm for the Optimization of Interplanetary Tralectories, 21st International Symposium on Space Flight Dynamics, 2009, Toulouse, France, 12 pages.

Mariya Lazebnik et al., A Large-Scale Study of the Ultrawideband Microwave Dielectric Properties of Normal Breast Tissue Obtained From Reduction Surgeries, Phys. Med. Biol. 52, 2007, pp. 2637-2656.

Mariya Lazebnik et al., A Large-Scale Study of the Ultrawideband Microwave Dielectric Properties of Normal, Benign and Malignant Breast Tissues Obtained from Cancer Surgeries, 2007, Physics in, Medicine and Biology, 52, pp. 6093-6115, IOP Publishing, UK.

Mariya Lazebnik et al., Highly Accurate Debye Models for Normal and Malignant Breast Tissue Dielectric Properties at Microwave Frequencies, IEEE Microwave and Wireless Components Letters, vol. 17, No. 12, Dec. 2007, pp. 822-824

Mark Converse et al., A Computational Study of Ultra-Wideband Versus Narrowband Microwave Hyperthermia for Breast Cancer Treatment, IEEE Transactions on Microwave Theory and Techniques, vol. 54, No. 5, May 2006, pp. 2169-2180.

Marta Cavagnaro et al., From Magnetic Resonance Imaging to Dielectric Properties of Tissues, Biophysics & Bioeng. Letters, 2011, vol. 4 (2), pp. 1-8.

Meaney et al., Clinical Microwave Tomographic Imaging of the Calcaneus: A First-in-Human Case Study of Two Subjects, IEEE Transaction on Biomedical Engineering, 2012, pp. 3304-3313.

Natalia K. Nikolova, Microwave Imaging for Breast Cancer, IEEE Microwave Magazine, Dec. 2011, pp. 78-94.

P. Fatourous et al., Use of Magnetic Resonance Imaging for in Vivo Measurements of Water Content in Human Brain: Method and Normal Values, J. Neurosurg 90, Jan. 1999, pp. 109-115.

Paolo Farace et al., An Automated Method for Mapping Human Tissue Permittivities by MRI in Hyperthermia Treatment Planning, Phys. Med. Biol. 42, 1997, pp. 2159-2174.

Qing Huo Liu et al., Active Microwave Imaging I—2-D Forward and Inverse Scattering Methods, IEEE Transactions on Microwave Theory and Techniques, Jan. 2002, pp. 123-133, vol. 50, No. 1.

S. Gabriel et al., The Dielectric Properties of Biological Tissues: II., Measurements in the Frequency Range 10 Hz to 20 GHz, Phys. Med. Biol. 41, 1996, pp. 2251-2269.

S. Gabriel et al., The Dielectric Properties of Biological Tissues: III., Parametric Models for the Dielectric Spectrum of Tissues, Phys. Med. Biol. 41, 1996, pp. 2271-2293.

S. N. Hornsleth et al., A new CT Segmentation Algorithm for Finite Difference Based Treatment Planning Systems, Hyperthermic Oncology, 1996, vol. 2, 521-523.

Susan Rae Smith et al., Dielectric Properties of Low-Water-Content Tissues, Phys. Med. Biol, 1985, vol. 30, No. 9, pp. 965-973.

Thomas Meissner et al., The Complex Dielectric Constant of Pure and Sea Water From Microwave Satellite Observations, IEEE Transactions on Geoscience and Remote Sensing, vol. 42, No. 9, Sep. 2004, pp. 1836-1849.

Uwe Schneider et al., The Calibration of CT Hounsfield Units for Radiotherapy Treatment Planning, Phys. Med. Biol., 41, 1996, pp. 111-124.

Wilfried Schneider et al., Correlation Between CT Numbers and Tissue Parameters Needed for Monte Carlo Simulations of Clinical Dose Distributions, Phys. Med. Biol. 45, 2000, pp. 459-478.

Xu Li et al., An Overview of Ultra-Wideband Microwave Imaging via Space-Time Beamforming for Early-Stage Breast-Cancer Detection, IEEE Antennas and Propagation Magazine, Feb. 2005, pp. 19-34, vol. 47, No. 1.

Yao Xie et al., Multistatic Adaptive Microwave Imaging for Early Breast Cancer Detection, IEEE Transactions on Biomedical Engineering, Aug. 2006, pp. 1647-1657, vol. 53, No. 8.

Zastrow et al., Development of Anatomically Realistic Numerical Breast Phantoms With Accurate Dielectric Properties for Modeling Microwave Interactions With the Human Breast, IEEE Transactions on Biomedical Engineering, 2008, pp. 2792-2800, vol. 55, Issue 12.

(56) References Cited

OTHER PUBLICATIONS

Zhong Qing Zhang et al, Three-Dimensional Nonlinear Image Reconstruction for Microwave Biomedical Imaging, IEEE Transactions on Biomedical Engineering, Mar. 2004, pp. 544-548, vol. 51, No. 3.

USPTO Office Action, U.S. Appl. No. 13/798,428, Dec. 11, 2013, 19 pages.

* cited by examiner

DIELECTRIC ENCODING OF MEDICAL IMAGES

BACKGROUND OF THE INVENTION

The present invention relates generally to microwave medical imaging, and more specifically to displaying resultant images from microwave imaging techniques using different encoding procedures.

Microwave imaging (MWI) techniques utilize non-ionizing radio frequency (RF) energy in the range of 100-10,000 Megahertz (MHz) to generate a complete image of an object. When compared to ionizing radiation, non-ionizing radiation is less costly, requires less specialized environmental protections, and decreases the potential harm to human tissues.

When RF energy moves through a medium such as air and impinges an object, scattering from the object occurs as the RF energy hits the surface and moves through the object to generate a scattering field. Microwave imaging techniques are utilized to measure this scattering field and, combined with other information about an object, reconstruct the image of the object that created the measured scattering field. The reconstructed image can be used to provide diagnoses of the human body.

SUMMARY

During the microwave imaging process, radio frequency scattering information is collected and the collected information is then input into a computing environment such that the radio frequency scattering information can be reconstructed into a dielectric image that can be disseminated to a wide audience. The current dielectric images are unfamiliar to clinicians and diagnosticians. A cost effective approach is to encode dielectric images into other familiar forms so additional training, diagnostic hardware, or software is not required.

A microwave image processing system and method is presented wherein a microwave image capture device is configured to receive a first plurality of scattered microwave signals from an object or a plurality of objects. A computing environment within the microwave image processing system is in communication with the microwave image capture device for receiving the first plurality of scattered microwave signals and converting the first plurality of scattered microwave signals into a dielectric image. A viewing location within the microwave image processing system is capable of receiving and displaying the dielectric image. The computing environment is capable of determining permittivity and conductivity values of an object and the location of the object. The permittivity and conductivity values forming the image of the object can be manipulated to form a dielectric encoded image. Furthermore, the computing environment is capable of establishing a relationship at microwave frequencies with a characteristic of tissue associated with the human body. Within an embodiment presented herein, dielectric images and/or encoded dielectric images are presented in DICOM format. The computing environment is configured to convert encoded dielectric images into Hounsfield encoded images and/or MRI intensity encoded images. Within an embodiment presented herein, Hounsfield encoded images and/or MRI intensity encoded images are presented in DICOM format. Furthermore, in an embodiment, the computing environment is configured to convert Hounsfield encoded images to dielectric images.

BRIEF DESCRIPTION OF THE DRAWINGS

An embodiment will now be described in more detail with reference to the accompanying drawings, given only by way of example, in which.

BRIEF DESCRIPTION OF THE TABLES

Table I shows a list of tissues selected to span the entire Hounsfield unit range and the corresponding Hounsfield unit range for each tissue.

Table II shows the tissue types presented in Gabriel and colleagues (1996) and the tissue types utilized in certain embodiments.

Table III shows the tissue types presented in Gabriel and colleagues (1996) that are utilized in certain embodiments and their corresponding four-pole Cole-Cole parameters.

Table IV shows an example of initial values of w, c1, and c2 within an ACPSO algorithm used for determining Debye parameters according to an embodiment.

Table V shows Debye parameters that have been generated according to an embodiment arranged in ascending order, according to the parameter, eps S.

Table VI shows a reduced number of tissues, utilized in an embodiment, with their corresponding one-pole Debye parameters.

Table VII shows the one-pole Debye parameters and other data for a reduced amount of tissues, generated according to an embodiment.

DETAILED DESCRIPTION OF THE INVENTION

Figure 1:
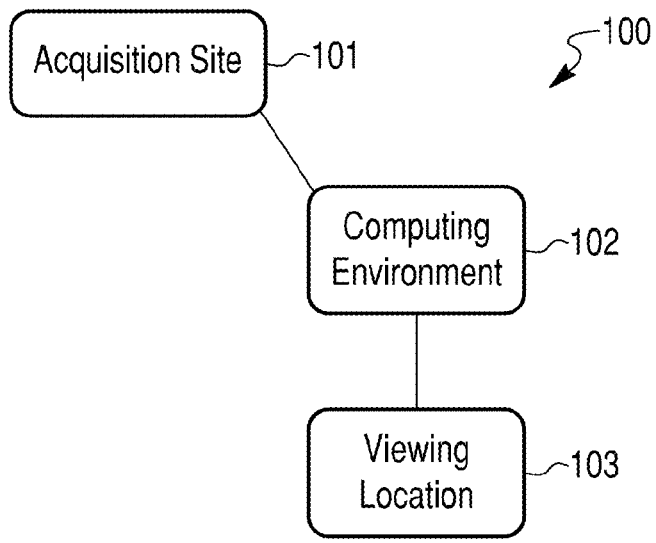
FIG. 1 is a simplified block diagram showing an overview of the present microwave image processing system.

FIG. 1 shows an overview of the present image processing system 100. In an embodiment, image processing system 100 is configured to process microwave signals. The present system 100 allows for removal of the computationally expensive task of image reconstruction from an image acquisition site 101, and from a viewing location 103. Image reconstruction is handled by a computing environment 102 that is specifically configured to quickly reconstruct microwave images. Additional detail of microwave image processing components, processes, and techniques is set forth in U.S. patent application Ser. No. 13/798,428 filed Mar. 13, 2013 whose entire contents are incorporated herein by reference for components, processing, and techniques related to microwave imaging. The algorithms described herein may be stored in a computer-readable storage medium (any type of memory). The algorithms and conversions performed herein may be performed in an automated manner, that is, without manual intervention and without the necessity to perform any part of the process manually.

The acquisition site 101 can be in a hospital, a radiology group, a doctor's office, a medical imaging facility, or other site with a microwave image data capture device. A computer with network capabilities is also located at the acquisition site 101. In an embodiment, after microwave signals have been captured, the data is transmitted to the computing environment 102 for reconstruction of the image. Upon completion of reconstruction, the images can be stored in a centralized reconstruction database within the computing environment 102 where the images can be accessed by a variety of stakeholders for viewing at the viewing location 103. In other embodiments, the acquisition site 101 can be any site with a computed tomography image data capture device or can be any site containing already generated computed tomography image data.

In most embodiments, the computing environment 102 is located remote from acquisition site 101 and viewing location 103 or as an alternative, the computing environment 102 is located in the same room with acquisition site 101 and viewing location 103. In some embodiments, the computing environment 102 is located many miles away (for example more than 10 or more than 100 miles away) from acquisition site 101 and viewing location 103. However, in certain applications of the invention, "remote" as used herein can mean in a different room or in a different building.

The computing environment 102 contains hardware and software necessary to carry out reconstruction of microwave images. In an embodiment, computing environment 102 contains multiple processors which employ parallel computing techniques to reconstruct RAW dielectric images. The processors within computing environment 102 can be single or multicore processors. A processing queue within computing environment 102 can provide MWI data from on-board memory modules to multiple processors in order to support parallel operations by the processors during reconstruction of images. The computing environment 102 further contains a centralized database of prior raw microwave data along with the resulting calculated images and other information previously calculated for the acquisition sites 101. This centralized database is a significant feature because it includes raw data (and calculated images and other information) from a plurality of acquisition sites 101 (for example, 10 or more sites or 100 or more sites) and thus the processing for an individual site 101 is able to take advantage of prior calculations done for all of the sites in the system 100. In an embodiment, reconstruction of a microwave image is an iterative process which requires a seed (an educated guess as to the electrical properties of the subject patient) as a starting point. The use of prior results from calculations done for all of sites 101 results in a better seed, and thus a substantial reduction in computing. The centralized database may also collect the images and resulting diagnosis from all of the sites in the distributed system, which results in a more informed automated diagnostic algorithm.

A benefit of the present system 100 is providing users with complete images of the human body in sufficient detail as to render a timely and accurate medical diagnosis by trained medical professionals. A doctor or other medical professional or scientist performing research can access the computing environment 102 from viewing location 103 or viewing locations, in order to view reconstructed images, diagnose the patient, and submit a report on the patient. A patient can access the computing environment 102 from viewing location 103, in order to view reconstructed images, review the patient's history, and provide updates to the patient's personal information. The present system 100 preferably includes a Digital Imaging and Communications in Medicine (DICOM) communications application to communicate with researchers in an industry standard format. Insurance companies can access and communicate with the system via viewing location 103 that includes a Data Collaboration application that provides for communications in insurance industry standards.

In an embodiment, dielectric images are converted to dielectric encoded images, Hounsfield encoded images, and/or MRI intensity images. The Hounsfield encoded images, MRI intensity images, and/or dielectric encoded images can be accessed at any time by the computing environment 102. In another embodiment, CT images are Hounsfield encoded and then converted to dielectric images and/or dielectric encoded images. These images are made available for viewing at the viewing location 103 by a web-based MWI viewing software application.

Figure 2:
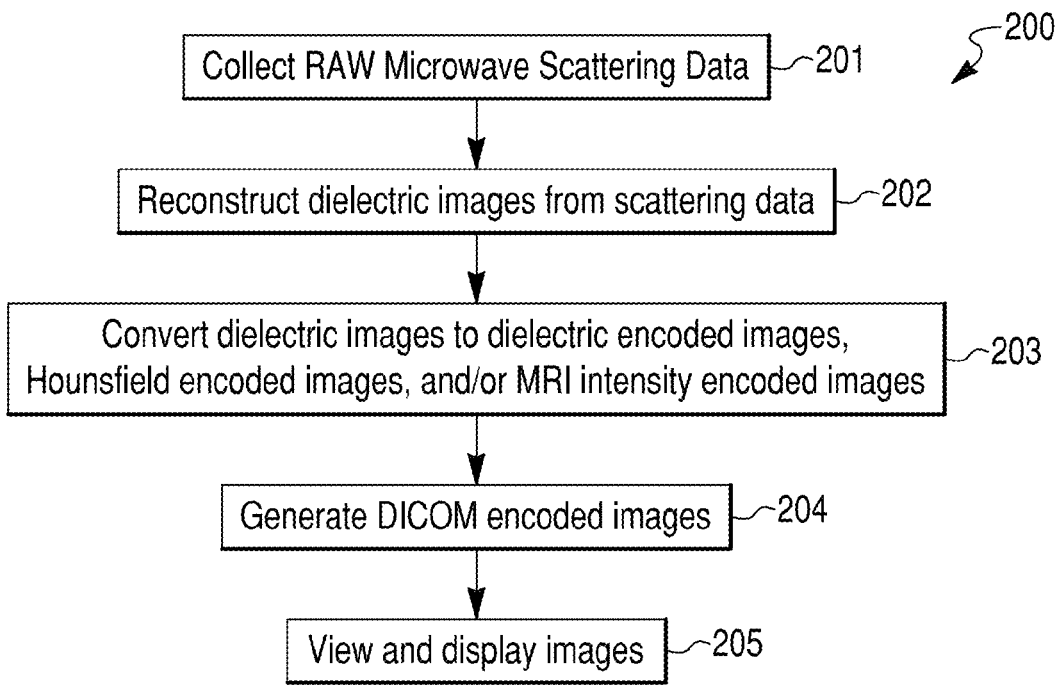
FIG. 2 is a flow chart showing an overview of the image reconstruction and conversion process of the present microwave image processing system.

FIG. 2 is a flow chart 200 showing an embodiment of the image reconstruction process and image conversion process of the present image processing system 100. In step 201, raw microwave image scattering data is captured by scanning all or part of a patient's body with an image capture device. An image capture device, within acquisition site 101, impinges electromagnetic radiation upon the patient, and the scattered electromagnetic radiation is collected by a series of antennas (or receivers) arranged within the image capture device. The image capture device is preferably a full body scanner that uses non-ionizing frequencies, such as microwaves, to image the body. Ionizing frequencies have been shown to have cancer causing effects, increased costs associated with their use, and require specialized environmental protections. The non-ionizing microwaves used by the image capture device are preferably in the range of 100-10000 Megahertz (MHz).

At the acquisition site 101, information identifying the patient is attached to the raw microwave image (MWI) data (complex permittivity data). Information regarding the configuration of the microwave image data capture device is also attached to the MWI data. The raw MWI data is then uploaded to the computing environment 102 for processing. At the computing environment 102, the image is reconstructed from the measured scattering field in step 202. Various reconstruction techniques are described in Matteo Pastorino, Microwave Imaging, Wiley, 1st edition, 2010. The entire contents of this publication is incorporated herein by reference for the microwave reconstruction techniques described therein; however, other reconstruction techniques may be used. In step 203, at the computing environment 102, the reconstructed images are converted to dielectric encoded images, Hounsfield encoded images, and/or MRI intensity images. In step 204, if necessary, the images from step 203 are converted into the DICOM (Digital Imaging and Communications in Medicine) format. DICOM is an industry standard file formatting structure that governs the exchange of medical information between a variety of acquisition sites 101. In step 205, a display of the resultant images occurs at viewing location 103.

After reconstruction of raw microwave signals, it is useful to format raw dielectric images in a way to allow for an efficient exchange of information with current diagnostic tools. Furthermore, it is advantageous to provide microwave images in a format that does not require physicians and radiologists to learn how to use an unfamiliar image. Hounsfield encoded imaging studies and MRI intensity encoded imaging studies are display outputs that are familiar to most medical imaging professionals.

Figure 3:
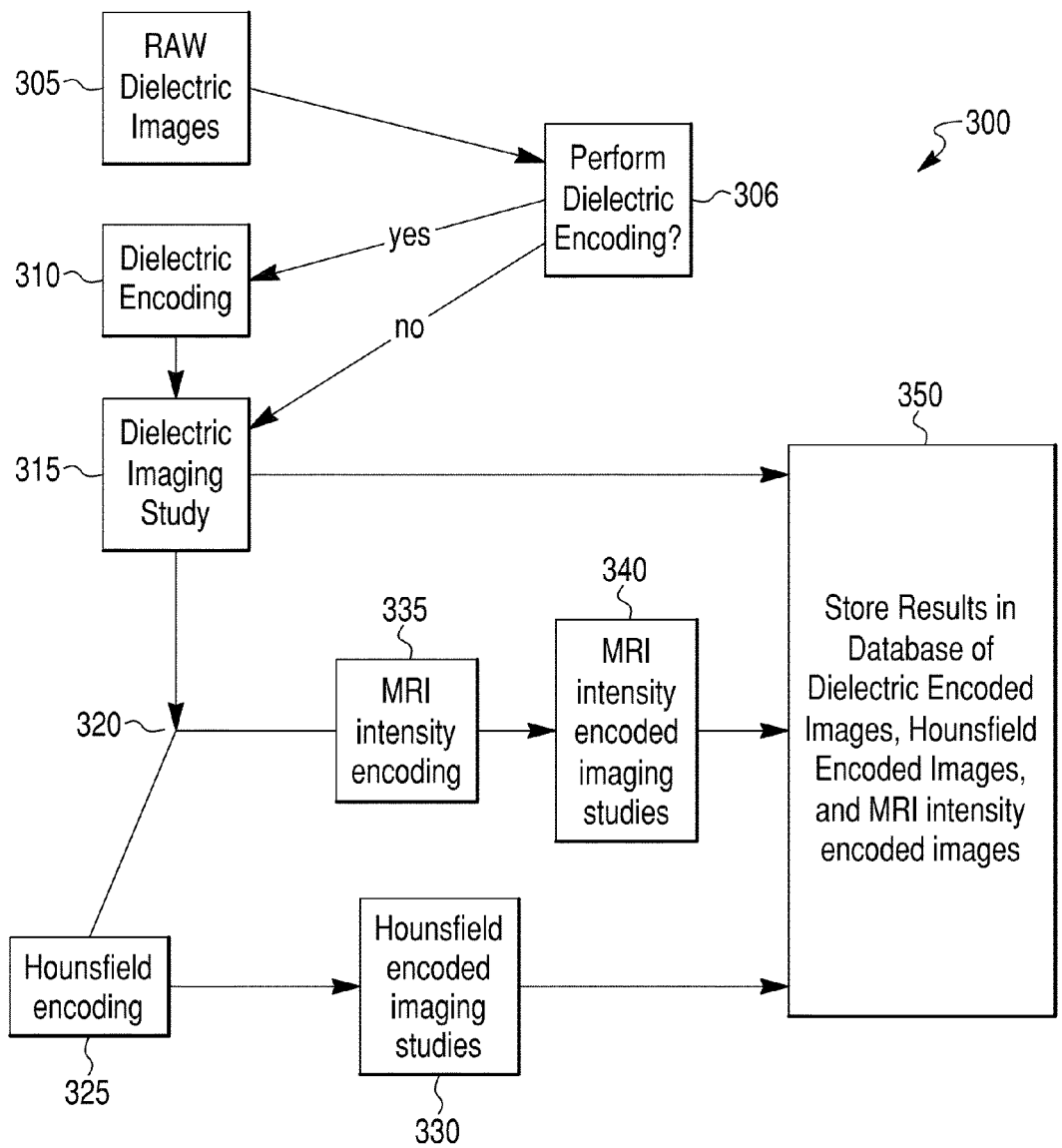
FIG. 3 is a flow chart of exemplary steps used in the conversion of RAW dielectric images into Hounsfield encoded images or MRI intensity encoded images.

FIG. 3 is a flow chart 300 of exemplary steps used in the conversion of RAW dielectric images into Hounsfield encoded images and/or MRI intensity encoded images. In step 305, the RAW dielectric imaging study has been reconstructed by computing environment 102 based on the raw microwave image scattering data collected by the image capture device at acquisition site 101. When reconstructing a RAW dielectric image of an object, computing environment 102 uses the recorded electromagnetic fields at acquisition site 101 and algorithms to form permittivity and conductivity values of the object and determine the location of the object that the electromagnetic waves had impinged.

Permittivity describes a material's response to an electric field and generally depends on the frequency of the field. The frequency dependence reflects the fact that a material's polarization does not respond instantaneously to an applied field. Permittivity is often treated as a complex function of the angular frequency $\omega$ of the applied field. It is natural to separate the complex permittivity into real and imaginary parts.

$$\in(\omega) = \in'(\omega) + i^* \in''(\omega)$$

Where $\in'$ is the real part of the permittivity and $\in''$ is the imaginary part of the permittivity. A RAW dielectric image can be envisioned as the complex permittivity split into the real and imaginary parts. However, it is also possible to define the imaginary permittivity in terms of the conductivity $\sigma$ $$\sigma = -w \in'' \in_0$$

Where $\in_0$ is the vacuum permittivity. Note that the angular frequency is defined as $w = 2\pi f$ where f is the frequency in Hz.

Flow chart 300 utilizes previously published data about dielectric properties of human tissues. Dielectric properties of human tissues can be measured using, for example, a vector network analyzer and dielectric probe kit. In addition, dielectric properties that others have measured can be found in the literature. Dielectric properties of human tissues vary depending on the frequency used. Measurements of dielectric properties are often fitted to a Cole-Cole model. For example, Gabriel and colleagues in 1996 fit a four-pole Cole-Cole model using the dielectric properties for numerous tissues (Gabriel, C., S. Gabriel, and E. Corthout. The dielectric properties of biological tissues: I. Literature survey. Physics in Medicine and Biology, vol. 41, no. 11, pp. 2231-2249, 1996 and Gabriel, S., R. W. Lau, and C. Gabriel. The dielectric properties of biological tissues: II. Measurements in the frequency range 10 Hz to 20 GHz. Physics in Medicine and Biology, vol. 41, no. 11, pp. 2251-2269, 1996 and Gabriel, S., R. W. Lau, and C. Gabriel. The dielectric properties of biological tissues: III. Parametric models for the dielectric spectrum of tissues. Physics in Medicine and Biology, vol. 41, no. 11, pp. 2271-2293, 1996). The entire contents of these publications are incorporated herein by reference for the techniques and data disclosed therein related to dielectric properties of tissues. The Gabriel (1996) database represents dielectric values for a large range of tissues incorporated within the human body and has been utilized in various embodiments presented herein. A four-pole Cole-Cole model as used in the Gabriel (1996) database is:

$$\varepsilon(\omega) = \varepsilon_\infty + \sum_{i=1}^{4} \frac{\Delta \varepsilon_i}{1 + (j\omega\tau_i)^{(1-\alpha_i)}} + \frac{\sigma_s}{j\omega\varepsilon_0}$$

Returning to FIG. 3, at step 306, a decision is made automatically by computing environment 102 or manually by a user whether to perform dielectric encoding on the RAW dielectric images. Depending on the type of image capture device used or the particular collection parameters established for collecting the raw microwave scattering data, some processing or encoding of the RAW dielectric images may be required before the images can be converted to a desired output format (i.e. Hounsfield units or MRI intensity encoded images). In an embodiment, a user or the computing environment 102 chooses to perform dielectric encoding of the RAW dielectric images in step 310. In an embodiment, the RAW dielectric images are encoded into a different set of dielectric values termed MAC units in step 310. In medical imaging applications, MAC units relate a characteristic of the tissue at microwave frequencies within the object being imaged and/or aid in the display of the image. In an embodiment, the underlying dielectric values of tissues are related to the density of the tissues within the object being imaged. In another embodiment, the MAC units involve an algebraic manipulation of the dielectric image to allow for ease of use with DICOM files and viewing of the image on a computer. In general, dielectric encoding is utilized in step 310 to convert the complex permittivity, which is defined by the pixel values obtained in the RAW dielectric image, to another form to establish a relationship with an underlying characteristic of the tissue at microwave frequencies. In an embodiment a user or the computing environment 102 may choose to forgo dielectric encoding and proceed directly to the dielectric imaging study in step 315.

During the dielectric imaging study of step 315, images (RAW dielectric images or dielectric encoded images) are formatted into the DICOM (Digital Imaging and Communications in Medicine) format. Once the dielectric imaging study is complete, the DICOM formatted images can be stored within the centralized database of the computing environment 102 at step 350.

A user or the computing environment 102 can also decide at step 320 to continue processing the DICOM formatted dielectric image based on a desired output imaging format.

In an embodiment, a user or the computing environment decides, at step 320, the desired output imaging format is a Hounsfield image which can be used in Computed Tomography (CT) studies. In step 325, Hounsfield encoding is performed. Hounsfield encoding relates the dielectric encoded values (MAC units) or the RAW dielectric values of the image to an appropriate Hounsfield value. Hounsfield values can be used in Computed Tomography (CT) studies. Hounsfield encoding is a method of encoding pixel values that are related to the underlying density of the tissues being measured. Hounsfield units for different tissues can be found in the literature or calculated by computing them from linear attenuation coefficients (or mass attenuation coefficients times the density to give the linear attenuation coefficients). By determining the Hounsfield unit ranges for representative tissues in the human body, a method for converting from dielectric encoded images to Hounsfield encoded images is developed. CT images are not always contained directly in Hounsfield units. Thus it may be necessary to use the RescaleIntercept and RescaleSlope found in the DICOM header file of the CT image to convert to Hounsfield units.

In step 330, a DICOM formatted imaging study is performed on the Hounsfield encoded images to create DICOM formatted Hounsfield encoded images. The DICOM formatted Hounsfield encoded images can be stored in a centralized database in step 350. The rational for Hounsfield encoding and DICOM formatting is to allow for the efficient exchange of information that was created using microwave techniques with current diagnostic tools and medical techniques. Additionally, the medical community is familiar with diagnosing Hounsfield imaging studies and hence physicians will require little if any retraining to use the output of the present microwave imaging process.

In an embodiment, a user or the computing environment decides, at step 320, the desired output imaging format is an MRI intensity encoded image. At step 335, MRI intensity encoding is performed. MRI intensity encoding relates the dielectric encoded values (MAC units) or RAW dielectric values of the image to an MRI signal intensity value. MRI signal intensity values are used in Magnetic Resonance Imaging studies and are representative of the water content of the object being measured. Typically, different tissues have different water content.

An MRI image can be thought of as numerous signal intensity values. Each signal intensity value can be represented as a complicated function of various parameters such as the contrast-determining tissue parameter, proton density, T1 and T2, and the machine parameters TR and TE. Unlike a CT image, there is no standard reference signal for MRI and the operator has a high degree of control of how the signal intensities of various structures vary in the images by using different MRI methods and imaging parameters. A spin-echo MRI sequence is one that is widely used which has the equation $$I = k\alpha\rho e^{-\frac{TE}{T2}} \left( 1 - 2e^{-\frac{TR-\frac{TE}{2}}{T1}} + e^{-\frac{TR}{T1}} \right)$$

Where ρ is the proton density, TR is the repetition time of the RF pulse, TE is the echo time of the signal, T1 is the longitudinal relaxation time constant, T2 is the transversal relaxation time constant, I is the intensity of the signal, and α is a nonuniformity factor.

In step 340 of FIG. 3, a DICOM formatted imaging study is performed on the MRI intensity encoded images to create DICOM formatted MRI intensity encoded images. The DICOM formatted MRI intensity encoded images can be stored in a centralized database in step 350.

In some embodiments, storing results in the centralized database at step 350 does not necessarily have to occur at the same time and each individual imaging study from steps 315, 340, and 330 can be sent to the centralized database at separate times if needed.

The Hounsfield encoded images, MRI intensity images, and/or dielectric encoded images can be accessed at any time within the centralized database by a user or the computing environment 102. These images can be made available for viewing at the viewing location 103 by a web-based MWI viewing software application. The MWI viewing application allows for selected viewing of reconstructed images by doctors, medical professionals, research scientists and patients. At this point, the appropriate Clinician(s) and/or Diagnostician(s) can create a report of their diagnostic finding using a MWI Patient Reporting application. The Hounsfield encoded images, MRI intensity images, and/or dielectric encoded images presented herein will support an industry standard data exchange with researchers, hospitals, and clinics.

Figure 4:
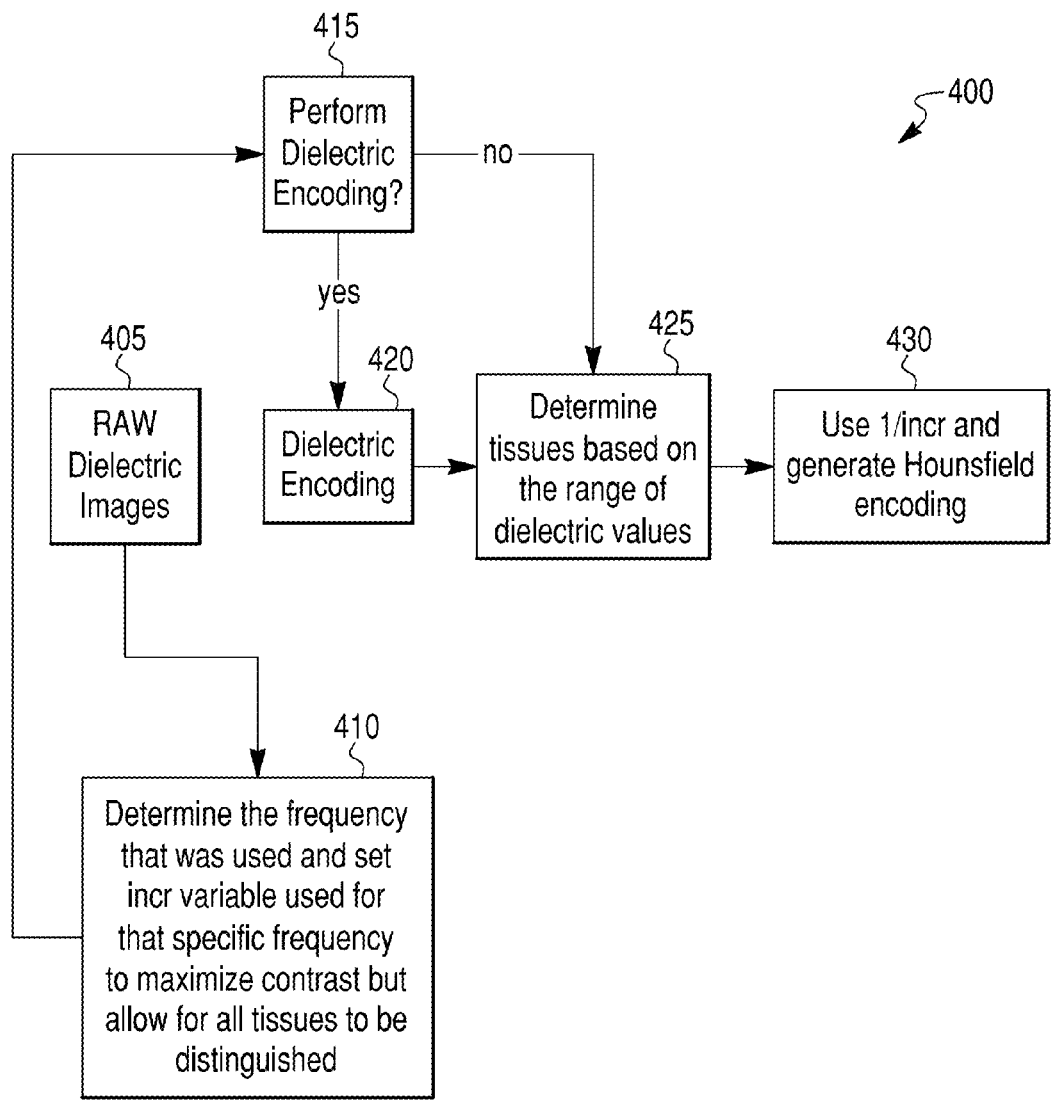
FIG. 4 is a flow chart of exemplary steps used in the conversion of RAW dielectric images into Hounsfield encoded images for a specific frequency.

FIG. 4 is a flow chart 400 of exemplary steps used in the conversion of RAW dielectric images at a specific frequency of interest into Hounsfield encoded images. This process can be repeated for other frequencies of interest. In step 405, RAW dielectric values reconstructed from microwave scattering data collected at acquisition site 101 to form an image at a specific frequency are presented. In step 410 it is determined what frequency the RAW dielectric values fall into (if not already known). In addition, the appropriate incr variable is determined for the frequency. The incr variable is designed to be different for each tissue at different frequencies and to maximize the contrast between tissues such that all tissues can be distinguished. Examples of use of increment variables will be discussed below in connection with Tables I and VII. At step 415, a decision is made automatically by computing environment 102 or manually by a user whether to perform dielectric encoding on the RAW dielectric images. Should a decision be made to proceed with dielectric encoding, the RAW dielectric values are dielectric encoded at step 420. The dielectric encoding at step 420 involves converting the RAW dielectric images to MAC units to relate a characteristic of the tissue at microwave frequencies to the image and/or aid in the display of the image. In an embodiment, the underlying dielectric values of the tissue are related to the density of the tissue. In another embodiment, the MAC units involve an algebraic manipulation of the dielectric image to allow for ease of use with DICOM files and viewing of the image on a computer. For example, algebraic manipulation of the data can be performed to improve contrast between different tissues when viewing the image. Should a user or the computing environment 102 choose to forgo dielectric encoding, the presented process proceeds directly to step 425. In step 425, the tissues present in each pixel are determined by looking at the range of the dielectric values each pixel value falls into. In step 430 the appropriate 1/incr value for the tissue at the given frequency is used and then the dielectric image becomes Hounsfield encoded.

Figure 5:
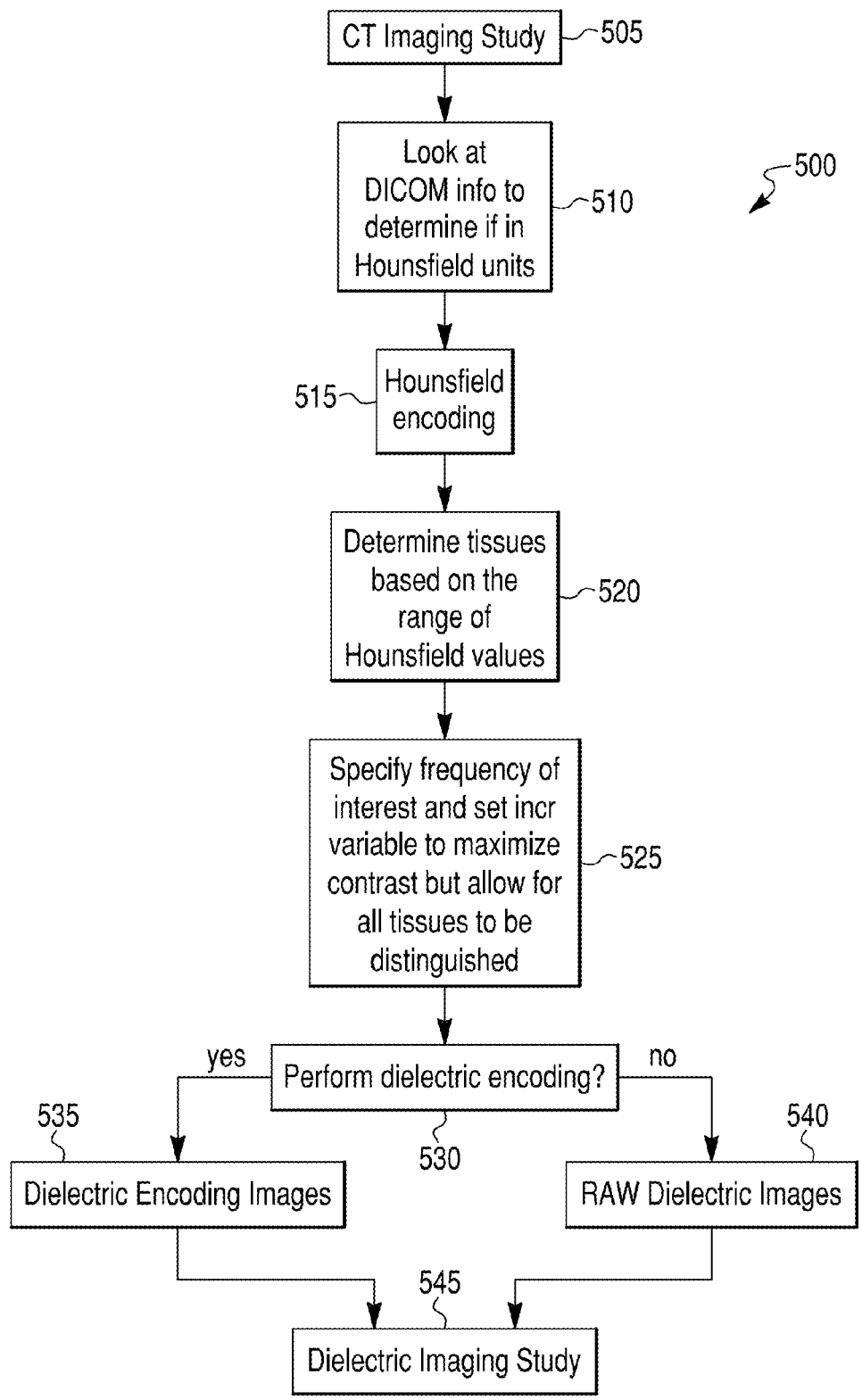
FIG. 5 is a flow chart of exemplary steps used in the conversion of CT images into RAW dielectric images for a specific frequency.

In certain embodiments, it is beneficial to convert from Hounsfield units present in a CT image to dielectric values. FIG. 5 is a flow chart 500 of exemplary steps used in the conversion of a CT image into a RAW dielectric image at a specific frequency of interest. This process can be repeated for other frequencies of interest. In step 505, a CT image from acquisition site 101 is presented. In step 510, the DICOM info is looked at to determine if the CT image is already in Hounsfield units. If the CT image is not in Hounsfield units, computing environment 102 converts the image to Hounsfield units through the Hounsfield encoding procedure established at step 515. In step 520, the tissues present in each pixel in the image are determined based on the range of the Hounsfield values. These tissues were assigned a Hounsfield unit range based on searching literature, selecting tissues representative of the human body, and Hounsfield units that agreed across references. There are 4096 different Hounsfield Units which typically range from −1000 to +3095. The 4096 Hounsfield units have been fit into ranges where each range is representative of a certain type of tissue. In the example presented in Table I, 30 tissues, not including air and water, were investigated based on the database by Gabriel and colleagues in 1996, hence a range for each Hounsfield unit is associated with each specific tissue used for the dielectric values. The process described is not limited to these 30 tissues and can be established for any number of tissues within the human body. The data set forth in the Tables herein can be refined as additional and/or more accurate data becomes available. The Gabriel database was selected for the example calculation present below due to its completeness and consistency which allows for certain embodiments to be illustrated most readily.

In step 525, a specific frequency is specified. This frequency determines the incr variable which is designed to be different for each tissue at different frequencies and to maximize the contrast between tissues such that all tissues can be distinguished. In an embodiment, each tissue was assigned a real permittivity increment based on examining the real permittivity of the tissues at 300 MHz. This real permittivity increment is designed to be changed depending on the frequency of interest. This real permittivity increment was selected so that a unique dielectric value corresponds to every Hounsfield unit. Table I shows the tissues selected, their Hounsfield unit ranges (CT number) selected, the complex permittivity of each tissue, and the real permittivity increment for each tissue used at 300 MHz. The specific frequency of 300 MHz was chosen as the frequency for an exemplary investigation due to its presence at the lower end of the microwave frequency range where the potential health and environmental impacts of a medical procedure utilizing such a frequency are minimized. Other frequencies that could be used within the present methods would include those in the range from 100 MHz to 10 GHz.

At step 530, a decision is made whether to perform dielectric encoding on the Hounsfield encoded images. Should a decision be made to proceed with dielectric encoding, the Hounsfield encoded images are converted to dielectric encoding at step 535. The dielectric encoding at step 535 can involve converting the Hounsfield encoded images to MAC units which relate to a specific characteristic of the tissue at microwave frequencies and/or aid in the display of the image. In an embodiment, the underlying dielectric values of the tissue are related to the density of the tissue. In another embodiment, the MAC units involve an algebraic manipulation of the dielectric image to allow for ease of use with DICOM files and viewing of the image on a computer. At step 540, a Hounsfield encoded image is converted to RAW dielectric images. In step 545 dielectric encoded images and/or RAW dielectric images can be converted into the DICOM format which forms the dielectric imaging study.

Figure 7:
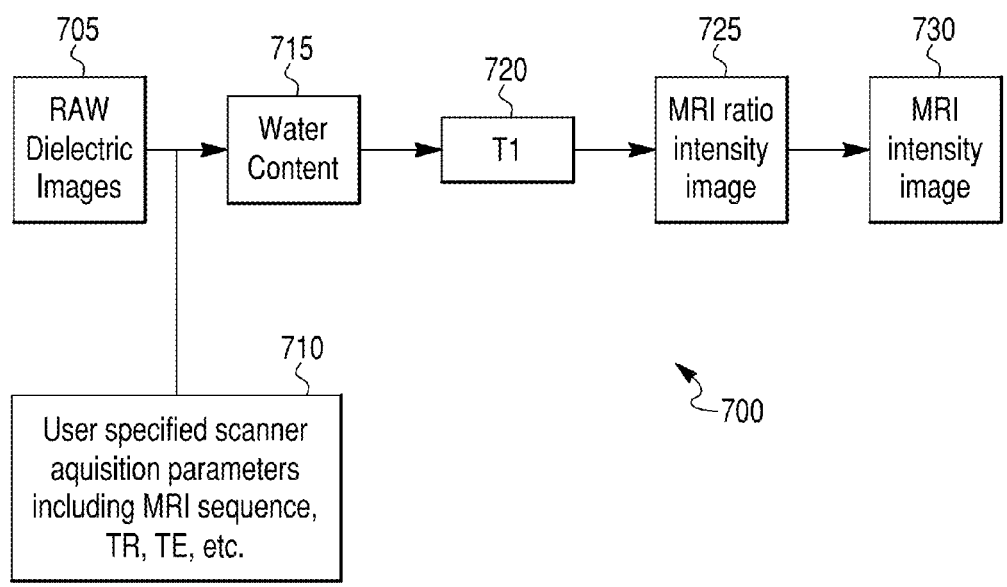
FIG. 7 is a flow chart of exemplary steps used in the conversion of RAW dielectric images to MRI intensity encoded images for a specific frequency.

In certain embodiments, it may be necessary to convert RAW dielectric images to MRI intensity images. FIG. 7 is a flow chart 700 of exemplary steps used in the conversion of a RAW dielectric image to a MRI intensity encoded image. In step 705, RAW dielectric values which have been reconstructed from microwave scattering data in computing environment 102 which was collected at acquisition site 101 forming an image at a specific frequency are presented. In step 710, the user or computing environment 102 specifies specific MRI scanner acquisition parameters such as the MRI sequence, repetition time, and echo time to use in forming the MRI intensity image. In step 715, a water content map is created from the RAW dielectric values. In step 720, a T1 map is created from the water content. In step 725, an MRI ratio intensity image is created using the user specified MRI parameters established in step 710. In step 730, the MRI ratio intensity image is converted to a single MRI intensity image. In an embodiment, it is also possible to specify different repetition times to create different looking MRI intensity images. Hence, the process described in FIG. 7 can be used to create different MRI intensity images from the same RAW dielectric image.

Figure 6:
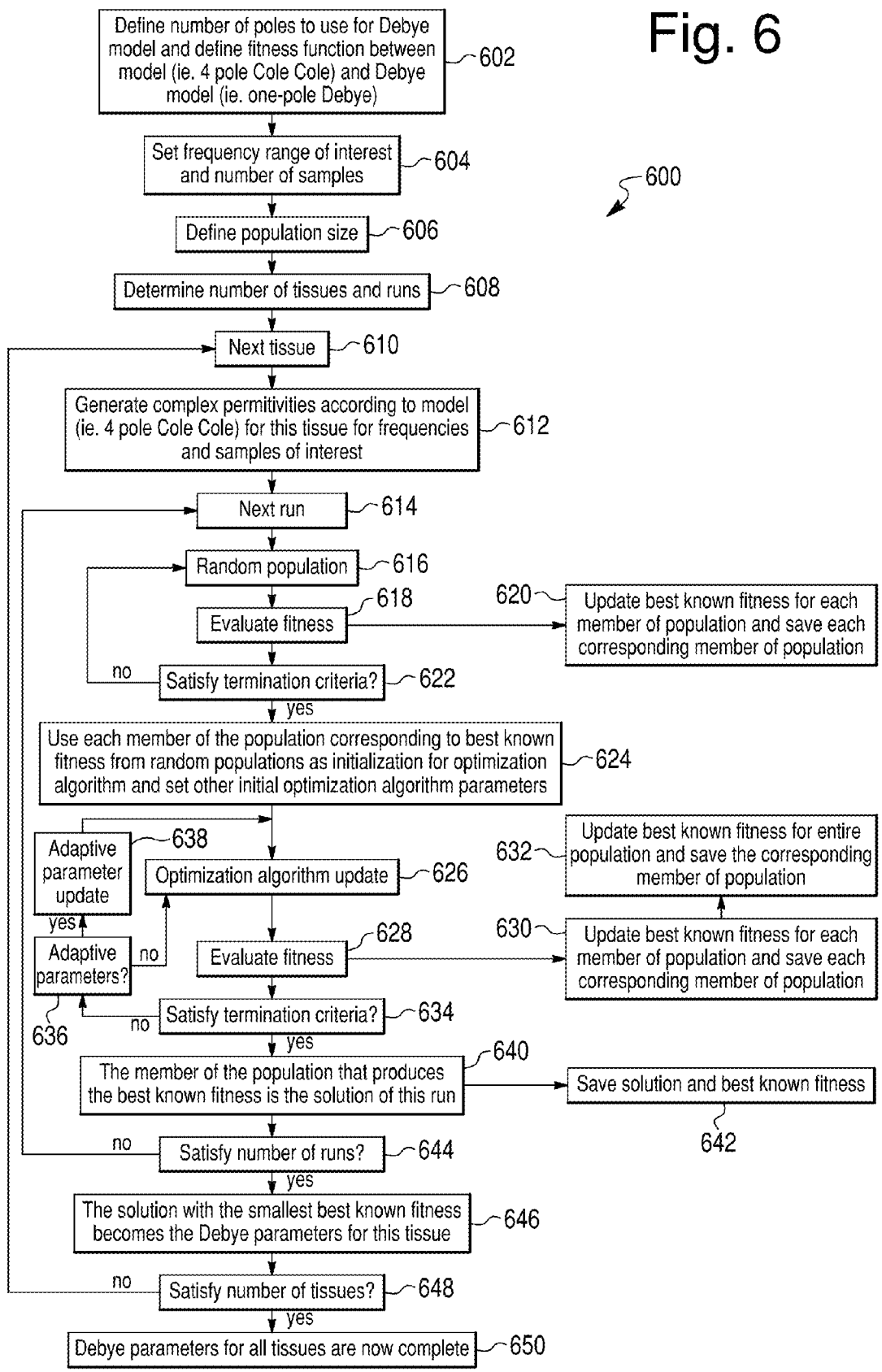
FIG. 6 is a flow chart of exemplary steps used in a process for generating Debye parameters using an extended random initialization scheme in conjunction with an optimization algorithm that can be adaptive.

FIG. 6 is a flow chart 600 of exemplary steps used in an embodiment for generating Debye parameters using an extended random initialization scheme with an optimization algorithm that can be adaptive for multiple runs over multiple tissues. Furthermore, FIG. 6 describes an embodiment to generate one-pole Debye parameters for a particular tissue in question when compared to a four-pole Cole-Cole model. A fitness function (also known as a cost function or objective function) as later defined can be used to minimize the difference between the Debye model and four-pole Cole-Cole model. An extended random initialization scheme, or other similar schemes, along with an optimization algorithm which can be adaptive can be used for several runs for each tissue in the minimization process to determine optimal Debye parameters for all tissues of interest.

Flow chart 600 utilizes previously known data about dielectric properties of human tissues. As mentioned previously, dielectric properties of human tissues vary depending on the frequency used. Measurements of dielectric properties are often fitted to a Cole-Cole model. The addition of the $\alpha_i$ parameters in the Cole-Cole model causes difficulty when transforming to the time domain because the fractional powers of frequency lead to fractional derivatives. Due to this difficulty, using the Cole-Cole model directly in finite difference time domain (FDTD) codes is problematic. Hence, the Cole-Cole model is often converted (and replaced) with a Debye model. The multi-pole Debye equation is $$\varepsilon(\omega) = \varepsilon_\infty + \sum_{i=1}^{n} \frac{\Delta \varepsilon_i}{1 + j\omega\tau_i} + \frac{\sigma_s}{j\omega\varepsilon_0}$$

A Cole-Cole or Debye model allows for a wide number of frequencies to be defined to generate a frequency-dependent model which can be used in converting dielectric encoded images to Hounsfield encoded images or MRI encoded images. Examples of these type of calculations will be described in more detail later. In an embodiment a one-pole Debye model is used. Other embodiments can use a higher number of poles for the Debye model or use other models such as the Cole-Cole model.

Continuing with flow chart 600, in step 602, the user defines the number of poles to use for the Debye model. In an embodiment, one-pole has been selected for sample calculations described below. The user can also define in step 602 a fitness function between the model of interest (i.e. four-pole Cole-Cole) and the Debye model. An example of a fitness function used in an embodiment is described in more detail later. In step 604, the user defines the frequency range of interest for the tissues and the number of samples (number of frequencies used). In step 606, the population size to be used by the optimization process is defined. In step 608, the number of tissues and number of runs is defined by the user. In step 610, the next tissue is used (the iterative process starts with the first tissue and then proceeds later to the last tissue). In step 612, complex permittivity values from the model of interest (i.e. four-pole Cole-Cole) are generated for all frequencies in the range used. In step 614, the next run is used.

Steps 616-622 constitute an extended random initialization scheme. In step 616, a random population is generated. In step 618, the fitness of each member of the population is evaluated. In step 620, the best known fitness for each member of the population is updated and each corresponding member of the population is saved. In step 622, a termination criteria is checked (in an embodiment the termination criteria is a user defined number of iterations). If the termination criterion is satisfied the algorithm proceeds to step 624 otherwise it repeats from step 616. Steps 624-642 constitute an optimization algorithm that can be adaptive. The optimization algorithm may be based on adaptive chaotic particle swarm optimization (ACPSO), other classic gradient based optimization methods or other metaheurstic algorithms such as the genetic algorithm or simulated annealing. In step 624, the result of the extended random initialization scheme is used as the initialization for the optimization algorithm. In addition, in step 624 other optimization algorithms parameters are initialized. In step 626, the optimization algorithm is updated. In step 628, the fitness is evaluated. In step 630, the best known fitness for each member of the population is updated and each corresponding member of the population is saved. In step 632, the best known fitness for the population is updated and the corresponding member of the population is saved. In step 634, the termination criteria is checked (in an embodiment, the termination criteria is the number of iterations for the optimization algorithm). If the termination criteria is satisfied the algorithm proceeds to step 640. If the termination criteria is not satisfied a check is made in step 636 to determine if adaptive parameters need to be updated. If adaptive parameters need to be updated they are done so in step 638 and then the algorithm proceeds again from step 626. If adaptive parameters are not updated the algorithm proceeds again from step 626. In step 640 the member of the population that produced the best known fitness becomes the solution of the current run. In step 642 this solution and best known fitness is saved. In step 644 termination criteria is checked (in an embodiment, three runs are used). If the number of runs is satisfied then the algorithm proceeds with step 646 otherwise the algorithm repeats from step 614. In step 646, the solution with the smallest best known fitness for all runs becomes the Debye parameters for the current tissue. In step 648, the termination criterion is checked (in an embodiment, the termination criteria is 27 total tissues not including water). If the termination criteria is satisfied the algorithm proceeds to step 650, otherwise the algorithm repeats from step 610. In step 650, the algorithm completes and the Debye parameters that produce a minimum (in terms of the fitness function) when compared to the original model (i.e. four-pole Cole-Cole) for all tissues are successfully generated. Debye parameters generated according to an embodiment are displayed in Table V.

Figure 17:
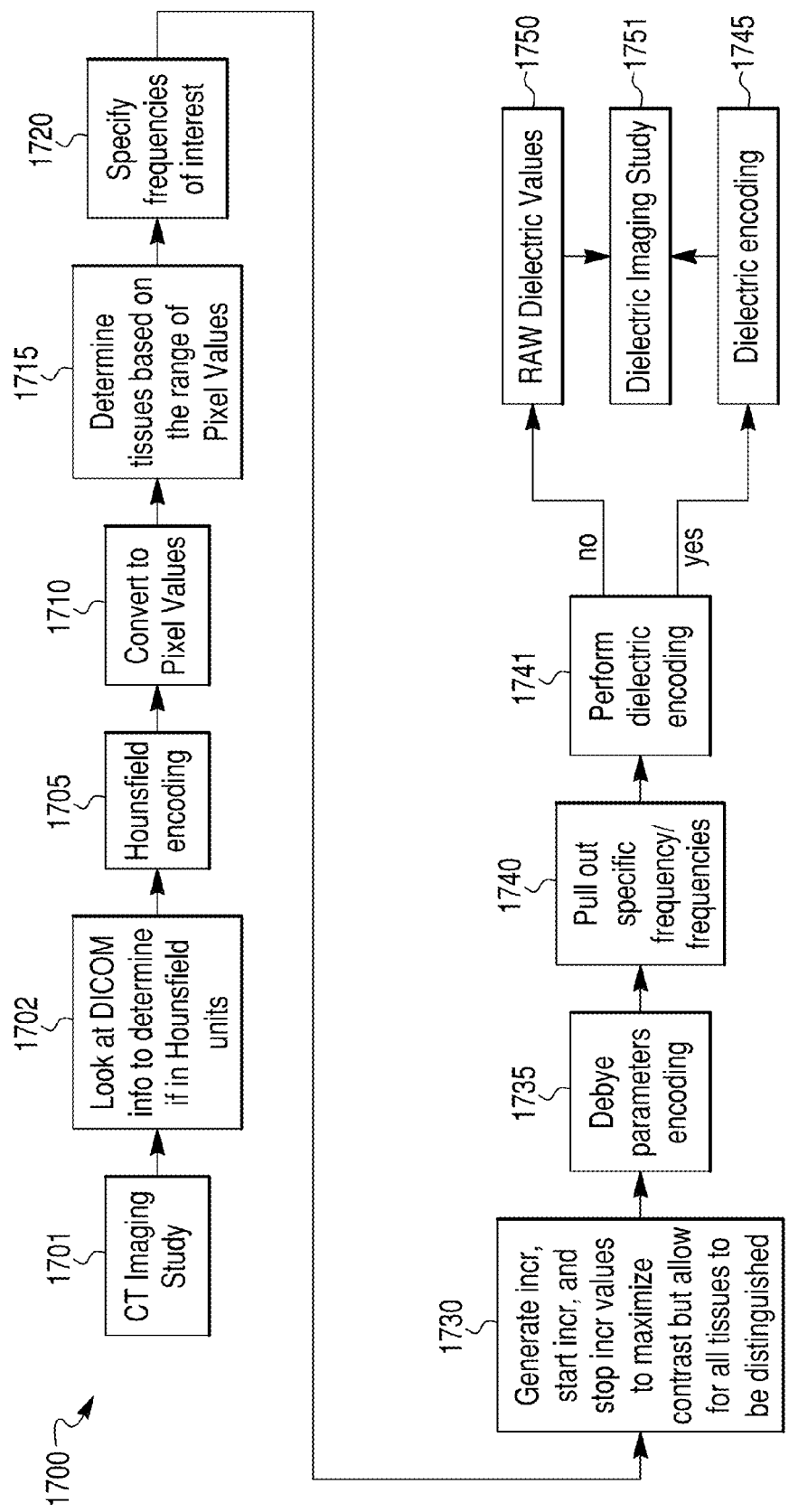
FIG. 17 is a flow chart of exemplary steps used in the conversion between Hounsfield encoded images and RAW dielectric images using frequency dependency.

FIG. 17 is a flow chart 1700 of exemplary steps used in the conversion between CT images and RAW dielectric images using a frequency dependent model. Flow chart 1700 can be thought of as an extension of flow chart 500 to allow for a frequency dependent form. In step 1701, a CT image from acquisition site 101 is presented. In step 1702, the DICOM info is looked at to determine if the CT image is already in Hounsfield units. If the CT image is not in Hounsfield units, computing environment 102 converts the image to Hounsfield units through the Hounsfield encoding procedure established at step 1705. In step 1710, the Hounsfield encoded CT image is converted to pixel values. In step 1715, the tissues for each pixel value in the image are determined based on the range of the pixel values. In step 1720, a wideband frequency of interest is specified by computing environment 102 or manually by the user.

In step 1730, incremental variables are determined. The wideband frequency range from step 1720 along with the range of the pixel values for each tissue in step 1715 is used to generate the incr variable, start incr variable, and stop incr variable in step 1730. The incr variable, start incr variable, and stop incr variable are designed to maximize the contrast between tissues for all tissues to be distinguished. In step 1735, the pixel values are converted to Debye parameters. In step 1740, a specific frequency or frequencies of interest are specified to be used to generate dielectric values (dielectric images) from the Debye equation presented above. In step 1741, the computing environment 102 or the user manually decides to have the dielectric images encoded (i.e. MAC units). In step 1745, dielectric encoding of the image occurs at a frequency or frequencies. In step 1750, the RAW dielectric images at a frequency or frequencies of interest are obtained. In step 1751, the dielectric encoded images and/or raw dielectric images are converted into the DICOM format. Steps 1740 through 1750 may not be necessary or one or more of steps 1740 through 1750 may be necessary depending on the particular application at hand and the desired output image format. In an embodiment, a combination of steps 1740 through 1750 may be necessary depending on the particular application at hand and the desired output image format.

Figure 18:
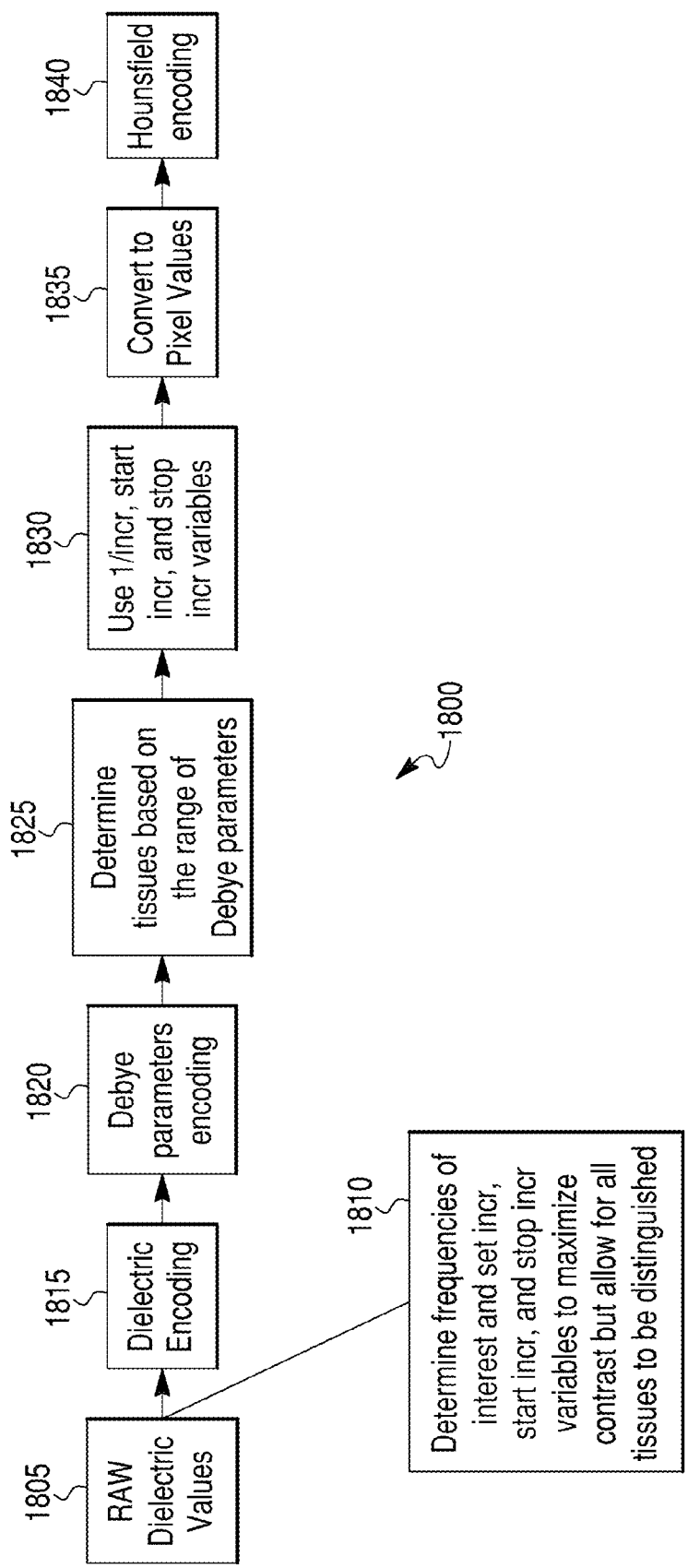
FIG. 18 is a flow chart of exemplary steps used in the conversion between RAW dielectric images and Hounsfield encoded images using frequency dependency.

FIG. 18 is a flow chart 1800 of exemplary steps that can be used in the conversion between RAW dielectric images to Hounsfield encoded images using a frequency dependent model. Flow chart 1800 can be thought of as an extension of flow chart 400 to allow for a frequency dependent form. In step 1805, RAW dielectric values which have been reconstructed from microwave scattering data in computing environment 102 which was collected at acquisition site 101 forming an image at multiple frequencies are presented. In step 1810, it is determined what frequencies the RAW dielectric values fall into (this may already be known). In addition, at step 1810, the appropriate incr variable, start incr variable, and stop incr variable are determined for the frequencies. In step 1815, a decision is made automatically by computing environment 102 or manually by a user whether to perform dielectric encoding on the RAW dielectric images. Should a decision be made to proceed with dielectric encoding, the RAW dielectric values are dielectric encoded at step 1815.

Continuing with FIG. 18, in step 1820, the Debye parameters are generated from the raw dielectric values for all of the frequencies. In step 1825, the tissues selected as present in each pixel are determined by looking at the range of each Debye parameter in which each pixel falls into. In step 1830, the appropriate 1/incr value for the tissue is used along with the start incr and stop incr variables. In step 1835, the Debye parameters are converted to pixel values. In step 1840, the pixel values are Hounsfield encoded. In an embodiment, a process may begin with determining what frequencies the RAW dielectric values fall into and correlating these frequencies with the appropriate incr value in step 1810 and proceeding to generating the Debye parameters in step 1820 before completing the remainder of the steps 1825 through 1840 from FIG. 18.

Conversion Between Hounsfield Units and Dielectric Values

Using literature results for Hounsfield units and dielectric properties, it is possible to convert dielectric encoded images to Hounsfield encoded images and vice versa. Several example calculations will be presented below which rely on the Hounsfield Units, Complex Permittivity, and Real Permittivity Increment for the 30 tissues established in Table I at a frequency of 300 MHz. The present methods are not limited to the 30 tissues presented in Table I and may be performed utilizing any number of tissues within the human body. Furthermore, the present microwave image processing system 100 is not limited to a frequency of 300 MHz. Any frequency within the range 100 MHz to 10 GHz can be used as a basis for the image processing system 100 presented herein.

The complex permittivity values for each tissue (except air and water) are based on the four-pole Cole-Cole model developed by Gabriel and colleagues in 1996. Table III shows the four-pole Cole-Cole parameters for lung inflated. These can be used in the four-pole Cole-Cole equation to calculate what is referred to as dielectric.lung_inflated.

$$\varepsilon(\omega) = \varepsilon_\infty + \sum_{i=1}^{4} \frac{\Delta \varepsilon_i}{1 + (j\omega\tau_i)(1-\alpha_i)} + \frac{\sigma_s}{j\omega\varepsilon_0}$$

$$\varepsilon(\omega) = 2.5 + \frac{18}{1 + (j\omega * 7.958 * 10^\wedge - 12)^{(1-0.1)}} +$$
$$\frac{500}{1 + (j\omega * 63.662 * 10^\wedge - 9)^{(1-0.1)}} +$$
$$\frac{2.5 * 10^\wedge 5}{1 + (j\omega * 159.155 * 10^\wedge - 6)^{(1-0.2)}} +$$
$$\frac{4 * 10^\wedge 7}{1 + (j\omega * 7.958 * 10^\wedge - 3)^{(1-0)}} + \frac{0.03}{j\omega\varepsilon_0}$$
$$= 24.7727 - 21.3530i$$

Where
$$\omega = 2 * \pi * f$$
$$f = 300 * 10^6 \text{ Hz (300 MHz)}$$
$$\varepsilon_0 = 8.85 * 10^\wedge - 12$$

Table II shows the tissue types presented in Gabriel and colleagues (1996) and the tissue types utilized in sample calculations which demonstrate dielectric to Hounsfield conversion and vice versa. The microwave image processing system presented herein can be applied to any number of tissues within the human body and is not limited to those displayed in Table II. Table III shows the tissue types presented in Gabriel and colleagues 1996 that are utilized in sample calculations below and their corresponding four-pole Cole-Cole parameters.

In the left-hand column of Table II, the tissues from Gabriel and colleagues 1996, were selected based upon consulting literature values for Hounsfield units. In an embodiment different reference sources were consulted to determine Hounsfield unit ranges representative of tissues in the human body. In an embodiment, Schneider, Bortfled, and Schlegel, 2000, and Schneider, Pedroni, and Lomax, 1996 were consulted to determine Hounsfield unit ranges representative of tissues in the human body. (Schneider, W., T. Borfeld, and W. Schlegel. Correlation between CT numbers and tissue parameters needed for Monte Carlo simulations of clinical dose distributions. Phys. Med. Biol. vol. 45, pp. 459-478, 2000 and Schneider, Uwe, E. Pedroni, and A. Lomax. The calibration of CT Hounsfield units for radiotherapy treatment planning. Phys. Med. Biol. vol. 41, pp. 111-124, 1996). In an embodiment, Hounsfield units were derived based on the mass attenuation coefficients in ICRU Report 46 (Photon, Electron, Proton and Neutron Interaction Data for Body Tissues. ICRU Report 46. International Commission on Radiation Units and Measurements, Bethesda, 1992). In an embodiment, a unique range of Hounsfield units was assigned for each tissue selected to represent the human body. Variability of the Hounsfield units for different tissues exists and multiple references were consulted to best help determine the range of Hounsfield units to assign.

The specific ranges in Table I for each Hounsfield unit appear to have overlapping values for example lung inflated is presented as "−840 to −190" and adipose tissue is presented as "−190 to −51". This should be interpreted as the range for lung inflated including every Hounsfield unit from −840 to −190, but not including −190, meaning that −190 would be included in adipose tissue. Hounsfield units are typically thought of as integer values, however some of the tissues such as kidney and spleen were allowed to have non-integer values of cutoffs in their ranges in order to distinguish these tissues from other tissues with a similar range of Hounsfield units. Thus, in the example of Table I, each tissue has a unique range of Hounsfield units. Table VII shows an example where each tissue or tissue grouping has a unique range of Hounsfield units.

Example I

Dielectric Encoded Image to Hounsfield Encoded Image Conversion at 300 MHz

An example of converting from dielectric encoded images to Hounsfield encoded images is carried out for lung inflated and for cancellous bone at a frequency of interest, which embodies the present image processing system 100, is now presented. Initially, the range of the real permittivity of each tissue for the frequency of interest was determined. At 300 MHz, for lung inflated, the maximum in the range is calculated as $$\text{max\_dielectric.lung\_inflated} =$$
$$(-190 - (-840)) * incr + \text{dielectric.lung\_inflated} =$$
$$(-190 + 840) * .0005 + \text{dielectric.lung\_inflated} =$$
$$(-190 + 840) * .0005 + 24.7727 - 21.3530i = 25.0977 - 21.3530i$$

The minimum in the range is dielectric.lung_inflated. If the real permittivity is between 24.7727 and 25.0977, the tissue is assigned lung and the Hounsfield unit is calculated as follows. In this example, tissue type is decided based on real permittivity (each tissue type has a unique range of real permittivity). However, tissue type can be decided based on other parameters in Table I or a combination of parameters in Table I. In the above equation, −190 and −840 come from the Hounsfield unit range that lung inflated falls in as shown in Table I.

$$H_{out}(x, y) = \{\text{real}[D_{in}(x, y)] - \text{real}[\text{dielectric.lung\_inflated}]\} * \frac{1}{incr} - 840$$
$$H_{out}(x, y) = \{\text{real}[D_{in}(x, y)] - \text{real}[\text{dielectric.lung\_inflated}]\} * 2000 - 840$$

The 2000 in the above equation comes from 1/0.0005=2000 where 0.0005 is the real permittivity increment for lung inflated as indicated in Table I. Where dielectric.lung_inflated=2_=24.7727−21.3530i at 300 MHz, $H_{out}(x,y)$ corresponds to the Hounsfield unit at Cartesian coordinate (x,y), and $D_{in}(x, y)$ corresponds to the complex permittivity at Cartesian coordinate (x,y). For example if $D_{in}(x,y)=24.8427−21.3530 i$ then $$H_{out}(x,y)=(24.8427-24.7727)*2000-840=-700$$

In this example, a difference in real permittivity (24.8427−24.7727) is used (along with the inverse of the increment value and the lower limit of the Hounsfield unit range for inflated lung of −840) to convert to Hounsfield units, but other parameters in Table I or a combination of parameters in Table I may be used to convert.

At 300 MHz, for cancellous bone, the maximum in the range is calculated as $$\text{max\_dielectric.cancellous\_bone} =$$
$$(300 - 120) * incr + \text{dielectric.cancellous\_bone} =$$
$$(300 - 120) * .001 + \text{dielectric.cancellous\_bone} =$$
$$(300 - 120) * .001 + 23.1628 - 12.9158i = 23.3428 - 12.9158i$$

The minimum in the range is dielectric.cancellous_bone. If the real permittivity is between 23.1628 and 23.3428 the tissue is assigned cancellous bone and the Hounsfield unit is calculated as follows. In the above equation, 300 and 120 come from the Hounsfield unit range that cancellous bone falls in as shown in Table I.

$$H_{out}(x, y) =$$
$$\{\text{real}[D_{in}(x, y)] - \text{real}[\text{dielectric.cancellous\_bone}]\} * \frac{1}{incr} + 120$$
$$H_{out}(x, y) = \{\text{real}[D_{in}(x, y)] - \text{real}[\text{dielectric.cancellous\_bone}]\} * 1000 + 120$$

The 1000 in the above equation comes from 1/0.001=1000 where 0.001 is the real permittivity increment for cancellous bone as indicated in Table I. Where dielectric.cancellous_bone=23.1628−12.9158i at 300 MHz, $H_{out}(x,y)$ corresponds to the Hounsfield unit at Cartesian coordinate (x,y), and $D_{in}(x, y)$ corresponds to the complex permittivity at Cartesian coordinate (x,y). For example if $D_{in}(x, y)=23.2428−12.9158i$ then $$H_{out}(x,y)=(23.2428-23.1628)*1000+120=200$$

Similar equations for the other tissues present can be written following the sample form of the example equations presented and the information provided in Table 1.

Example II

Hounsfield Encoded Image to Dielectric Encoded Image Conversion at 300 MHz

An example of converting from Hounsfield encoded images to dielectric encoded images, according to an embodiment, is carried out for lung inflated and for cancellous bone at a frequency of interest. For lung inflated if the Hounsfield unit falls between −840 and −190 then the Hounsfield unit is converted to a complex permittivity according to the equation.

$$D_{out}(x,y)=(H_{in}(x,y)-(-840))*incr+\text{dielectric.lung\_inflated}$$
$$D_{out}(x,y)=(H_{in}(x,y)+840)*0.0005+\text{dielectric.lung\_inflated}$$

Where dielectric.lung_inflated=24.7727−21.3530i at 300 MHz, incr=0.0005 at 300 MHz, $H_{in}(x, y)$ corresponds to the Hounsfield unit at Cartesian coordinate (x,y), and $D_{out}(x,y)$ corresponds to the complex permittivity at Cartesian coordinate (x,y). For example if $H_{in}(x, y)=-700$ then $$D_{out}(x,y)=(-700+840)*0.005+24.7727-21.3530i=24.8427-21.3530i$$

For cancellous bone, if the Hounsfield unit falls between 120 and 300, then the Hounsfield unit is converted to a complex permittivity according to the equation.

$$D_{out}(x,y)=(H_{in}(x,y)-120)*incr+dielectric.cancellous\_bone$$

$$D_{out}(x,y)=(H_{in}(x,y)-120)*0.001+dielectric.cancellous\_bone$$

Where dielectric.cancellous_bone=23.1628−12.9158i at 300 MHz, incr=0.001 at 300 MHz, $H_{in}(x, y)$ corresponds to the Hounsfield unit at Cartesian coordinate (x,y), and $D_{out}(x, y)$ corresponds to the complex permittivity at Cartesian coordinate (x,y). For example if $H_{in}(x, y)=200$ then, $$D_{out}(x,y)=(200-120)*0.001+23.1628-12.9158i=23.2428-12.9158i$$

Similar equations for the other tissues present can be written following the sample form of the example equations presented and the information provided in Table I. One important item to note is that tissues for lymph, pancreas, and prostate are not present in the database by Gabriel and colleagues in 1996 and have been assigned values of thyroid in implementation. Hence, these equations are slightly different than the example equations presented in Example I and Example II. It is necessary to increment lymph, pancreas, prostate, and thyroid tissues in such a way that the dielectric values are assigned based on how the other tissues were assigned so as to preserve uniqueness. This is done by starting the next tissue that uses the dielectric properties of thyroid from the previous largest increment for the tissue that used thyroid.

Figure 8:
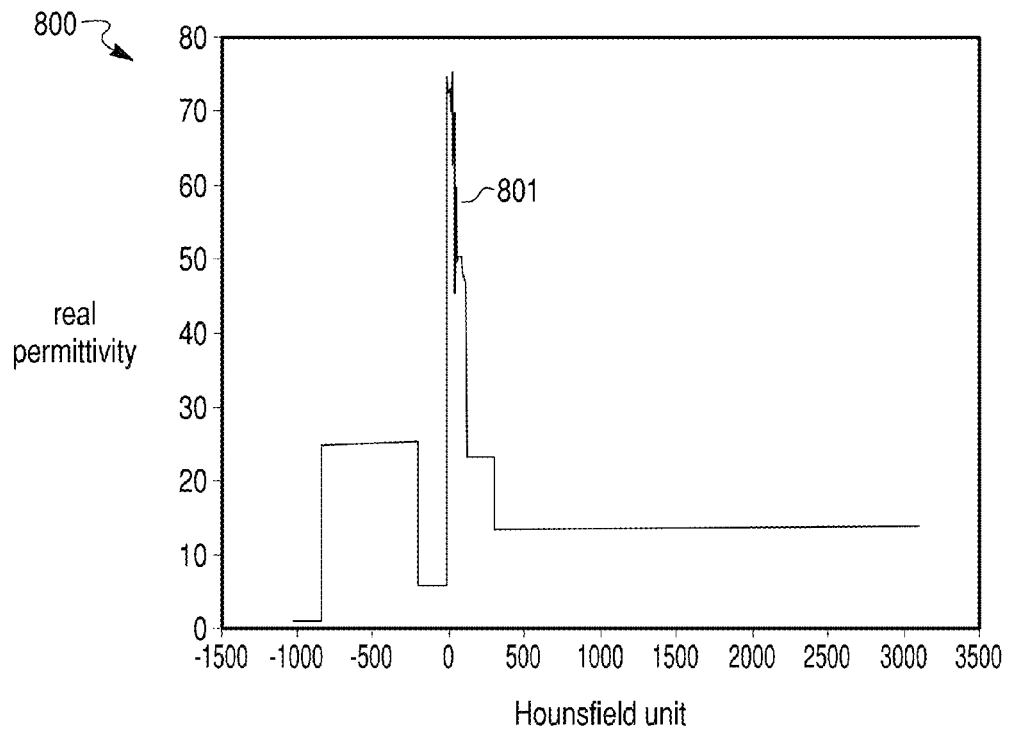
FIG. 8 is a graph which shows the relationship between real permittivity and Hounsfield unit at 300 MHz based on the tissues listed in Table I.
Figure 9:
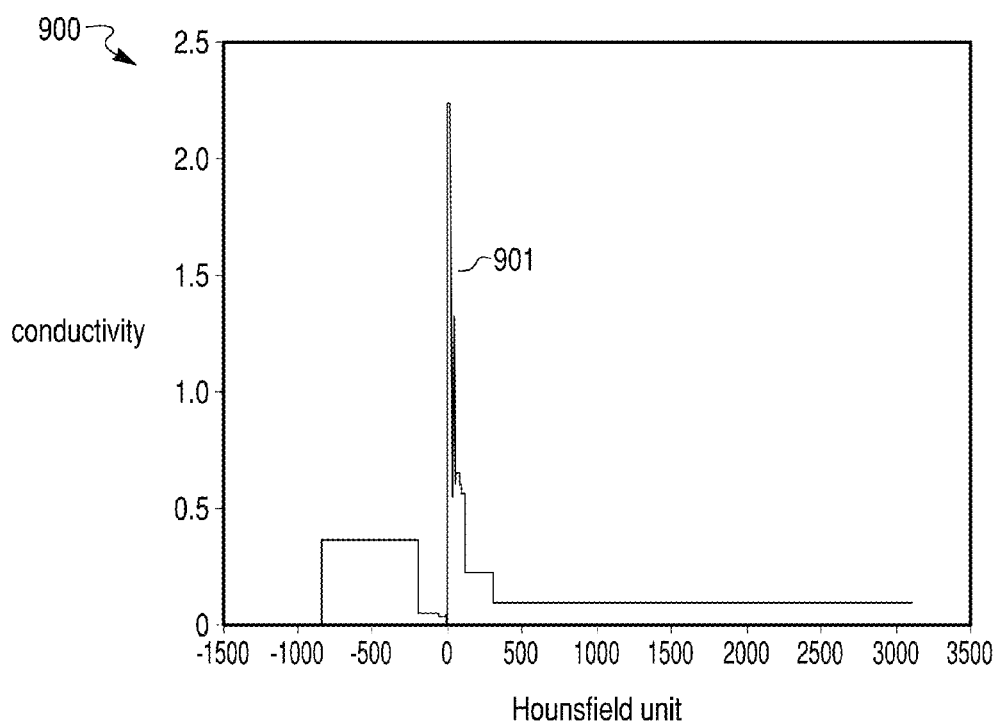
FIG. 9 is a graph which shows the relationship between conductivity and Hounsfield unit at 300 MHz based on the tissues listed in Table I.
Figure 10:
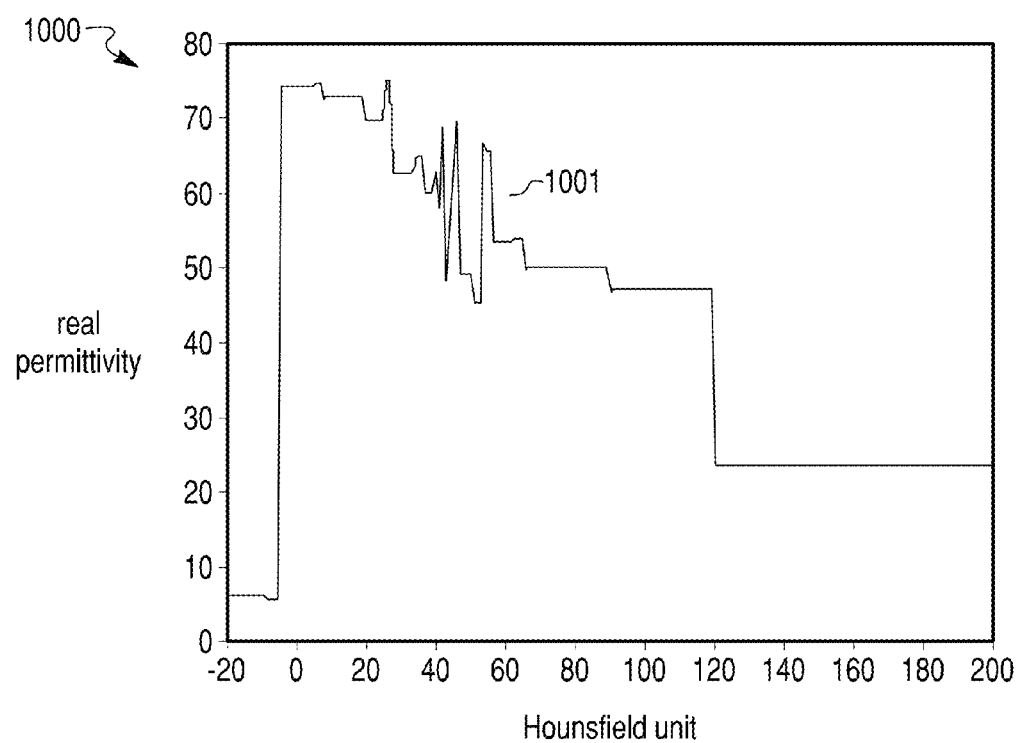
FIG. 10 is a graph which shows the relationship between real permittivity and Hounsfield unit at 300 MHz, based on the tissues listed in Table I, for the Hounsfield unit range from −20 to 200.
Figure 11:
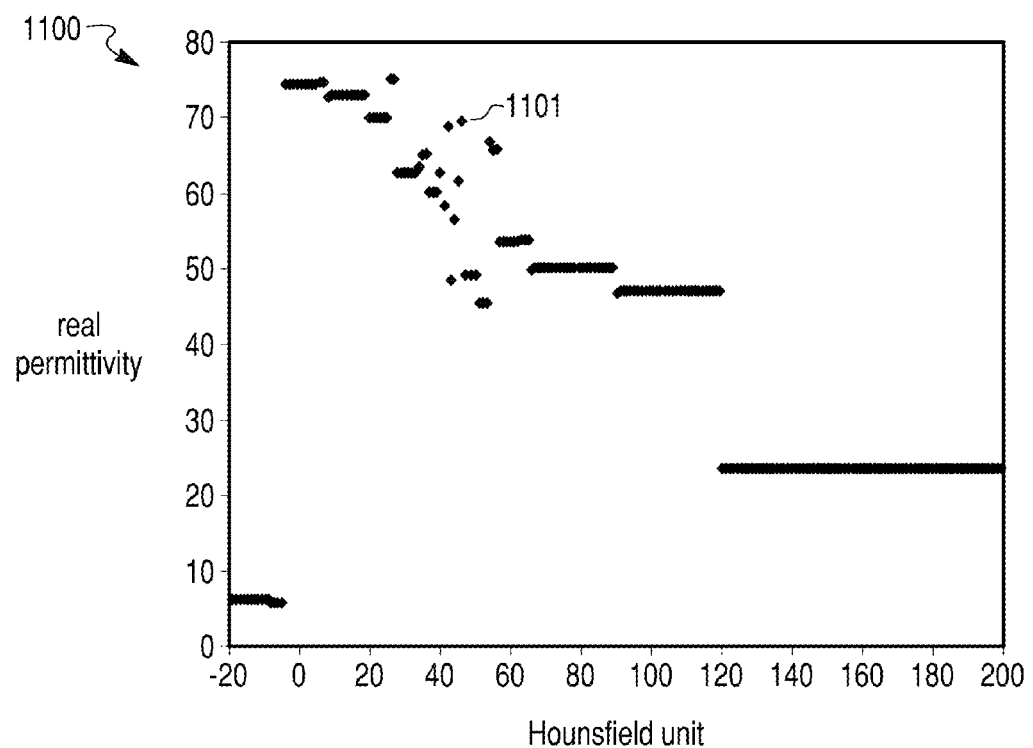
FIG. 11 is a graph which shows the relationship between real permittivity and Hounsfield unit at 300 MHz, based on the tissues listed in Table I, for the Hounsfield unit range from −20 to 200 without connecting lines.

FIG. 8 is a graph 800 which shows the relationship between real permittivity and Hounsfield unit at 300 MHz based on the tissues listed in Table I. FIG. 9 is a graph 900 which shows the relationship between conductivity and Hounsfield unit at 300 MHz based on the tissues listed in Table I. It is clear from FIG. 8 and FIG. 9 that the Hounsfield unit in the range 801, 901 from approximately −20 to 200 is difficult to distinguish. A zoomed in version of FIG. 8 focusing on this Hounsfield unit range 1001 is presented in the graph 1000 of FIG. 10. FIGS. 8-10 have lines connecting each Hounsfield unit which is not present in reality. FIG. 11 is a graph 1100 that shows the same information as FIG. 10 but with a dot 1101 indicating each Hounsfield unit in the range from −20 to 200.

Figure 12:
FIG. 12 shows an example of a CT image in Hounsfield units.
Figure 13:
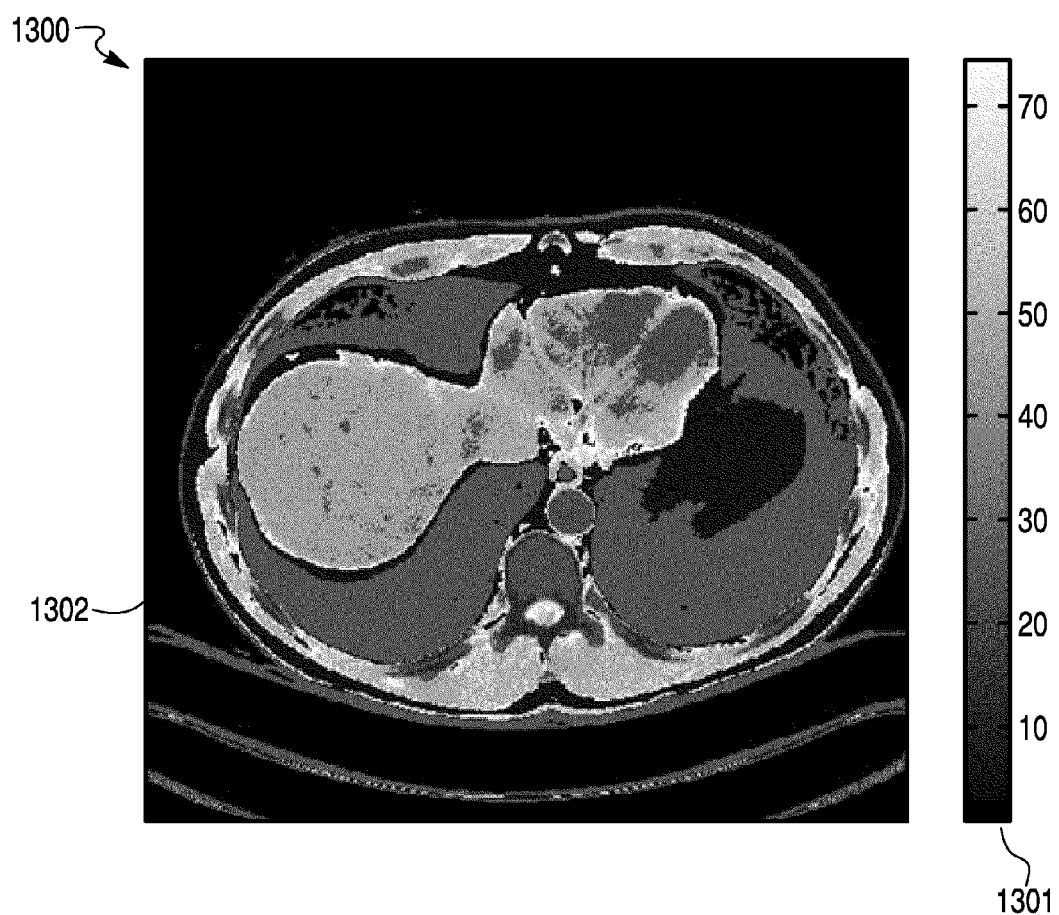
FIG. 13 shows the CT image of FIG. 12 converted from Hounsfield units to real permittivity at 300 MHz using an embodiment of the present invention.
Figure 14:
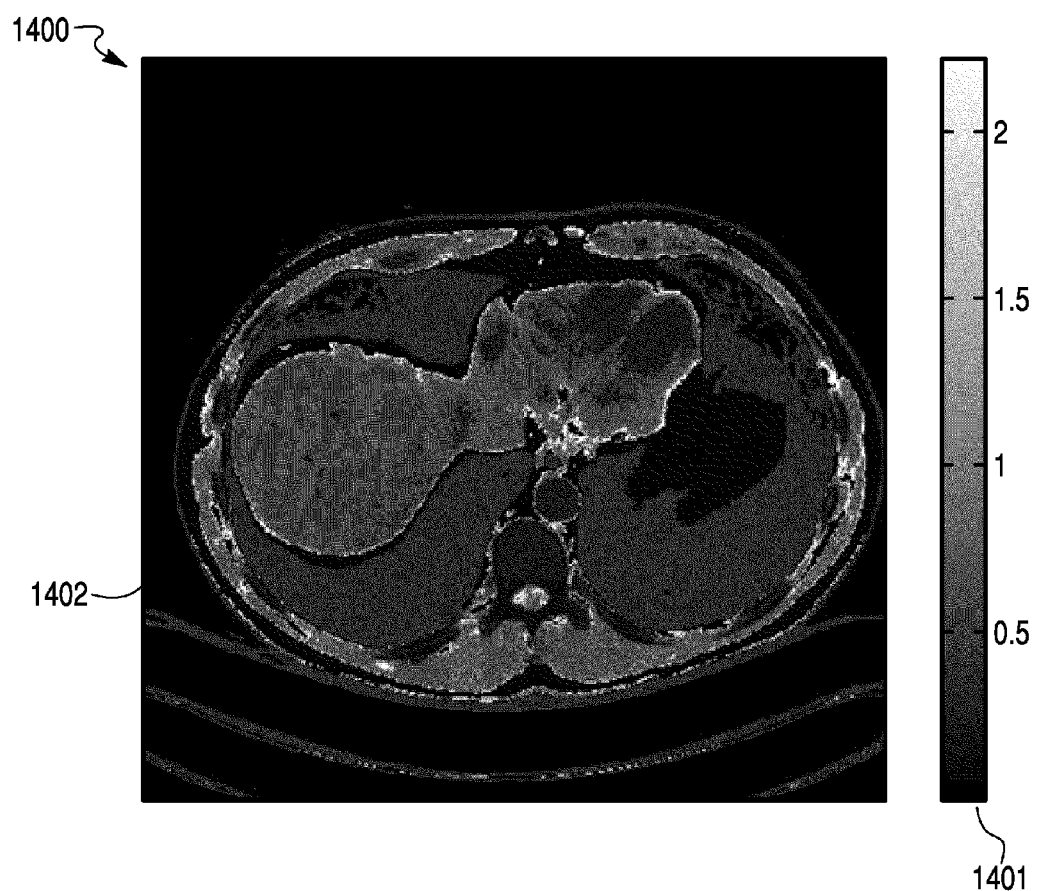
FIG. 14 shows the CT image of FIG. 12 converted from Hounsfield units to conductivity at 300 MHz using an embodiment of the present invention.

FIG. 12 shows an example of a CT image 1200 of a tissue 1202 in Hounsfield units 1201. FIG. 13 is an image 1300 showing the CT image of FIG. 12 having been converted from Hounsfield units to real permittivity 1301 at 300 MHz using an embodiment of the present invention. FIG. 14 is an image 1400 showing the CT image of FIG. 12 converted from Hounsfield units to conductivity 1401 at 300 MHz using an embodiment of the present invention. Other types of images may be generated, for example, images that are a combination of real and imaginary components of the permittivity. Through the image processing system 100 presented herein, it is then possible to convert from the real permittivity and conductivity back to the original image shown in FIG. 12.

This conversion between a Hounsfield unit and a dielectric value at each pixel (described above for a single frequency) can be performed for more than one frequency. When this is done, the dielectric values at different frequencies can be combined. In one embodiment, the dielectric values at different frequencies are combined into a one-pole Debye model. In another embodiment, the dielectric values at different frequencies are combined into a four-pole Cole-Cole model.

Frequency Dependent Conversion Between Raw Dielectric Images and Hounsfield Encoded Images The real permittivity increment values used in converting Hounsfield encoded images to RAW dielectric images and the inverse of the real permittivity increment values used in converting RAW dielectric images to Hounsfield encoded images need to change at different frequencies. This frequency dependency is based on the dynamic range of the dielectric values being dependent on the frequency used. Increasing the frequency decreases the dynamic range of the real permittivity. Decreasing the frequency increases the dynamic range of the real permittivity. In order to more readily demonstrate the effects of frequency and help alleviate needing to change the increment values at different frequencies, a frequency dependent conversion process in the reverse and forward directions, as illustrated in FIGS. 17 and 18, has been presented and will be described in more detail below.

According to an embodiment, before the development of the frequency dependent RAW dielectric image to Hounsfield encoded image conversion procedure the four-pole Cole-Cole parameters presented in Table III were converted to one-pole Debye parameters as presented in Table V. A significant benefit of generating one-pole Debye parameters stems from their easier use in FDTD codes. An optimization algorithm that can be adaptive with an extended initialization scheme can be used for determining the four Debye parameters for each tissue. An extended initialization procedure is where an extended amount of random initializations are performed until a maximum number of these initializations is reached (Sentinella, M. R., and L. Casalino, "Enhanced Continuous Tabu Search in a Hybrid Evolutionary Algorithm For the Optimization of Interplanetary Trajectories,"21st International Symposium on Space Flight Dynamics, Toulouse, France, 2009). The entire contents of this publication is incorporated herein by reference for the optimization and initialization techniques described therein.

An example of the cost function to be minimized by an optimization algorithm that can be adaptive is the sum of the squared differences between the Gabriel model (multi-dispersion Cole-Cole) and the Debye model.

$$\text{Cost} = \sum_{f=first\_freq}^{f=last\_freq} \{\log10[c_r(f)] - \log10[d_r(f)]\}^2 + \{\log10[c_i(f)] - \log10[d_i(f)]\}^2$$

Where $c_r(f)$ is the real part of the Cole-Cole function, $c_i(f)$ is the imaginary part of the Cole-Cole function, $d_r(f)$ is the real part of the Debye function, and $d_i(f)$ is the imaginary part of the Debye function. The sum is based on the square of the differences between the number of frequencies used of the real parts and square of the differences between the number of frequencies of the imaginary parts. The cost function for this example calculation was developed by Clegg and Robinson (2012), however a variety of cost functions can be used to generate Debye parameters in accordance with the microwave image processing system presented herein.

In an embodiment, ACPSO is used to minimize this cost function. The parameters of an ACPSO scheme according to an embodiment are presented in Table IV. In this embodiment, 1000 iterations of ACPSO were used with 750 iterations in the extended initialization scheme. In other embodiments, other classic gradient based optimization methods can be used or other metaheurstic algorithms such as the genetic algorithm or simulated annealing can be used. Xin-She Yang (2010) provides a discussion of numerous optimization algorithms which can be utilized (Xin-She Yang. Engineering Optimization: An Introduction with Metaheuristic Applications. John Wiley & Sons. 2010). The entire contents of this publication are incorporated herein by reference for the initialization and optimization techniques described therein.

In an embodiment, the boundaries for the four Debye parameters were held on a log scale. The boundaries used were $$\log 10(\in_\infty) \in (0,1)$$

$$\log 10(\Delta\in_1) \in (-3,8)$$

$$\log 10(\tau) \in (-12,-1)$$

$$\log 10(\sigma_s) \in (-4,0)$$

In this case, the Debye model is used with $\Delta\in_1$ instead of using $\in_s-\in_\infty$, where $\Delta\in_1=\in_s-\in_\infty$. This makes it necessary to then solve for $\in_s$ using $\in_s=\Delta\in_1+\in_\infty$. In an embodiment an optimization algorithm that can be adaptive is run three times for each tissue in the model and the best result based on the lowest cost function value is selected as the Debye model parameters for that tissue.

Table V shows the one-pole Debye parameters generated using ACPSO to minimize a cost functional between the four-pole Cole-Cole model from Gabriel and colleagues 1996 over the frequency range 0.5 GHz to 10 GHz with 200 samples (for the tissues utilized as in Table III). In addition, the one-pole Debye parameters generated using ACPSO to minimize a cost functional between the equation for the model for water presented in Meissner and Wentz 2004 is also added (Meissner, T. and F. J. Wentz. The Complex Dielectric Constant of Pure and Sea Water from Microwave Satellite Observations. IEEE Transactions on Geoscience and Remote Sensing. Vol. 42, no. 9, pp. 1836-1849, 2004). The tissues have been rearranged so that the smallest eps s appears on the top of the table increasing to the largest eps s on the bottom of the table.

Figure 19:
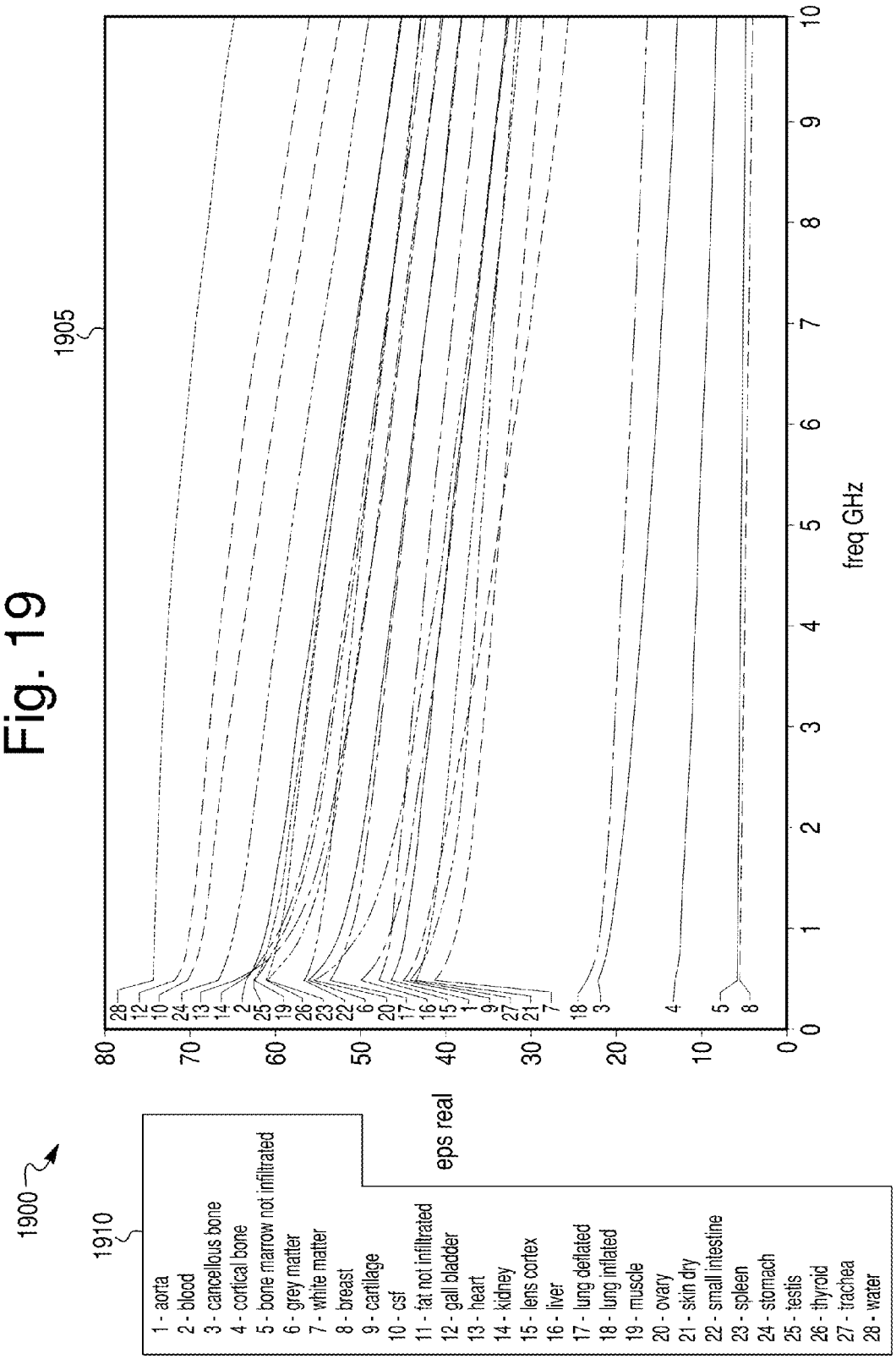
FIG. 19 is a graph which shows the real permittivity based on the four-pole Cole-Cole curves of the tissues utilized in Table II over the frequency range 0.5 GHz to 10 GHz.
Figure 20:
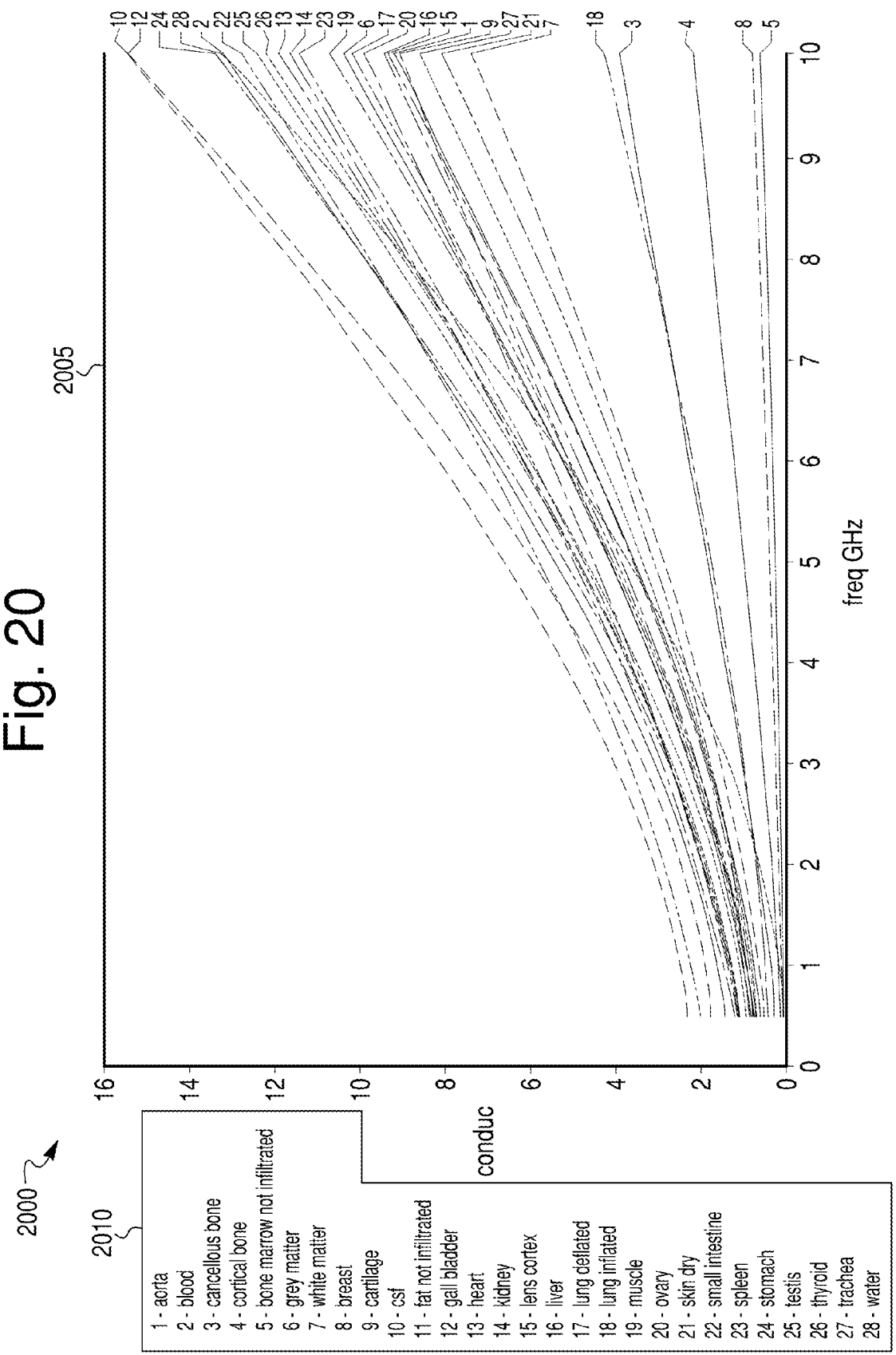
FIG. 20 is a graph which shows the conductivity based on the four-pole Cole-Cole curves of the tissues utilized in Table II over the frequency range 0.5 GHz to 10 GHz.
Figure 21:
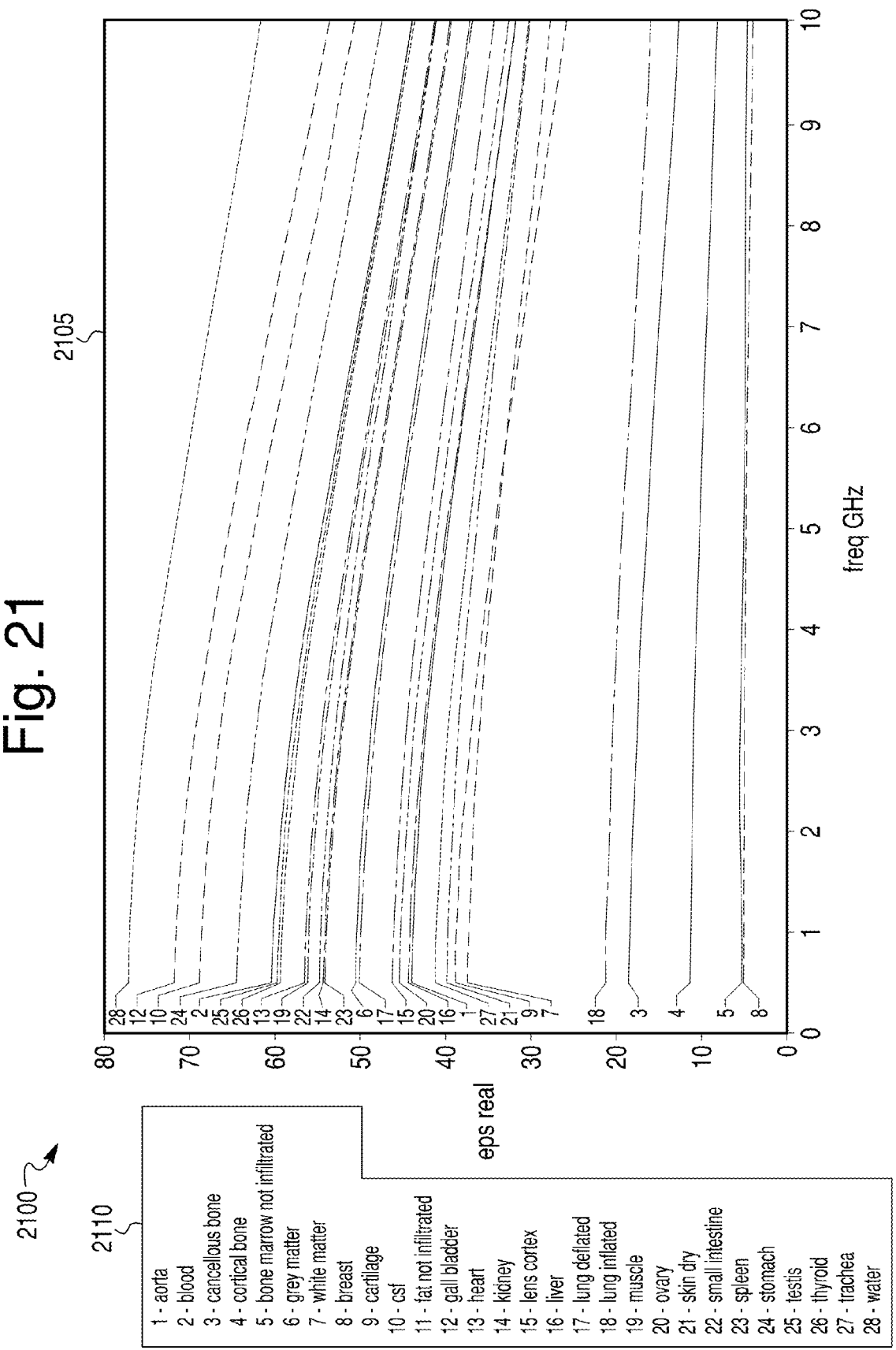
FIG. 21 is a graph which shows the real permittivity of a generated one-pole Debye model of the tissues listed in Table II over the frequency range 0.5 GHz to 10 GHz.
Figure 22:
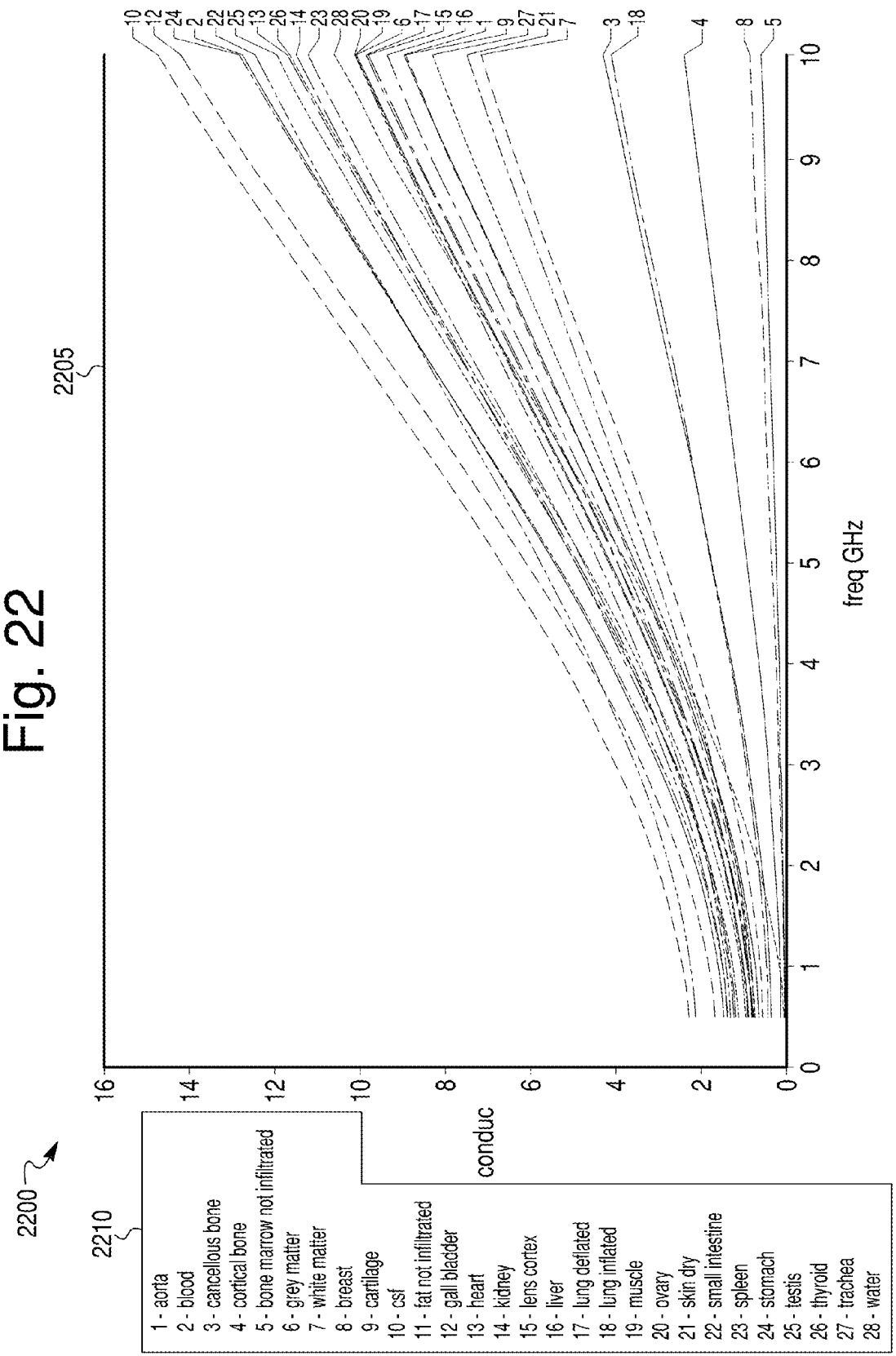
FIG. 22 is a graph which shows the conductivity of a generated one-pole Debye model of the tissues listed in Table II over the frequency range 0.5 GHz to 10 GHz.

FIG. 19 and FIG. 20 show the real permittivity 1905 and conductivity 2005 respectively based on the four-pole Cole-Cole curves of the tissues 1910, 2010 indicated in Table III over the frequency range 0.5 GHz to 10 GHz with 200 samples. The tissues and four-pole Cole-Cole parameters have been presented in Table III. FIG. 21 and FIG. 22 show the real permittivity and conductivity of the generated one-pole Debye model of the same tissues over the frequency range 0.5 GHz to 10 GHz with 200 samples. A cost functional is minimized using ACPSO to determine the one-pole Debye parameters by comparing to the generated complex permittivity based on the four-pole Cole-Cole models over the frequency range 0.5 GHz to 10 GHz with 200 samples. The tissues and Debye parameters have been presented in Table V.

Figure 23:
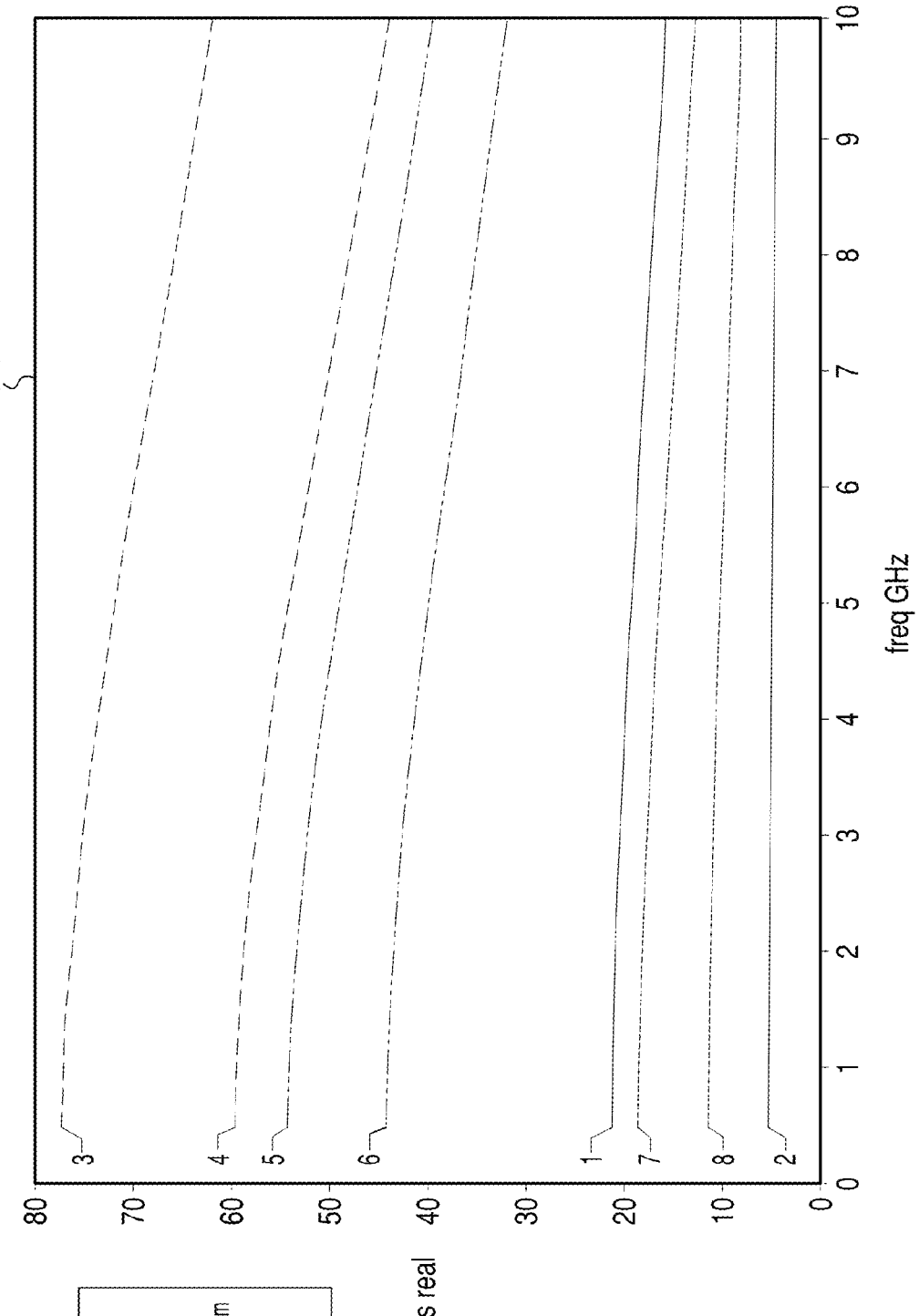
FIG. 23 is a graph which shows the real permittivity of a reduced number of tissues for a one-pole Debye model generated over the frequency range 0.5 GHz to 10 GHz.
Figure 24:
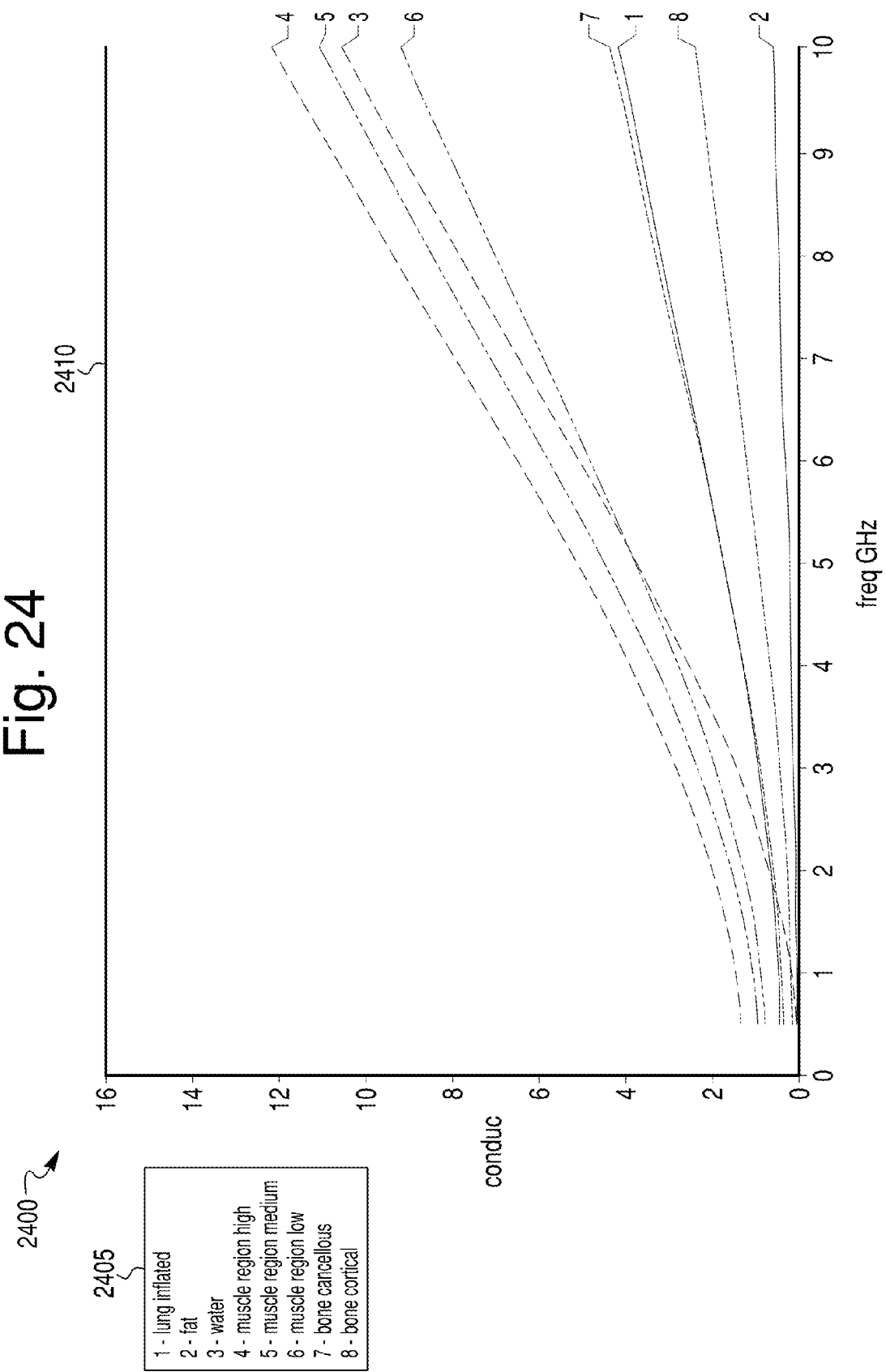
FIG. 24 is a graph which shows the conductivity of a reduced number of tissues for a one-pole Debye model generated over the frequency range 0.5 GHz to 10 GHz.

It is apparent from inspecting FIG. 21 and FIG. 22 along with Table V that many of the tissues 2110, 2210 have similar Debye parameters and consequently similar looking Debye curves. Due to this, a simplification is made to reduce the amount of tissues used. FIG. 23 and FIG. 24 show the real permittivity 2310 and conductivity 2410 of the reduced tissues 2305, 2405 one-pole Debye model generated over the frequency range 0.5 GHz to 10 GHz with 200 samples. The tissues and Debye parameters used in the display in FIG. 23 and FIG. 24 are presented in Table VI.

Table VI shows the reduced number of tissues with their corresponding one-pole Debye parameters. In this embodiment, the Debye parameters for water, cancellous bone, and cortical bone have been maintained as those presented in Table V. For fat, the new one-pole Debye parameters presented in Table VI represent the median of the Debye parameters for breast fat, not infiltrated fat, and not infiltrated bone marrow as presented in Table V. The muscle region low, muscle region median, and muscle region high Debye parameters represent the 25th quartile, median (50th quartile), and 75th quartile, respectively, of the remaining tissues in Table V. The tissues utilized for the three groups of muscle regions include specifically white matter, cartilage, dry skin, trachea, aorta, liver, ovary, lens cortex, deflated lung, grey matter, spleen, kidney, muscle, small intestine, heart, thyroid, testis, blood, stomach, cerebrospinal fluid, and gallbladder bile. The tissues for the three groups of muscle regions were decided upon by noting in Table I that their Hounsfield unit ranges all fell within a similar narrow range from 8 to 120.

Table VII shows the one-pole Debye parameters for the reduced amount of tissues along with other information useful in the conversion process. In an embodiment, tissue ranges can be chosen to fall in a specific Hounsfield range of units and corresponding pixel values can be determined. Pixel values are determined by adding 1024 to all of the Hounsfield units so that all pixel values are positive and non-negative. The specific ranges in Table VII for each Hounsfield unit were based on Table I but taking into account that many of the tissues were condensed as described earlier. For fat, the Hounsfield unit range covers the range previously presented for breast fat, not infiltrated fat, and not infiltrated bone marrow. For the three muscle region groups, a new range was determined to be from 8 to 120 based upon the previously presented tissues in that region. In an embodiment, the cutoff of the Hounsfield unit range for each of the three muscle region groups was taken as an average, to allow for each region to be represented over roughly the same amount of Hounsfield units. Table VII also shows the minimum $\in_s$ parameter and increment value of the $\in_s$ parameter for each tissue. Further, the start and stop increment are shown.

In an embodiment presented in Table VII, tau has been held constant in all cases at 1.3E-11. Tau can be held constant in this manner such that the ranges of all tissues between the $\in_s$ parameter to the minimum $\in_s$ parameter do not overlap. The minimum $\in_s$ parameter is determined along with the increment, start increment, and stop increment, to help maximize contrast but allow for all tissues to be distinguished. There is some flexibility in the minimum $\in_s$ parameter and the increment values used.

Figure 25:
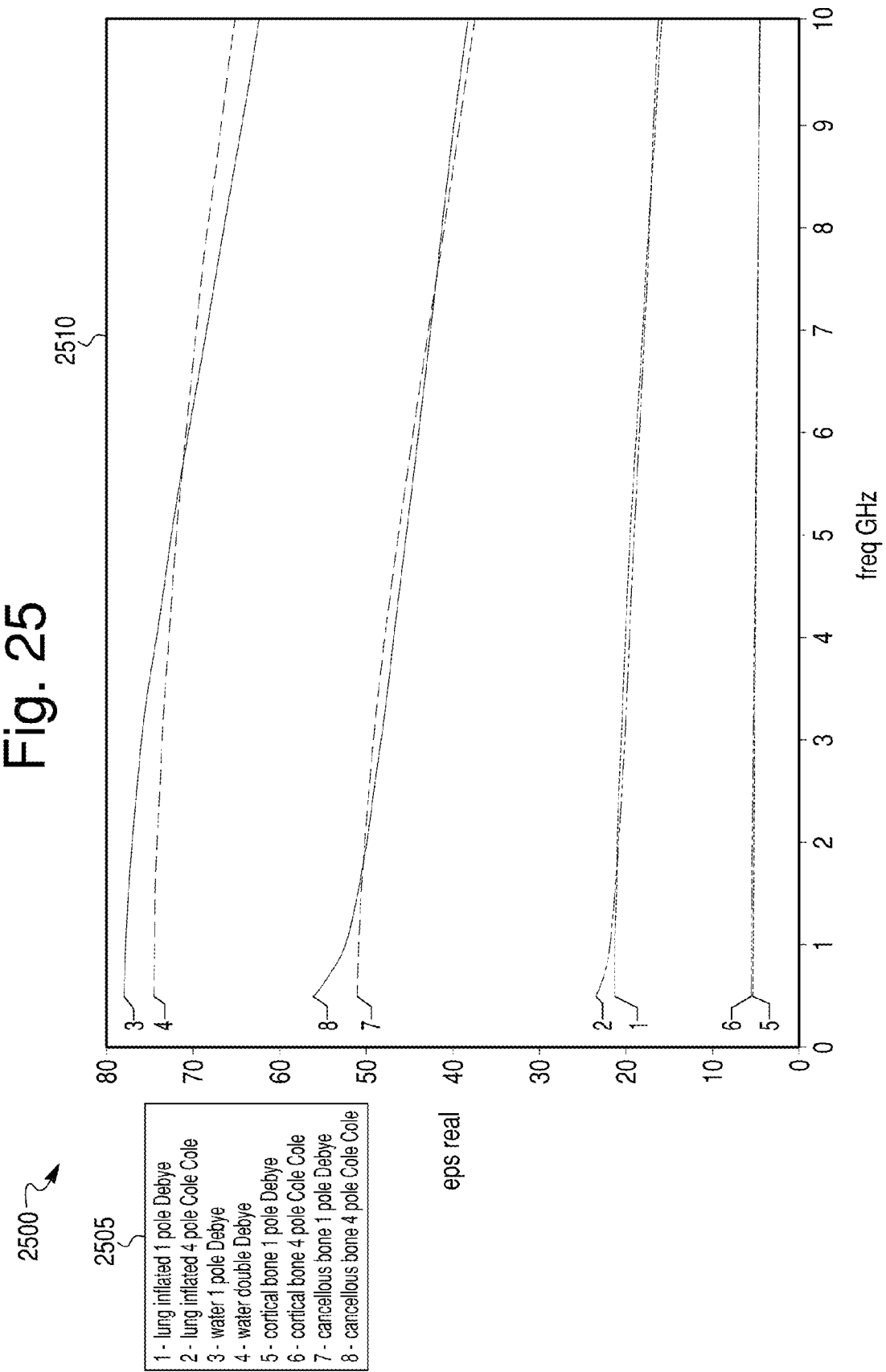
FIG. 25 is a graph which shows real permittivity according to an exemplary comparison between the four-pole Cole-Cole curves and one-pole Debye curves over the frequency range from 500 MHz to 10 GHz between inflated lung, water, cancellous bone, and cortical bone.
Figure 26:
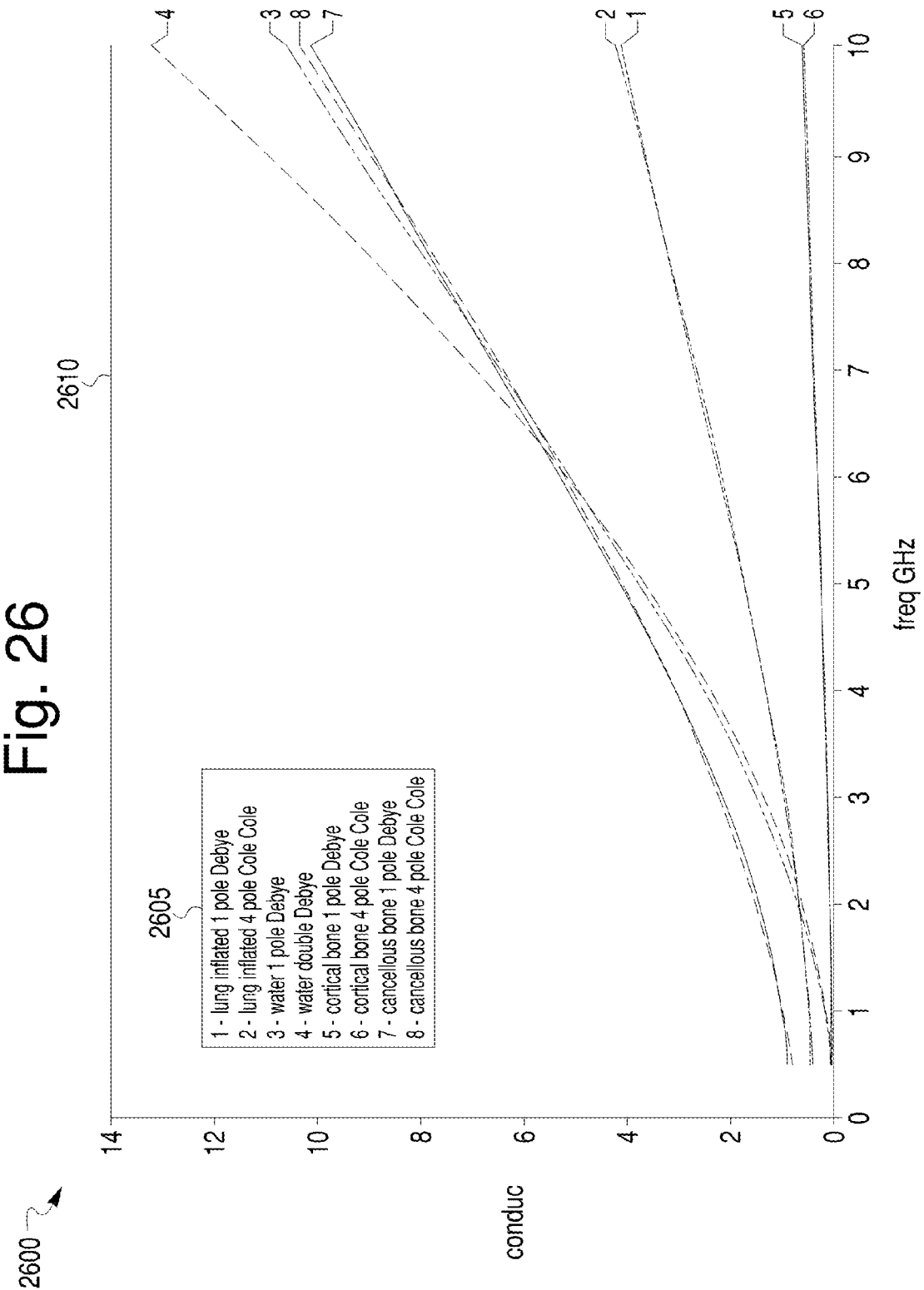
FIG. 26 is a graph which shows conductivity versus frequency for the four-pole Cole-Cole model and the one-pole Debye model over the frequency range from 500 MHz to 10 GHz for inflated lung, water, cancellous bone, and cortical bone.

In an embodiment, it is possible to tune the minimum $\in_s$ parameter and incremental values. As mentioned previously, increasing the frequency decreases the dynamic range of the real permittivity and decreasing the frequency increases the dynamic range of the real permittivity. FIG. 25 is a graph 2500 showing a comparison 2510 between the four-pole Cole-Cole curves and one-pole Debye curves over the frequency range from 500 MHz to 10 GHz between inflated lung, water, cancellous bone, and cortical bone 2505. The accuracy of the fit for the Debye model can be increased by generating higher order Debye models such as a two-pole Debye model or three-pole Debye model. FIG. 26 is a graph 2600 showing conductivity versus frequency 2610 for the four-pole Cole-Cole model and the one-pole Debye model for the four tissues 2605 of interest.

Example III

Converting from Hounsfield Encoded Image to a Dielectric Encoded Image in Terms of Debye Parameters An example of converting from a Hounsfield encoded unit in an image to a dielectric encoded unit in an image (in terms of one-pole Debye parameters) for lung inflated and for cancellous bone is now presented. Initially, the Hounsfield units falling between −1024 to 3071 are converted to pixel values falling from 0 to 4095 by adding 1024 to all Hounsfield units. For lung inflated, if pixel values fall between (and including) 184 and 833 then the pixel value is converted to one-pole Debye parameters $$D_{out}\_eps\_inf(x,y) = eps\_inf\_lung\_inflated$$

$$D_{out}\_eps\_s(x,y) = eps\_s\_lung\_inflated(P_{in}(x,y)-183)$$

$$D_{out}\_tau(x,y) = tau\_lung\_inflated$$

$$D_{out}\_sigma(x,y) = sigma\_lung\_inflated(P_{in}(x,y)-183)$$

Where $P_{in}(x, y)$ refers to the pixel value at Cartesian coordinate (x,y) which in this case would be somewhere between and including 184 and 833. In this example, $P_{in}(x, y)-183$ takes on an index value ranging from 1 to 650. The values of eps_inf_lung_inflated, eps_s_lung_inflated, tau_lung_inflated, and sigma_lung_inflated are presented according to Table VII; however, eps_s_lung_inflated and sigma_lung_inflated are allowed to vary and therefore an index value has been used to track these parameters.

Specifically eps_inf_lung_inflated=7.692 and tau_lung_inflated=1.3E−11. In the case of eps_s_lung_inflated for $P_{in}$ (x,y)=184, the index value is 1, and this corresponds to 19.1034 which is the minimum $\in_s$ parameter also equal to 21.226*0.9.

When $P_{in}$ (x,y)=185, the index value is 2, and this corresponds to 19.1067 which is equal to 21.226*(0.9+0.000154083204931043*1). When $P_{in}$ (x,y)=833, the index value is 650, and this corresponds to 21.226 which is equal to 21.226*(0.9+0.000154083204931043*649). In the case of sigma_lung_inflated for $P_{in}$ (x,y)=184, the index value is 1, and this corresponds to 0.3789, which is also equal to 0.421*0.9. When $P_{in}$ (x,y)=185, the index value is 2, and this corresponds to 0.378964869029276 which is equal to 0.421*(0.9+0.000154083204931043*1). When $P_{in}$ (x,y)=833, the index value is 650, and this corresponds to 0.421 which is equal to 0.421*(0.9+0.000154083204931043*649).

A more general form can be written for $D_{out}\_eps\_s(x, y)$ $$D_{out}\_eps\_s(x,y) = eps\_s*[start\_incr+incr*(i-1)]$$

Where i is the index value found from $P_{in}$ (x, y)−minimum_range_of_tissue. In the case of lung inflated, $$D_{out}\_eps\_s(x,y) = 21.226*[0.9+0.000154083204931043*(i-1)]$$

Where i is the index value found from $P_{in}(x, y)-183$. A more general form can also be written for $D_{out}\_sigma(x, y)$ $$D_{out}\_sigma(x,y) = sigma*[start\_incr+incr*(i-1)]$$

In the case of lung inflated, $$D_{out}\_sigma(x,y) = 0.421*[0.9+0.000154083204931043*(i-1)]$$

Where i is found from the index value $P_{in}(x, y)-183$.

An example, based on an embodiment, of converting from a Hounsfield unit to Debye parameters is presented below in the case of the tissue lung inflated.

For example if $H_{in}(x, =-700$ then $$P_{in}(x, y) = H_{in}(x, y) + 1024 = -700 + 1024 = 324.$$

$$D_{out}\_eps\_inf(x, y) = 7.692$$

$$D_{out}\_eps\_s(x, y) =$$

$$eps\_s\_lung\_inflated(324-183) = eps\_s\_lung\_inflated(141)$$

$$D_{out}\_tau(x, y) = 1.3E-11$$

$$D_{out}\_sigma(x, y) =$$

$$sigma\_lung\_inflated(324-183) = sigma\_lung\_inflated(141)$$

Where eps_s_lung_inflated(141) =

$$21.226*(0.9+0.000154083204931043*140) = 19.5613$$

and sigma_lung_inflated(141) =

$$0.421*(0.9+0.000154083204931043*140) = 0.387982$$

Now the four one-pole Debye parameters correspond to the Hounsfield unit of −700. The one-pole Debye equation can be used to calculate the complex permittivity (dielectric values) at a frequency and/or frequencies of interest. The one-pole Debye equation in this case becomes $$\varepsilon(\omega) = 7.692 + \frac{19.5613 - 7.692}{1 + j\omega*1.3E-11} + \frac{0.387982}{j\omega\varepsilon_0}$$

If the frequency of interest is 500 MHz, then $$\omega = 2*\pi*f$$

$$f = 500*10^6 \text{ Hz (500 MHz)}$$

$$\varepsilon_0 = 8.85*10^{\wedge} -12$$

$$\varepsilon = 7.692 + \frac{19.5613 - 7.692}{1 + j*2*\pi*500*10^6*1.3E-11} + \frac{0.387982}{j*2*\pi*500*10^6*8.85*10^{\wedge}-12}$$

$$= 19.541535411662380 - 14.438576850030330\, i$$

If the frequency of interest is 10 GHz, then $$\omega = 2*\pi*f$$

$$f = 10*10^9 \text{ Hz (10 GHz)}$$

$$\varepsilon_0 = 8.85*10^{\wedge} -12$$

$$\varepsilon = 7.692 + \frac{19.5613 - 7.692}{1 + j*2*\pi*10*10^9*1.3E-11} + \frac{0.387982}{j*2*\pi*10*10^9*8.85*10^{\wedge}-12}$$

$$= 14.811364777554054 - 6.512929135474326\, i$$

For cancellous bone, if pixel values fall between (and including) 1144 and 1323 then the pixel value is converted to one-pole Debye parameters as demonstrated below.

$$D_{out\_eps\_inf}(x,y) = eps\_inf\_\text{cancellous bone}$$

$$D_{out\_eps\_s}(x,y) = eps\_s\_\text{cancellous bone}(-P_{in}(x,y)+1323)$$

$$D_{out\_tau}(x,y) = tau\_\text{cancellous bone}$$

$$D_{out\_sigma}(x,y) = sigma\_\text{cancellous bone}(-P_{in}(x,y)+1323)$$

Where Pin(x,y) refers to the pixel value which in this case would fall in the range between and including 1144 and 1323. In this way Pin(x,y)=1143 takes on an index value ranging from 1 to 180.

The values of eps_inf_cancellous bone, eps_s_ cancellous bone, tau_ cancellous bone, and sigma_ cancellous bone are presented according to Table VII; however, eps_s_ cancellous bone and sigma_ cancellous bone are allowed to vary and therefore an index value has been used to track these parameters.

Specifically, eps_inf_cancellous bone=4.056, tau_inf_cancellous bone=1.3E−11. In the case of eps_s_cancellous bone for Pin(x,y)=1144, the index value is 179, and this corresponds to 18.539 which is the ∈s parameter. When Pin (x,y)=1145, the index value is 178, and this corresponds to 18.5286 which is equal to 18.539*(0.9+0.000558659217877011*178). When Pin(x, y)= 1323, the index value is 0, and this corresponds to 16.6851 which is equal to 18.539*0.9 and also equal to the minimum ∈s parameter. In the case of sigma_cancellous bone for Pin(x,y)=1144, the index value is 179, and this corresponds to 0.332, which is the σS parameter. When Pin (x,y)=1145, the index value is 178, and this corresponds to 0.33181 which is equal to 0.332*(0.9+0.000558659217877011*178). When Pin(x,y)=1323, the index value is 0, and this corresponds to 0.2988 which is equal to 0.332*0.9.

A more general form can be written for D_out_eps_s(x,y)

$$D_{out\_eps\_s}(x,y) = eps\_s*[stop\_incr+incr*j]$$

Where j is the index value found from −Pin(x,y)+maximum_range_of_tissue. In the case of cancellous bone, $$D_{out\_eps\_s}(x,y) = 18.539*[0.9+0.000558659217877011*j]$$

Where j is the index value found from −P_in(x,y)+1323.

An example of converting from a Hounsfield unit to Debye parameters in the case of cancellous bone, according to embodiment, is presented below.

For example if H_in(x,y)=200 then, $$P_{in}(x, y) = H_{in}(x, y) + 1024$$
$$= 200 + 1024$$
$$= 1224.$$

$$D_{out\_eps\_inf}(x, y) = 4.056$$

$$D_{out\_eps\_s}(x, y) = eps\_s\_\text{cancellous bone}(-1224 + 1323)$$
$$= eps\_s\_\text{cancellous bone}(99)$$

$$D_{out\_tau}(x, y) = 1.3E - 11$$

$$D_{out\_sigma}(x, y) = sigma\_\text{cancellous bone}(-1224 + 1323)$$
$$= sigma\_\text{cancellous bone}(99)$$

Where, eps_s_cancellous bone(99)=18.539*(0.9+0.000558659217877011*99)=17.71044 and sigma_cancellous bone(99)=0.332*(0.9+0.000558659217877011*99)=0.317162

Based on the example presented above, four one-pole Debye parameters corresponding to the Hounsfield unit of 200 have now been established. The one-pole Debye equation can be used to calculate the complex permittivity (dielectric values) at a frequency and/or frequencies of interest. The one-pole Debye equation in this case becomes $$\varepsilon(\omega) = 4.056 + \frac{17.71044 - 4.056}{1 + j\omega*1.3E - 11} + \frac{0.317162}{j\omega\varepsilon_0}$$

If the frequency of interest is 500 MHz, then $$\omega = 2*\pi*f$$
$$f = 500*10^6 \text{Hz}(500 \text{ MHz})$$
$$\varepsilon_0 = 8.85*10^\wedge - 12$$
$$\varepsilon = 4.056 + \frac{17.71044 - 4.056}{1 + j*2*\pi*500*10^6*1.3E - 11} + \frac{0.317162}{j*2*\pi*500*10^6*8.85*10^\wedge - 12}$$
$$= 17.687702822105706 - 11.964163388757955\,i$$

If the frequency of interest is 10 GHz, then $$\omega = 2*\pi*f$$
$$f = 10*10^9 \text{Hz}(10 \text{ GHz})$$
$$\varepsilon_0 = 8.85*10^\wedge - 12$$
$$\varepsilon = 4.056 + \frac{17.71044 - 4.056}{1 + j*2*\pi*10*10^9*1.3E - 11} + \frac{0.317162}{j*2*\pi*10*10^9*8.85*10^{-12}}$$
$$= 12.246115608605830 - 7.260173579392962\,i$$

Similar types of equations to convert between Hounsfield units and one-pole Debye parameters can be written for the other tissues in Table VII. It is important to draw the distinction between two different groups of tissues: 1) those of tissues of air, inflated lung, and fat and 2) those of tissues of water, muscle region high, muscle region median, muscle region low, cancellous bone, and cortical bone. In the case of group 1, the eps_s and sigma Debye parameters are allowed to vary from a minimum at lower pixel values to a maximum at higher pixel values in each pixel value range of each tissue. In the case of group 2, the opposite is true as the eps_s and sigma Debye parameters are allowed to vary from a maximum at lower pixel values to a minimum at higher pixel values in each pixel value range of each tissue.

Figure 27:
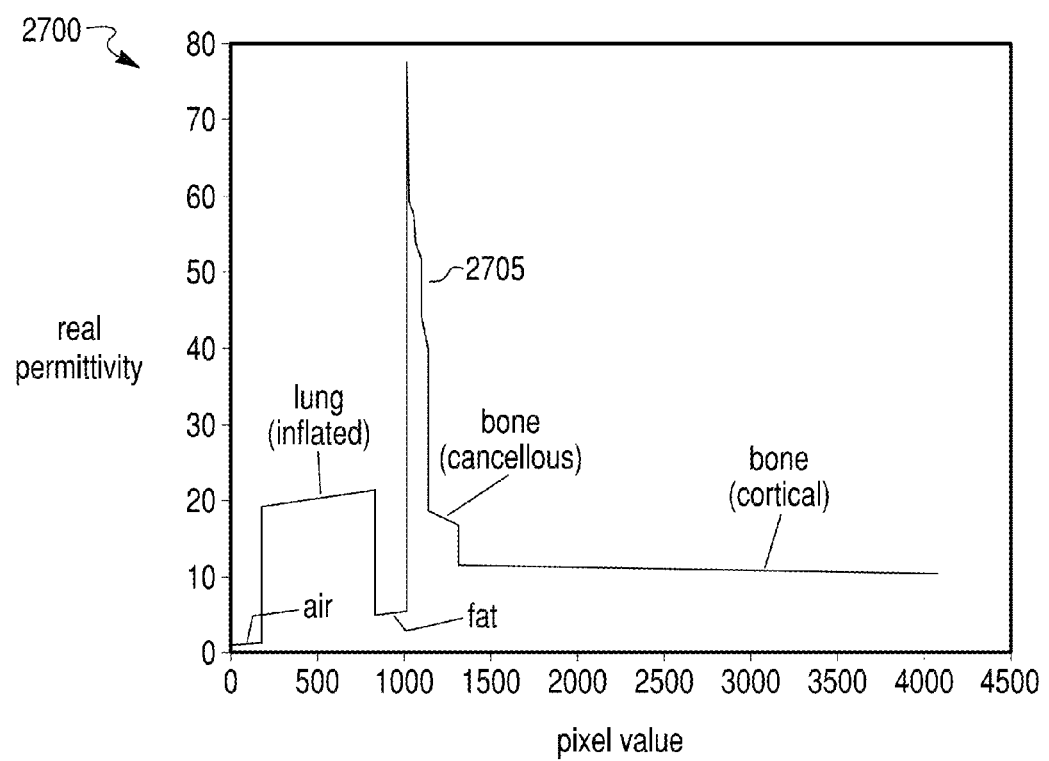
FIG. 27 is a graph which shows the relationship between real permittivity and pixel values based on the tissues listed in Table V in accordance with an embodiment at 500 MHz.
Figure 28:
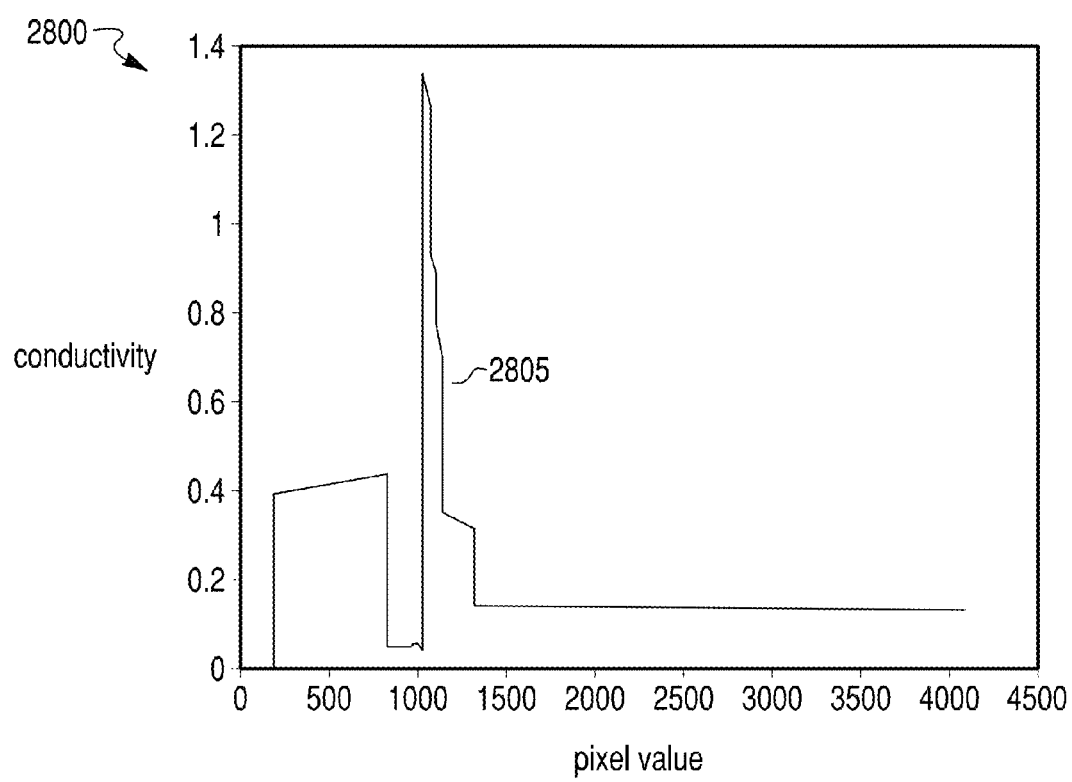
FIG. 28 is a graph which shows the relationship between conductivity and pixel values based on the tissues listed in Table V in accordance with an embodiment at 500 MHz.
Figure 29:
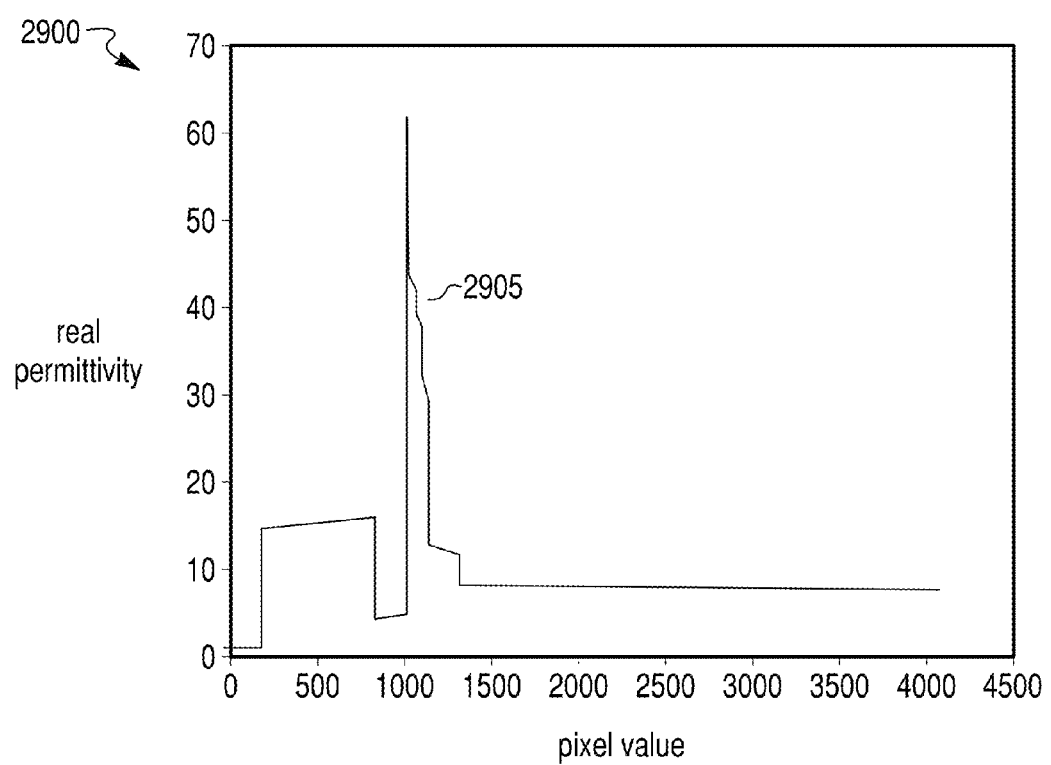
FIG. 29 is a graph which shows the relationship between real permittivity and pixel values based on the tissues listed in Table V in accordance with an embodiment at 10 GHz.
Figure 30:
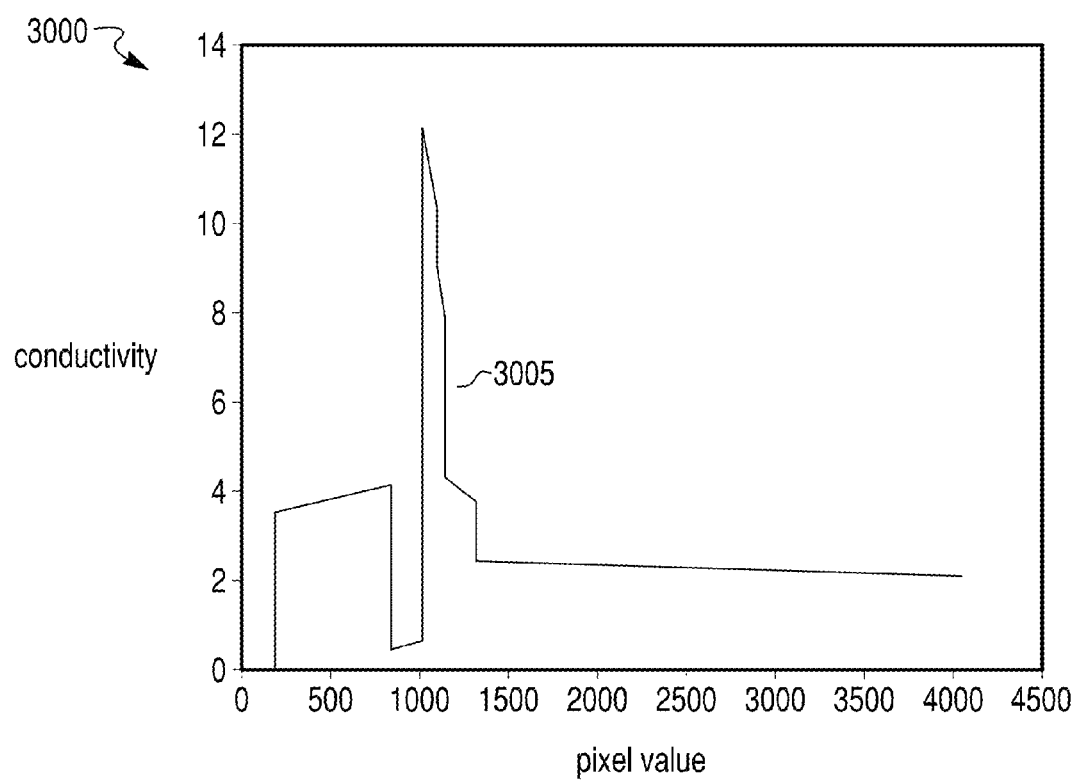
FIG. 30 is a graph which shows the relationship between conductivity and pixel values based on the tissues listed in Table V in accordance with an embodiment at 10 GHz.

FIG. 27 and FIG. 28 are graphs 2700, 2800 that show the relationship between real permittivity and pixel values and conductivity and pixel values, respectively, using the information provided in Table VII at 500 MHz. Some of the tissues (or tissue groups) have been labeled in FIG. 27. Upon inspecting FIG. 27 and looking at the real permittivity ranges for each tissue or tissue group, one can see that these ranges for the real permittivity are all non-overlapping. The increment values including the start and stop increment in Table VII were chosen to accomplish this. FIG. 29 and FIG. 30 are graphs 2900, 3000 that show the relationship between real permittivity and pixel values and conductivity and pixel values, respectively, using the information provided in Table VII at 10 GHz.

Example IV

Converting from Dielectric Encoded Images to Hounsfield Encoded Images in Terms of Debye Parameters According to an embodiment, it is possible to convert from a dielectric encoded unit in an image (in terms of the Debye parameters) to a Hounsfield encoded unit in an image. An example of this process is presented below for lung inflated and for cancellous bone.

Initially, the range of the eps_s of each tissue is determined. For lung inflated, the range has been determined to fall between 19.1034 to 21.226. These values are shown directly in Table VII. In this case 21.226, corresponds to eps_s presented in Table VII which came from the fitting process described earlier. In this case 19.1034, corresponds to the minimum eps_s presented in Table VII. This is based on the start increment of 0.9, the increment value of 0.000154083204931043, and the (833−184+1)=650 different pixel values (or Hounsfield units) which fall within lung inflated. If the range of eps_s falls between and including 19.1034 to 21.226, then the tissue is identified as lung (inflated) tissue and the following formula can be used to convert to a pixel value.

$$P_{out}(x, y) = \frac{(D_{in\_eps\_s}(x, y) - 19.1034)}{21.226} * \frac{1}{incr} + 184$$

Where in this case incr=0.000154083204931043 and hence, $$P_{out}(x, y) = \frac{(D_{in\_eps\_s}(x, y) - 19.1034)}{21.226} * \frac{1}{0.000154083204931043} + 184$$

For example, if $D_{in\_eps\_s}(x,y)=19.5613$, then $$P_{out}(x, y) = \frac{(19.5613 - 19.1034)}{21.226} * \frac{1}{0.000154083204931043} + 184 \sim$$
$$= 324$$

In this example, eps_s is used to identify tissue type and a difference in eps_s of 19.5613−19.1034 (along with the maximum eps_s of 21.226, current Hounsfield unit of 184, and incr value of 0.000154083204931043) is used to calculate a pixel value; however the other parameters in Table VII or a combination of parameters may be used for these purposes. In this case $P_{out}(x, y)$ is not necessarily integer so $P_{out}(x, y)$ can, in an embodiment, be rounded to the nearest integer which in this case is 324. Now to convert the pixel value to Hounsfield units we subtract 1024 to arrive at −700.

$$H_{out}(x,y) = P_{out}(x,y) - 1024$$

$$H_{out}(x,y) = 324 - 1024 = -700$$

For cancellous bone, the range of eps_s is 16.6851 to 18.539. These values are shown directly in Table VII. In this case 18.539, corresponds to eps_s presented in Table VII which came from the fitting process described earlier. In this case 16.6851 corresponds to the minimum eps_s presented in Table VII. This is based on the stop increment of 0.9, the increment value of 0.000558659217877011, and the (1323−1144+1)=180 different pixel values (or Hounsfield units) which fall within lung inflated. If the range of eps_s falls between and including 16.6851 to 18.539 then the following formula can be used to convert to a pixel value.

$$P_{out}(x, y) = \frac{(D_{in\_eps\_s}(x, y) - 18.539)}{18.539} * \frac{1}{incr} + 1144$$

Where in this case incr=0.000558659217877011, hence $$P_{out}(x, y) = \frac{(-D_{in\_eps\_s}(x, y) + 18.539)}{18.539} * \frac{1}{0.000558659217877011} + 1144$$

For example if eps_s_cancellous bone(99)=17.71044

$$P_{out}(x, y) = \frac{(-17.71044 + 18.539)}{18.539} * \frac{1}{0.000558659217877011} + 1144$$
$$= 1224$$

In this case $P_{out}(x, y)$ is not necessarily integer so $P_{out}(x, y)$ can be rounded to the nearest integer which in this case is 1224. Now to convert the pixel value to Hounsfield units, 1024 is subtracted to arrive at 200.

$$H_{out}(x,y) = P_{out}(x,y) - 1024$$

$$H_{out}(x,y) = 1224 - 1024 = 200$$

Similar types of equations to convert between one-pole Debye parameters and Hounsfield units can be written for the other tissues in Table VII. It is important to draw the distinction between two different groups of tissues: 1) those of tissues of air, inflated lung, and fat and 2) those of tissues of water, muscle region high, median, and low, cancellous bone, and cortical bone. In the case of group 1, the eps_s and sigma Debye parameters are allowed to vary from a minimum at lower pixel values to a maximum at higher pixel values in each pixel value range of each tissue. In the case of group 2, the opposite is true as the eps_s and sigma Debye parameters are allowed to vary from a maximum at lower pixel values to a minimum at higher pixel values in each pixel value range of each tissue. Hence the form of the equation between group 1 and group 2 when converting to pixel values from Debye parameters can be different as shown previously with the two examples of lung inflated and cancellous bone tissues.

In the examples above, the conversion from Debye parameters to Hounsfield units and vice versa, has been presented according to an embodiment. In another embodiment, it is also possible, as indicated in FIG. 18, to start the process from a series of RAW dielectric values taken at different frequencies. With the known frequency under which each of the RAW dielectric values has been collected, it is possible to then convert the RAW dielectric values to Debye parameters. This conversion can be carried out in a similar fashion to determine the one-pole Debye parameters based on the four-pole Cole-Cole parameters.

Figure 31:
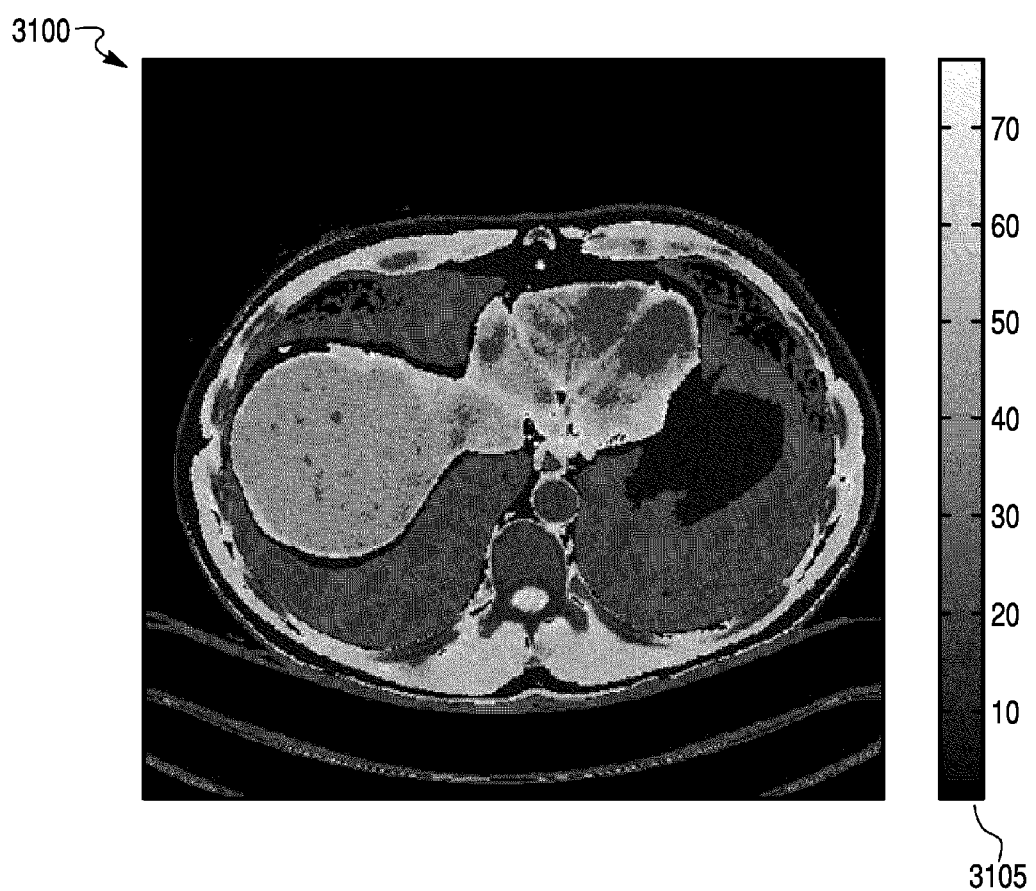
FIG. 31 shows the CT image from FIG. 12 converted from Hounsfield units to real permittivity at 500 MHz according to an embodiment.
Figure 32:
FIG. 32 shows the CT image from FIG. 12 converted from Hounsfield units to conductivity at 500 MHz according to an embodiment.
Figure 33:
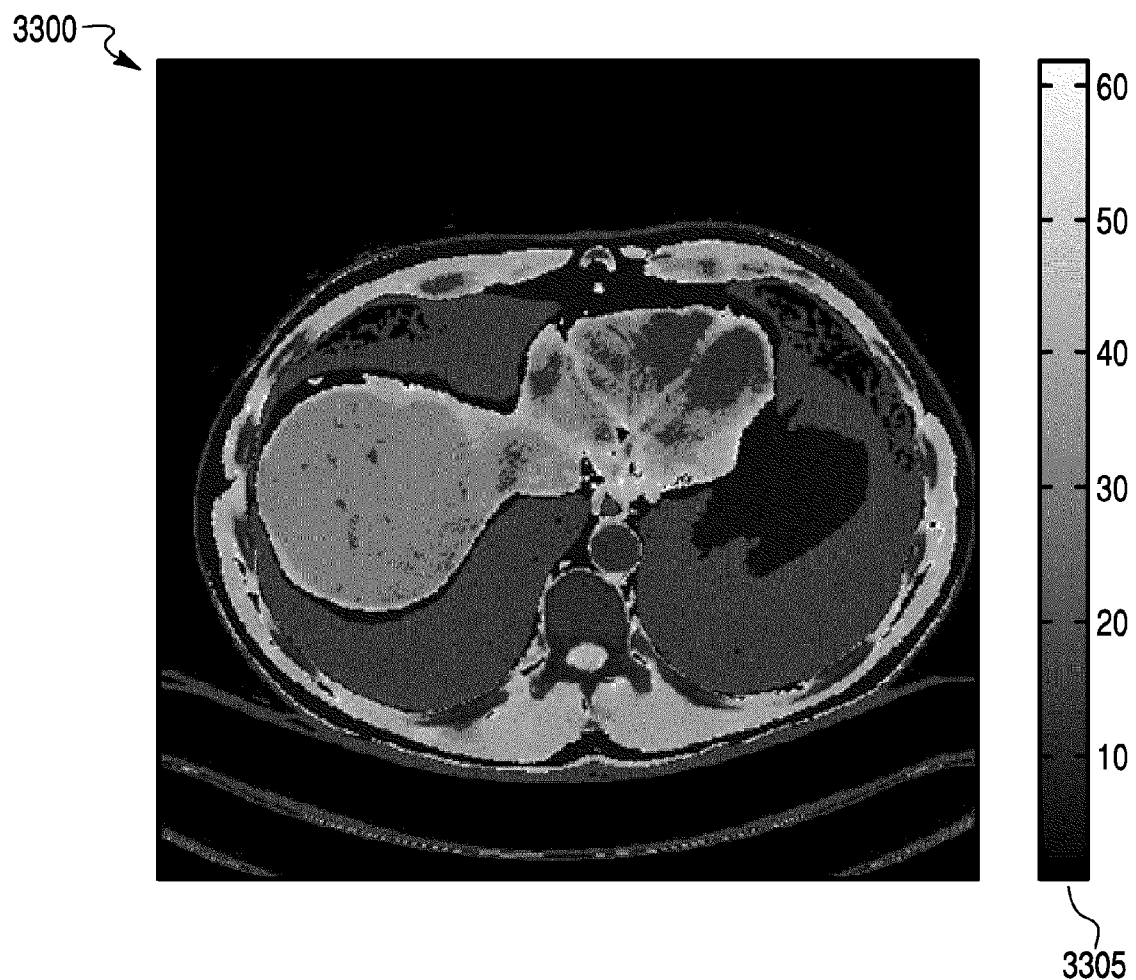
FIG. 33 shows the CT image from FIG. 12 converted from Hounsfield units to real permittivity at 10 GHz according to an embodiment.
Figure 34:
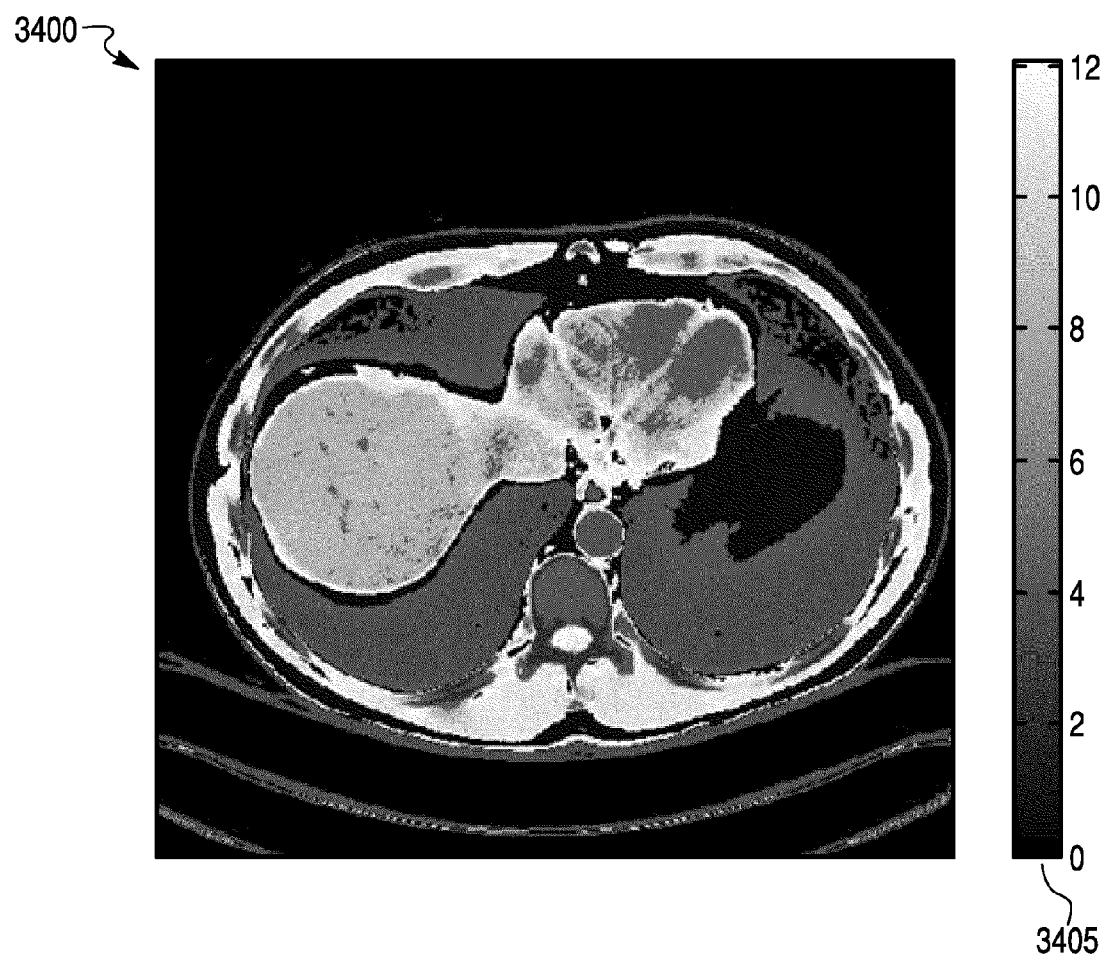
FIG. 34 shows the CT image from FIG. 12 converted from Hounsfield units to conductivity at 10 GHz according to an embodiment.

As discussed previously, FIG. 12 shows an example of a CT image in Hounsfield units. FIG. 31 is an image 3100 showing the CT image from FIG. 12 converted from Hounsfield units to real permittivity 3105 at 500 MHz according to the embodiment described previously with the reduced tissue dataset as in Table VII. FIG. 32 is an image 3200 showing this CT image from FIG. 12 converted from Hounsfield units to conductivity 3205 at 500 MHz according to the embodiment described previously with the reduced tissue dataset as in Table VII. FIG. 33 is an image 3300 showing this CT image from FIG. 12 converted from Hounsfield units to real permittivity 3305 at 10 GHz according to the embodiment described previously with the reduced tissue dataset as in Table VII. FIG. 34 is an image 3400 showing this CT image from FIG. 12 converted from Hounsfield units to conductivity 3405 at 10 GHz according to the embodiment described previously with the reduced tissue dataset as in Table VII. According to an embodiment described previously, it is then possible to convert images displayed in real permittivity and conductivity back to the original image as shown in FIG. 12.

Raw Dielectric Images to MRI Intensity Images Conversion

A process for converting RAW dielectric images to MRI intensity encoded images has been presented in FIGS. 3 and 7. A calculation for converting RAW dielectric images to MRI intensity encoded, which illustrates an embodiment of the present image processing system 100, is presented below.

The water content fw can be obtained from the real permittivity, $\in_{0.1}$ at 100 MHz (based on Schepps J. L. and K. R. Foster. The UHF and microwave dielectric properties of normal and tumour tissues: variation in dielectric properties with tissue water content and Phys. Med. Biol. vol. 25, pp. 1149-1159, 1980, and Smith, S. R. and K. R. Foster. Dielectric properties of low-water content tissues. Phys. Med. Biol. vol. 30, pp. 965-973, 1996, the entire contents of both of these publications are incorporated herein by reference), where $$P = \frac{2\varepsilon_w\varepsilon_w + \varepsilon_w\varepsilon_p - 2\varepsilon_{0.1}\varepsilon_w - \varepsilon_{0.1}\varepsilon_p}{\varepsilon_{0.1}(\varepsilon_w - \varepsilon_p) + 2\varepsilon_w(\varepsilon_w - \varepsilon_p)}$$

The water content $fw=1-P$, $\in_w$, and $\in_p$ are taken to be the maximum and minimum real permittivity upon inspecting all possible tissues in the database by Gabriel et al. (1996) at 100 MHz which are 98.0940 and 5.6903 respectively. The water content is then related to the T1 values (based on Fatouros, P. P., and A. Marmarou. Use of magnetic resonance imaging for in vivo measurements of water content in human brain: method and normal values. J. Neursurg. Vol. 90, pp. 109-115, 1999, whose entire contents are incorporated herein by reference) which depends on three different intervals for P.

$$T1 = \frac{A_{11}}{\frac{1}{f_w} - B_{11}} \quad P \le 0.35$$

$$T1 = \frac{A_{12}}{\frac{1}{f_w} - B_{12}} \quad P \ge 0.9$$

$$T1 = \frac{A_{11}}{\frac{1}{0.65} - B_{11}} * (1 - \text{weight}) + \frac{A_{12}}{\frac{1}{0.1} - B_{12}} * (\text{weight}) \quad 0.35 < P < 0.9$$

Where $A_{11}, A_{12}, B_{11}, B_{12}$ are parameters that relate T1 values to the water content. In an embodiment $A_{11}=0.9, A_{12}=2.9$, and $B_{11}=B_{12}=0.915$.
Where $$\text{weight} = \frac{f_w - 0.35}{0.9 - 0.35}$$

Once T1 is obtained, the equation for the ratio image is used to determine the corresponding ratio image intensity for each T1 value.

$$I_{ratio} = k_{ratio} \frac{\left(1 - 2e^{-\frac{TR_{short} - \frac{TE}{2}}{T1}} + e^{-\frac{TR_{short}}{T1}}\right)}{\left(1 - 2e^{-\frac{TR_{long} - \frac{TE}{2}}{T1}} + e^{-\frac{TR_{long}}{T1}}\right)}$$

In an embodiment $k_{ratio}=1.04$, $TR_{short}=0.45$ s, $TR_{long}=2.1$ s, and TE=0.018 s. MRI scanner acquisition parameters including, but not limited to, the MRI sequence, repetition time (TR), and echo time (TE) would be defined by manually by the user or in computing environment 102. The parameters $k_{ratio}$, A, and B would also be defined manually by the user or in computing environment 102, and would be expected to have a relationship between the other MRI scanner acquisition parameters.

Figure 15:
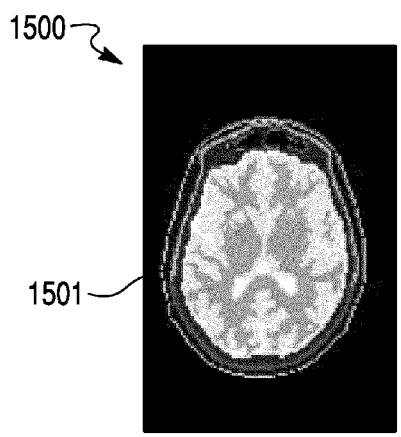
FIG. 15 shows the real permittivity of a dielectric image.
Figure 16:
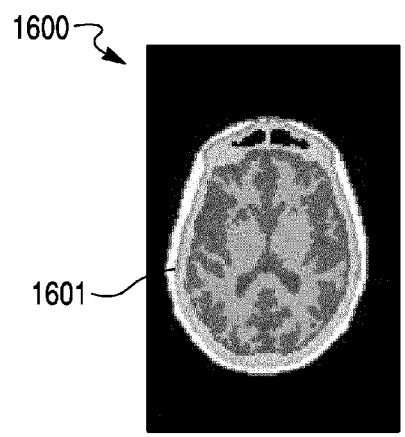
FIG. 16 shows the MRI encoded image converted from the real permittivity of a dielectric image in accordance with a present embodiment.

As an illustrative example, a head slice from the Duke model at 2 mm from Christ et al. (Christ, A. and et al. The Virtual Family—development of surface-based anatomical models of two adults and two children for dosimetric simulations. Physics in Medicine and Biology, vol. 55, pp. N23-N38, 2010) was used and the tissues have been assigned real permittivity and conductivity values based on Gabriel et al. (1996). FIG. 15 shows the real permittivity 1501 of this Duke model for the head slice. FIG. 16 shows the MRI ratio image intensity 1601 of the image in FIG. 15 after converting the real permittivity to water content, then to T1 values, and then to ratio image intensity values as an embodiment of the present image processing system 100. The spin echo image equation, presented previously, can be used with a selected repetition time, TR, to recover the MRI image intensity.

$$I = k\alpha\rho e^{-\frac{TE}{T2}} \left(1 - 2e^{-\frac{TR - \frac{TE}{2}}{T1}} + e^{-\frac{TR}{T1}}\right)$$

Due to the nature of an MRI image being dependent on the MRI method used, there are different ways to go about converting from dielectric values to MRI signal intensity images that are feasible. The above outlined a method but assumed a spin echo sequence with two different repetition times, an echo time, a $k_{ratio}$, and different A and B values in the water content equation related to T1. The latter three parameters are scanner specific. These values can change depending on the preferred output appearance of the MRI image to be created. Regarding the repetition times and echo times, these can be defined by the user and/or the computing environment 102 and are based on the specific preferences of how an image is to appear.

In other embodiments, other MRI sequences are possible and the presented process is not limited to the use of spin-echo sequences (Bernstein, M. A., K. F. King, and X. J. Zhou. Handbook of MRI Pulse Sequences. Elsevier. 2004, and Cavagnaro, M, F. Frezza, R. Laurita, F. Mangini, and A. Palombo. From Magnetic Resonance Imaging to Dielectric Properties of Tissues. Biophysics & Bioeng. Letters. Vol. 4. 2011). For example, it is possible to utilize an inversion recovery fast spin echo sequence, as presented in Zhu and Penn (2005), with the present image processing system 100 to create MRI intensity images (Zhu, D. C. and R. D. Penn. Full-Brain T1 Mapping Through Inversion Recovery Fast Spin Echo Imaging with Time-Efficient Slice Ordering. Magnetic Resonance in Medicine. Vol. 54, pp. 725 731. 2005 and Zhu, D. C., A. A. Linninger, and R. D. Penn. Brain Water Content Measurement and Visualization with Applications to Hydrocephalus. Proc. Intl. Soc. Mag. Reson. Med. 13. Pg. 1099. 2005). In other embodiments, other relationships between water content and an MRI image can be utilized (Neeb, H., K. Zilles, and N. J. Shah. A new method for fast quantitative mapping of absolute water content in vivo. NeuroImag. vol. 31, pp. 1156-1168. 2006). In other embodiments, different methods to generate T1 maps from MRI images can be utilized (Messroghil, D. R. and et al. An open-source software tool for the generation of relaxation time maps in magnetic resonance imaging. BMC Medical Imaging, vol. 10. No. 16, 2010). The entire contents of all of these publications are incorporated herein by reference for the MRI techniques disclosed therein.

The invention is not limited to the embodiments described above. Instead, many other variations of the invention are within the scope and spirit of the invention. For example, techniques described above may be used to convert to other types of data that are similar to or equivalent to Hounsfield data, such as other forms of representing tissue that are related to density. In addition, other forms of representation of CT and MRI image data can be used in the conversion process techniques described. As another example, the use of remote acquisition sites and a centralized computing environment described above for dielectric to Hounsfield conversion can be used for the CT and MRI conversions described herein. The invention is therefore defined with reference to the following claims.

TABLE I

| Tissue | CT Number (Hounsfield Unit) | Complex Permittivity | Real Permittivity Increment |
| --- | --- | --- | --- |
| Air | "−1024 to −840" | $1 + 0j$ | 0.001 |
| Lung (Inflated) | "−840 to −190" | $24.7727 - 21.3530i$ | 0.0005 |
| Adipose Tissue (Fat) | "−190 to −51" | $5.6340 - 2.3708i$ | 0.001 |
| Yellow Marrow (Bone Marrow) | "−51 to −8" | $5.7585 - 1.6699i$ | 0.005 |
| Breast/Fat Tissue | "−8 to −4" | $5.5418 - 1.9601i$ | 0.02 |
| Water | "−4 to +8" | $74.1933 - 0.8222i$ | 0.02 |
| Cerebro Spinal Fluid | "8 to 20" | $72.734 - 133.29i$ | 0.02 |
| Small Intestine | "20 to 26" | $69.767 - 110.29i$ | 0.02 |
| Gall Bladder Bile | "26 to 27.5" | $74.886 - 100.04i$ | 0.02 |
| Lymph | "27.5 to 30" | $62.4484 - 51.0040i$ | 0.02 |
| Pancreas | "30 to 33" | $62.4484 - 51.0040i$ | 0.02 |
| Prostate | "33 to 34" | $62.4484 - 51.0040i$ | 0.02 |
| White Matter | "34 to 35" | $63.3152 - 81.9712i$ | 0.02 |
| Testis | "35 to 37" | $64.8368 - 59.5446i$ | 0.02 |
| Gray Matter | "37 to 40" | $60.0216 - 41.4872i$ | 0.02 |
| Thyroid | "40 to 40.5" | $62.5784 - 51.0040i$ | 0.02 |
| Muscle | "40.5 to 42" | $58.2011 - 46.1678i$ | 0.02 |
| Stomach | "42 to 42.5" | $68.7113 - 58.2419i$ | 0.02 |
| Kidney | "42.5 to 43" | $70.4850 - 61.2619i$ | 0.02 |
| Aorta | "43 to 44" | $48.3209 - 32.1777i$ | 0.02 |
| Lung Deflated | "44 to 45" | $56.1892 - 38.8821i$ | 0.02 |
| Ovary | "45 to 46" | $61.3000 - 56-6877i$ | 0.02 |
| Heart | "46 to 47" | $69.3075 - 54.1774i$ | 0.02 |
| Eye Lens | "47 to 51" | $48.9513 - 38.8161i$ | 0.02 |
| Trachea | "51 to 54" | $45.3067 - 36.6066i$ | 0.02 |
| Spleen | "54 to 54.5" | $66.4910 - 58.0643i$ | 0.02 |
| Blood | "54.5 to 57" | $65.6503 - 78.8589i$ | 0.02 |
| Liver | "57 to 66" | $53.5121 - 36.5413i$ | 0.01 |
| Skin | "66 to 90" | $49.8211 - 38.4200i$ | 0.01 |
| Cartilage | "90 to 120" | $46.7743 - 33.1049i$ | 0.005 |
| Cancellous Bone (Spongiosa) | "120 to 300" | $23.1628 - 12.9158i$ | 0.001 |
| Cortical Bone | "300 to 3000" | $13.4390 - 4.9529i$ | 0.0001 |

TABLE II

| Tissue Type (Table 1 - dielectric to Hounsfield conversion) | Tissue Type (Gabriel 1996) |
|---|---|
| Aorta | Aorta |
| — | Bladder |
| Blood | Blood |
| Cancellous Bone (Spongiosa) | Bone (Cancellous) |
| Cortical Bone | Bone (Cortical) |
| — | Bone Marrow (Infiltrated) |
| Yellow Marrow (Bone Marrow) | Bone Marrow (Not Infiltrated) |
| Gray Matter | Brain (Grey Matter) |
| White Matter | Brain (White Matter) |
| Breast Fat | Breast Fat |
| Cartilage | Cartilage |
| — | Cerebellum |
| Cerebro Spinal Fluid | Cerebro Spinal Fluid |
| — | Cervix |
| — | Colon |
| — | Cornea |
| — | Dura |
| — | Eye Tissues (Sclera |
| — | Fat (Average Infiltrated) |
| Adipose Tissue (Fat) | Fat (Not Infiltrated) |
| — | Gall Bladder |
| Gall Bladder Bile | Gall Bladder Bile |
| Heart | Heart |
| Kidney | Kidney |
| Eye Lens | Lens Cortex |
| — | Lens Nucleus |
| Liver | Liver |
| Lung Deflated | Lung (Deflated) |
| Lung Inflated | Lung (Inflated) |
| Muscle | Muscle |
| — | Nerve |
| Ovary | Ovary |
| Skin | Skin (Dry) |
| — | Skin (Wet) |
| Small Intestine | Small Intestine |
| Spleen | Spleen |
| Stomach | Stomach |
| — | Tendon |
| Testis | Testis |
| Lymph, Pancreas, Prostate, Thyroid | Thyroid |
| — | Tongue |
| Trachea | Trachea |
| — | Uterus |
| — | Vitreous Humor |

TABLE III

| Tissue Type/Parameter | ef | del1 | tau1 (ps) | alf1 | del2 | tau2 (ns) | alf2 | sig | del3 | tau3 (us) | alf3 | del4 | tau4 (ms) | alf4 |
|---|---|---|---|---|---|---|---|---|---|---|---|---|---|---|
| Aorta | 4 | 40 | 8.842 | 0.1 | 50 | 3.183 | 0.1 | 0.25 | 1.00E+05 | 159.155 | 0.2 | 1.00E+07 | 1.592 | 0 |
| Blood | 4 | 56 | 8.377 | 0.1 | 5200 | 132.629 | 0.1 | 0.7 | 0.00E+00 | 159.155 | 0.2 | 0.00E+00 | 15.915 | 0 |
| Bone (Cancellous) | 2.5 | 18 | 13.263 | 0.22 | 300 | 79.577 | 0.25 | 0.07 | 2.00E+04 | 159.155 | 0.2 | 2.00E+07 | 15.915 | 0 |
| Bone (Cortical) | 2.5 | 10 | 13.263 | 0.2 | 180 | 79.577 | 0.2 | 0.02 | 5.00E+03 | 159.155 | 0.2 | 1.00E+05 | 15.915 | 0 |
| Bone Marrow (Not Infiltrated) | 2.5 | 3 | 7.958 | 0.2 | 25 | 15.915 | 0.1 | 0 | 5.00E+03 | 1591.55 | 0.1 | 2.00E+06 | 15.915 | 0.1 |
| Brain (Grey Matter) | 4 | 45 | 7.958 | 0.1 | 400 | 15.915 | 0.15 | 0.02 | 2.00E+05 | 106.103 | 0.22 | 4.50E+07 | 5.305 | 0 |
| Brain (White Matter) | 4 | 32 | 7.958 | 0.1 | 100 | 7.958 | 0.1 | 0.02 | 4.00E+04 | 53.052 | 0.3 | 3.50E+07 | 7.958 | 0.2 |
| Breast Fat | 2.5 | 3 | 7.958 | 0.1 | 15 | 63.66 | 0.1 | 0.01 | 5.00E+04 | 454.7 | 0.1 | 2.00E+07 | 13.26 | 0 |
| Cartilage | 4 | 38 | 13.263 | 0.15 | 2500 | 144.686 | 0.15 | 0.15 | 1.00E+05 | 318.31 | 0.1 | 4.00E+07 | 15.915 | 0 |
| Cerebro Spinal Fluid | 4 | 65 | 7.958 | 0.1 | 40 | 1.592 | 0 | 2 | 0.00E+00 | 159.155 | 0 | 0.00E+00 | 15.915 | 0 |
| Fat (Not Infiltrated) | 2.5 | 3 | 7.958 | 0.2 | 15 | 15.915 | 0.1 | 0.01 | 3.30E+04 | 159.155 | 0.05 | 1.00E+07 | 7.958 | 0.01 |
| Gall Bladder Bile | 4 | 66 | 7.579 | 0.05 | 50 | 1.592 | 0 | 1.4 | 0.00E+00 | 159.155 | 0.2 | 0.00E+00 | 15.915 | 0.2 |
| Heart | 4 | 50 | 7.958 | 0.1 | 1200 | 159.155 | 0.05 | 0.05 | 4.50E+05 | 72.343 | 0.22 | 2.50E+07 | 4.547 | 0 |
| Kidney | 4 | 47 | 7.958 | 0.1 | 3500 | 198.944 | 0.22 | 0.05 | 2.50E+05 | 79.577 | 0.22 | 3.00E+07 | 4.547 | 0 |
| Lens Cortex | 4 | 42 | 7.958 | 0.1 | 1500 | 79.577 | 0.1 | 0.3 | 2.00E+05 | 159.155 | 0.1 | 4.00E+07 | 15.915 | 0 |
| Liver | 4 | 39 | 8.842 | 0.1 | 6000 | 530.516 | 0.2 | 0.02 | 5.00E+04 | 22.736 | 0.2 | 3.00E+07 | 15.915 | 0.05 |
| Lung (Deflated) | 4 | 45 | 7.958 | 0.1 | 1000 | 159.155 | 0.1 | 0.2 | 5.00E+05 | 159.155 | 0.2 | 1.00E+07 | 15.915 | 0 |
| Lung (Inflated) | 2.5 | 18 | 7.958 | 0.1 | 500 | 63.662 | 0.1 | 0.03 | 2.50E+05 | 159.155 | 0.2 | 4.00E+07 | 7.958 | 0 |
| Muscle | 4 | 50 | 7.234 | 0.1 | 7000 | 353.678 | 0.1 | 0.2 | 1.20E+06 | 318.31 | 0.1 | 2.50E+07 | 2.274 | 0 |
| Ovary | 4 | 40 | 8.842 | 0.15 | 400 | 15.915 | 0.25 | 0.3 | 1.00E+05 | 159.155 | 0.27 | 4.00E+07 | 15.915 | 0 |
| Skin (Dry) | 4 | 32 | 7.234 | 0 | 1100 | 32.481 | 0.2 | 0 | 0.00E+00 | 159.155 | 0.2 | 0.00E+00 | 15.915 | 0.2 |
| Small Intestine | 4 | 50 | 7.958 | 0.1 | 10000 | 159.155 | 0.1 | 0.5 | 5.00E+05 | 159.155 | 0.2 | 4.00E+07 | 15.915 | 0 |
| Spleen | 4 | 48 | 7.958 | 0.1 | 2500 | 63.662 | 0.15 | 0.03 | 2.00E+05 | 265.258 | 0.25 | 5.00E+07 | 6.366 | 0 |
| Stomach | 4 | 60 | 7.958 | 0.1 | 2000 | 79.577 | 0.1 | 0.5 | 1.00E+05 | 159.155 | 0.2 | 4.00E+07 | 15.915 | 0 |
| Testis | 4 | 55 | 7.958 | 0.1 | 5000 | 159.155 | 0.1 | 0.4 | 1.00E+05 | 159.155 | 0.2 | 4.00E+07 | 15.915 | 0 |
| Thyroid | 4 | 55 | 7.958 | 0.1 | 2500 | 159.155 | 0.1 | 0.5 | 1.00E+05 | 159.155 | 0.2 | 4.00E+07 | 15.915 | 0 |
| Trachea | 2.5 | 38 | 7.958 | 0.1 | 400 | 63.662 | 0.1 | 0.3 | 5.00E+04 | 15.915 | 0.2 | 1.00E+06 | 15.915 | 0 |

TABLE IV

| ACPSO Parameters | |
|---|---|
| particles | 30 |
| w | 0.9 to 0.4 |
| c1 | 2.2 to 1.8 |
| c2 | 1.8 to 2.2 |

TABLE V

| | Parameter | | | |
|---|---|---|---|---|
| Tissue Type | Eps Inf | Eps S | Tau | Sigma |
| Breast Fat | 2.157463 | 5.119092 | 1.30E−11 | 0.043826 |
| Fat (Not Infiltrated) | 3.363668 | 5.359808 | 1.30E−11 | 0.046582 |
| Bone Marrow (Not Infiltrated) | 3.350332 | 5.377789 | 1.30E−11 | 0.035815 |
| Bone (Cortical) | 3.211419 | 11.42837 | 1.30E−11 | 0.130251 |
| Bone (Cancellous) | 4.056299 | 18.53915 | 1.30E−11 | 0.332491 |
| Lung (Inflated) | 7.691772 | 21.22595 | 1.30E−11 | 0.421393 |
| Brain (White Matter) | 13.18199 | 37.51046 | 1.30E−11 | 0.522647 |
| Cartilage | 5.858209 | 39.03475 | 1.30E−11 | 0.73538 |
| Skin (Dry) | 15.5336 | 40.02 | 1.30E−11 | 0.754357 |
| Trachea | 13.61123 | 41.38144 | 1.30E−11 | 0.683907 |
| Aorta | 13.65059 | 44.16795 | 1.30E−11 | 0.597698 |
| Liver | 13.03465 | 44.50726 | 1.30E−11 | 0.778227 |
| Ovary | 13.271 | 45.62758 | 1.30E−11 | 1.272727 |
| Lens Cortex | 16.39723 | 46.48319 | 1.30E−11 | 0.690587 |
| Lung (Deflated) | 17.06075 | 50.31581 | 1.30E−11 | 0.756894 |
| Brain (Grey Matter) | 16.94483 | 50.80359 | 1.30E−11 | 0.848955 |
| Spleen | 17.74894 | 54.40161 | 1.30E−11 | 1.186971 |
| Kidney | 17.25049 | 54.53156 | 1.30E−11 | 1.329075 |
| Muscle | 21.05172 | 55.03768 | 1.30E−11 | 0.82327 |
| Small Intestine | 18.4452 | 56.41983 | 1.30E−11 | 2.089701 |
| Heart | 18.23857 | 56.83019 | 1.30E−11 | 1.141309 |
| Thyroid | 20.24872 | 59.63522 | 1.30E−11 | 0.903754 |
| Testis | 20.16221 | 59.95633 | 1.30E−11 | 1.080744 |
| Blood | 19.07361 | 60.62518 | 1.30E−11 | 1.408626 |
| Stomach | 21.69613 | 64.80569 | 1.30E−11 | 1.041605 |
| Cerebro Spinal Fluid | 23.40068 | 69.18522 | 1.30E−11 | 2.240447 |
| Gall Bladder Bile | 26.03424 | 72.13955 | 1.30E−11 | 1.621685 |
| Water | 38.81363 | 77.53412 | 1.30E−11 | 8.33E−18 |

TABLE VI

| | Parameter | | | |
|---|---|---|---|---|
| Tissue Type | Eps Inf | Eps S | Tau | Sigma |
| Lung (Inflated) | 7.692 | 21.226 | 1.30E−11 | 0.421 |
| Fat | 3.350 | 5.360 | 1.30E−11 | 0.044 |
| Water | 38.885 | 77.379 | 1.30E−11 | 0.000 |
| Muscle Region high | 20.205 | 59.796 | 1.30E−11 | 1.301 |
| Muscle Region medium | 17.250 | 54.402 | 1.30E−11 | 0.904 |
| Muscle Region low | 13.631 | 44.338 | 1.30E−11 | 0.746 |
| Bone (Cancellous) | 4.056 | 18.539 | 1.30E−11 | 0.332 |
| Bone (Cortical) | 3.211 | 11.428 | 1.30E−11 | 0.130 |

TABLE VII

| CT Number (Hounsfield Unit) | Pixel Value | Tissue Type/ Parameter | Eps Inf | Eps S | Tau | Sigma | Min Eps S | Increment | Start Incr | Stop Incr |
|---|---|---|---|---|---|---|---|---|---|---|
| "−1024 to −840" | "0 to 183" | Air | 1 | 1 | 1.30E−11 | 0 | 0.9 | 5.46E−04 | 0.9 | 1 |
| "−840 to −190" | "184 to 833" | Lung (Inflated) | 7.692 | 21.226 | 1.30E−11 | 0.421 | 19.1034 | 1.54E−04 | 0.9 | 1 |
| "−190 to −4" | "834 to 1019" | Fat | 3.350 | 5.360 | 1.30E−11 | 0.044 | 4.824 | 5.41E−04 | 0.9 | 1 |
| "−4 to +8" | "1020 to 1031" | Water | 38.885 | 77.379 | 1.30E−11 | 0.000 | 69.6411 | 0.009090909 | 1 | 0.9 |
| "8 to 45" | "1032 to 1068" | Muscle Region high | 20.205 | 59.796 | 1.30E−11 | 1.301 | 56.8062 | 0.001388889 | 1 | 0.95 |
| "45 to 83" | "1069 to 1106" | Muscle Region medium | 17.250 | 54.402 | 1.30E−11 | 0.904 | 51.6819 | 0.001351351 | 1 | 0.95 |
| "83 to 120" | "1107 to 1143" | Muscle Region low | 13.631 | 44.338 | 1.30E−11 | 0.746 | 39.9042 | 0.002777778 | 1 | 0.9 |
| "120 to 300" | "1144 to 1323" | Bone (Cancellous) | 4.056 | 18.539 | 1.30E−11 | 0.332 | 16.6851 | 5.59E−04 | 1 | 0.9 |
| "300 to 3071" | "1324 to 4095" | Bone (Cortical) | 3.211 | 11.428 | 1.30E−11 | 0.130 | 10.2852 | 3.61E−05 | 1 | 0.9 |

We claim:

1. A method for converting from microwave image data to an image encoded in Hounsfield units, comprising the steps of:
    a. collecting microwave image data of an object and reconstructing a dielectric image;
    b. assigning a tissue type or tissue grouping to sub-regions in the dielectric image; and
    c. using the assigned tissue type or tissue grouping and a relationship, converting the dielectric image to an image encoded in Hounsfield units using at least one processor.

2. The method of claim 1, wherein, prior to step a, the microwave image data is collected at a remote acquisition site and transmitted to a centralized computing environment having a centralized reconstruction database.

3. The method of claim 1, wherein the object is a human.

4. The method of claim 1, further comprising the step of visually displaying the image encoded in Hounsfield units at remote viewing locations.

5. The method of claim 1, wherein, prior to step b, the dielectric image is further encoded (1) through the use of a relationship with a characteristic of tissue associated with a body at a microwave frequency and/or (2) to improve viewability when an image is displayed.

6. The method of claim 1, wherein the image encoded in Hounsfield units is further encoded in DICOM format.

7. A method for converting from microwave image data to Hounsfield data, comprising the steps of:
    a. receiving data representing scattered microwave signals of an object;
    b. reconstructing a dielectric image from the data representing scattered microwave signals and determining permittivity values at a given frequency;

c. assigning a tissue type or tissue grouping to sub-regions in the dielectric image based on the permittivity; and d. using a relationship between (1) a variation of Hounsfield units for a tissue type or tissue grouping and (2) a variation of permittivity for a tissue type or tissue grouping at the given frequency, converting the dielectric image to an image encoded in Hounsfield units using at least one processor.

8. The method of claim 7, wherein, prior to step a, the data representing scattered microwave signals is collected at an acquisition site.

9. The method of claim 7, wherein, prior to step a, the data representing scattered microwave signals is collected at a remote acquisition site.

10. The method of claim 7, wherein the object is a human.

11. The method of claim 7, wherein step c includes assigning a tissue type or tissue grouping based on real permittivity and either minimum or maximum permittivity.

12. The method of claim 7, wherein the method uses said relationship for the given frequency and another relationship for another frequency.

13. The method of claim 7, further comprising the step of visually displaying the image encoded in Hounsfield units at remote viewing locations.

14. The method of claim 7, wherein, prior to step c, the dielectric image is further encoded (1) through the use of a relationship with a characteristic of tissue associated with a body at a microwave frequency and/or (2) to improve viewability when an image is displayed.

15. The method of claim 7, wherein the image encoded in Hounsfield units is further encoded in DICOM format.

16. A method for converting from microwave image data to Hounsfield data, comprising the steps of:

a. receiving data representing scattered microwave signals of an object;

b. reconstructing a dielectric image from the data representing scattered microwave signals and determining permittivity values at multiple frequencies;

c. converting the permittivity values at multiple frequencies to a model relationship describing the permittivity;

d. assigning a tissue type or tissue grouping to sub-regions of the dielectric image based on the model relationship; and e. using a relationship between (1) a variation of Hounsfield units for a tissue type or tissue grouping and (2) a variation of at least one parameter of the model relationship, converting the dielectric image to an image encoded in Hounsfield units using at least one processor.

17. The method of claim 16, wherein the object is a human.

18. The method of claim 16, wherein step d includes assigning tissue type or tissue grouping based on at least static permittivity.

19. The method of claim 16, wherein the model relationship is a Debye model and in step d the tissue type or tissue grouping is assigned based on at least one Debye parameter.

20. The method of claim 16, wherein, prior to step a, the data representing scattered microwave signals is collected at an acquisition site.

21. The method of claim 16, wherein, prior to step a, the data representing scattered microwave signals is collected at a remote acquisition site.

22. The method of claim 16, further comprising the step of visually displaying the image encoded in Hounsfield units at remote viewing locations.

23. The method of claim 16, wherein, prior to step c, the dielectric image is further encoded (1) through the use of a relationship with a characteristic of tissue associated with a body at a microwave frequency and/or (2) to improve viewability when an image is displayed.

24. The method of claim 16, wherein the image encoded in Hounsfield units is further encoded in DICOM format.

25. A method of imaging, comprising:

a. collecting microwave scattering data of an object and reconstructing a dielectric image;

b. converting the dielectric image to an MRI intensity encoded image using at least one processor; and c. generating a DICOM encoded image of the MRI intensity encoded image.

26. The method of claim 25, wherein the object is a human.

27. A method of imaging, comprising:

a. collecting microwave scattering data of an object and reconstructing a dielectric image;

b. collecting user generated or study-selected MRI scanner acquisition parameters;

c. creating a water content map from the dielectric image using at least one processor;

d. obtaining a T1 map from the water content map using at least one processor; and e. creating an MRI intensity image using the scanner acquisition parameters and the T1 map.

28. The method of imaging of claim 27, further comprising the step of encoding the MRI intensity image in DICOM format.

29. The method of claim 27, wherein the object is a human.

30. An image processing method, the method comprising:

a. receiving a CT image of an object;

b. converting the CT image into a dielectric image using a frequency dependent model and at least one processor, wherein converting the CT image into the dielectric image comprises determining permittivity values; and c. displaying the dielectric image.

31. The image processing method of claim 30, wherein the method further comprises assigning a tissue type or tissue grouping to sub-regions in the CT image and using the assigned tissue type or tissue grouping and a relationship, converting the CT image into the dielectric image.

32. The image processing method of claim 30, wherein the method further comprises assigning a tissue type or tissue grouping to sub-regions in the CT image based on Hounsfield units and using a relationship between the variation of Hounsfield units and of at least one parameter of a model relationship over a frequency range for a tissue type or tissue grouping, converting the CT image into the dielectric image.

33. The image processing method of claim 30, wherein converting the CT image into the dielectric image further comprises calculating Debye parameters.

* * * * *

UNITED STATES PATENT AND TRADEMARK OFFICE
CERTIFICATE OF CORRECTION

PATENT NO. : 9,111,334 B2
APPLICATION NO. : 14/069661
DATED : August 18, 2015
INVENTOR(S) : Todd R. McCollough and William J. McCollough It is certified that error appears in the above-identified patent and that said Letters Patent is hereby corrected as shown below:

Column 6, line 43 each occurrence of the term '∈' in the formula should be changed to -$\varepsilon$- and read as follows:

$\varepsilon(\omega) = \varepsilon'(\omega) + i * \varepsilon''(\omega)$

Column 6, lines 44 and 51 each occurrence of the term '∈' should be changed to -$\varepsilon$-

Column 6, line 49 each occurrence of the term '∈' in the formula should be changed to -$\varepsilon$- and read as follows:

$\sigma = -w\varepsilon''\varepsilon_0$

Column 14, lines 11-15 the portion of the equation "$(1 - a_i)$" should be raised as a power and read as follows:

$$\varepsilon(\omega) = \varepsilon_\infty + \sum_{i=1}^{4} \frac{\Delta\varepsilon_i}{1 + (j\omega\tau_i)^{(1-a_i)}} + \frac{\sigma_s}{j\omega\varepsilon_0}$$

Column 15, line 65 in the sentence "Where dielectric.lung_inflated=2_=24.7727-21.3530i..." the "2_=" should be deleted. The sentence should read as follows:

"Where dielectric.lung_inflated=24.7727-21.3530i..."

Column 19, lines 13-19 The space between "log" and "10" in the formulas should be deleted;

Signed and Sealed this
Twenty-third Day of February, 2016

Michelle K. Lee
*Director of the United States Patent and Trademark Office*

Column 19, line 13 '∈∞' should be changed to --$\varepsilon_\infty$--; Column 19, line 14 'Δ∈₁' should be changed to --$\Delta\varepsilon_1$-- should read as follows:

$log_{10}(\varepsilon_\infty) \in (0,1)$
$log_{10}(\Delta\varepsilon_1) \in (-3,8)$
$log_{10}(\tau) \in (-12,-1)$
$log_{10}(\sigma_s) \in (-4,0)$ Column 19, lines 20-22 for the term '∈', each occurrence should read --$\varepsilon$--

Column 20, lines 34, 35, 39-41, 44 and 46 for the term '∈', each occurrence should read --$\varepsilon$--

Column 22, line 1 should read as follows:

--For example if $H_{in}(x,y)$=-700 then--

Column 23, lines 26 and 32 the term '∈', each occurrence, should read --$\varepsilon$.--

Column 26, lines 14-16 The equation should read as follows:

$$P_{out}(x,y) = \frac{(-D_{in\_eps\_s}(x,y) + 18.539)}{18.539} * \frac{1}{incr} + 1144$$

Column 27, lines 34 and 48 the term '∈', each occurrence, should read --$\varepsilon$--

Column 33, Table IV, the bold line underneath "particles and 30" should be deleted